(12) United States Patent
Mitani et al.

(10) Patent No.: US 6,169,051 B1
(45) Date of Patent: Jan. 2, 2001

(54) METALLOCENE COMPOUNDS, PROCESSES FOR THE PREPARATION THEREOF, CATALYST COMPONENTS FOR OLEFIN POLYMERIZATION, AND PROCESSES FOR THE PRODUCTION OF OLEFIN POLYMERS

(75) Inventors: Seiki Mitani, Kanagawa-ken; Masato Nakano; Jun Saito, both of Chiba-ken; Hiroshi Yamazaki, Saitama-ken; Keisuke Kimura, Chiba-ken, all of (JP)

(73) Assignee: Chisso Corporation, Osaku-Fu (JP)

( * ) Notice: Under 35 U.S.C. 154(b), the term of this patent shall be extended for 0 days.

(21) Appl. No.: 09/236,322

(22) Filed: Jan. 25, 1999

(51) Int. Cl.$^7$ .............................. B01J 31/00; C07F 17/00; C08F 4/02
(52) U.S. Cl. ............................... 502/103; 556/11; 556/12; 556/53; 546/4; 548/103; 548/403; 549/3; 549/206; 502/117; 502/120; 526/126; 526/160; 526/357; 526/943; 987/2
(58) Field of Search .................... 546/4; 548/103, 548/403; 549/3, 206; 556/11, 12, 53; 502/103, 117, 120; 526/126, 160, 351, 943; 987/2

(56) References Cited

U.S. PATENT DOCUMENTS 5,585,509 * 12/1996 Langhauser et al. ................... 556/11
5,840,947 * 11/1998 Kuber et al. .............................. 556/8

FOREIGN PATENT DOCUMENTS 7-258282 10/1995 (JP).
8-183814 7/1996 (JP).

OTHER PUBLICATIONS

"Elastomeric Polypropylene from Unbridged 2–Arylindenyl Zirconocenes: Modeling Polymerization Behavior Using ansa–Metallocene Analogues", J. Am. Chem. Soc. 1998, vol. 120, pp. 11316–11322.

"Polymerization Catalysts with Cyclopentadienyl Ligands Ring–Fused to Pyrrole and Thiophene Heterocycles", J. Am. Chem. Soc. 1998, vol. 120, pp. 10786–10787.

* cited by examiner

Primary Examiner—Porfirio Nazario-Gonzalez
(74) Attorney, Agent, or Firm—McDermott, Will & Emery

(57) ABSTRACT

A metallocene compound is provided wherein to a transition metal compound is bonded a multidentate compound wherein a substituted cycloalkadienyl ring $CA^1$ having therein a heteroaromatic group Ra containing an oxygen, sulfur or nitrogen atom on a cycloalkadienyl ring, preferably the five-membered ring thereof, and an unsubstituted or substituted cycloalkadienyl group $CA^2$ or —($R^1$)N—, —O—, —S— or —($R^1$)P—, preferably $CA^2$, more preferably a substituted cycloalkadienyl group identical with $CA^1$ are bonded through a divalent linking group. The metallocene compound is suitable as a principal ingredient of a catalyst for the polymerization of olefins, particularly achieving a very high effect in making the molecular weight of a polypropylene higher.

35 Claims, 3 Drawing Sheets

METALLOCENE COMPOUNDS, PROCESSES FOR THE PREPARATION THEREOF, CATALYST COMPONENTS FOR OLEFIN POLYMERIZATION, AND PROCESSES FOR THE PRODUCTION OF OLEFIN POLYMERS

TECHNICAL FIELD

This invention relates to new metallocene compounds useful as a catalyst component for olefin polymerization. More particularly, the invention relates to metallocene compounds consisting of complex compounds wherein a cycloalkadienyl ring-containing multidentate compound substituted on the ring by a heteroaromatic group containing an oxygen, a sulfur or a nitrogen atom is coordinated to a Group VIB transition metal atom and also to the processes for the preparation thereof.

Further, the invention relates to catalysts for olefin polymerization containing said metallocene compounds and processes for the production of olefin polymers using them.

BACKGROUND ART

As a catalyst substituted for Ziegler-Natta catalysts which have been used in the polymerization of olefins, a part of the metallocene compounds is being used which consist of a complex compound wherein a multidentate compound containing a π-electron donor such as unsubstituted or substituted cycloalkadienyl groups is coordinated to a transition metal atom, the unsubstituted or substituted cycloalkadienyl groups including e.g., unsubstituted or substituted cyclopentadienyl groups, unsubstituted or substituted indenyl groups, unsubstituted or substituted tetrahydroindenyl groups, and unsubstituted or substituted fluorenyl groups.

In recent years, various metallocene compounds have been proposed having higher olefin polymerization activity per mole of a transition metal atom. It is known that the polymers of α-olefin having 3 or more carbon atoms, in particular, propylene polymers, prepared by using a chiral metallocene compound have high stereoregularity, the chiral metallocene compound being the compound wherein a multidentate compound having two substituted cycloalkadienyl groups bonded with a divalent linking group is coordinated to a transition metal atom (J. Am. Chem. Soc. 1998, 120, 11316–11322).

Further, the development of metallocene compounds with high olefin polymerization activity has continued. Various metallocene compounds have been proposed wherein a heteroatom is introduced into the substituent or cycloalkadiene ring in the substituted cycloalkadienyl group.

For instance, Japanese Patent Kokai 7-258282 discloses metallocene compounds wherein the 2-position of the indenyl group is substituted by a saturated group containing a heteroatom such as nitrogen, phosphorus, arsenic, antimony, bismuth or the like, specifically those wherein 2-pyrrolidino-1-indene is linked through a divalent linking group and coordinated to a transition metal atom.

Japanese Patent Kokai 8-183814 discloses chiral metallocene compounds wherein the 4-position of the indenyl group is substituted by unsubstituted or substituted 1-pyrrolyl group, 1-indolyl group or the like, specifically those wherein 4-(1-indolyl)-2-methylindene is linked through a divalent linking group and coordinated to a transition metal atom.

J. Am. Chem. Soc. 1998, 120, 10786–10787 discloses metallocene compounds wherein a heteroatom-containing cycloalkadiene having a thiophene ring or a pyrrol ring condensed to a cyclopentadiene ring is linked through a divalent linking group and coordinated to a transition metal atom.

DISCLOSURE OF THE INVENTION

As mentioned above, there are various proposals for introducing a heteroatom into a π-electron donor. Except for the compounds disclosed in Japanese Patent Kokai 8-183814, however, the metallocene compounds are not known wherein the substituted cycloalkadienyl group-containing compounds having a heteroaromatic group containing an oxygen atom, a sulfur atom or a nitrogen atom on a cycloalkadiene ring, particularly on the 5-membered ring thereof are coordinated to a transition metal atom.

The present invention provides a metallocene compound represented by the following formula (1)

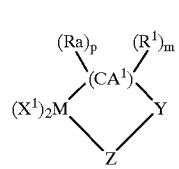

(1)

wherein $CA^1$ represents a substituted cycloalkadienyl group selected from the group consisting of a substituted cyclopentadienyl group, a substituted indenyl group, a substituted tetrahydroindenyl group, a substituted benzoindenyl group and a substituted fluorenyl group; each Ra represents independently a monocyclic or polycyclic heteroaromatic group containing a heteroatom selected from the group consisting of an oxygen atom, a sulfur atom and a nitrogen atom in a 5- or 6-membered ring; each $R^1$ represents independently a halogen atom, a hydrocarbon group of 1–20 carbons, a halogenated hydrocarbon group wherein a part or all of the hydrogen atoms in the hydrocarbon group are substituted by a halogen atom, a silyl group substituted by said hydrocarbon group or said halogenated hydrocarbon group, an amino group substituted by said hydrocarbon group or a monocyclic or polycyclic amino group;

p is an integer of 1–8;

m is 0 or an integer of 1–8;

Z represents a linking group selected from the group consisting of $(CA^2)$ $(Ra)_q(R^1)_n$, —O—, —S—, —NR$^1$— and —PR$^1$— wherein $CA^2$ represents an unsubstituted or substituted cycloalkadienyl group; Ra and $R^1$ have the same meanings as defined above, Ra may be identical with or different from said Ra on $CA^1$ and $R^1$ may be identical with or different from said $R^1$ on $CA^1$; and q and n are each independently 0 or an integer of 1–8;

Y represents a divalent linking group selected from the group consisting of —C($R^2$)$_2$—, —C$_2$($R^2$)$_4$—, —C$_6$($R^2$)$_{10}$—, —C$_6$($R^2$)$_4$—, —Si($R^2$)$_2$—, —Ge($R^2$)$_2$— and —Sn($R^2$)$_2$— wherein each $R^2$ represents independently a hydrogen atom, a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group;

M represents a transition metal atom selected from the group consisting of Ti, Zr and Hf; and each $X^1$ represents independently a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group, and a process for the preparation thereof.

Further, the invention provides a catalyst for olefin polymerization comprising said metallocene compound and an aluminoxane, and a process for the production of an olefin polymer wherein an olefin is polymerized in the presence of said olefin polymerization catalyst and in the presence or absence of an organic aluminum compound.

DETAILED DESCRIPTION

Figure 1:
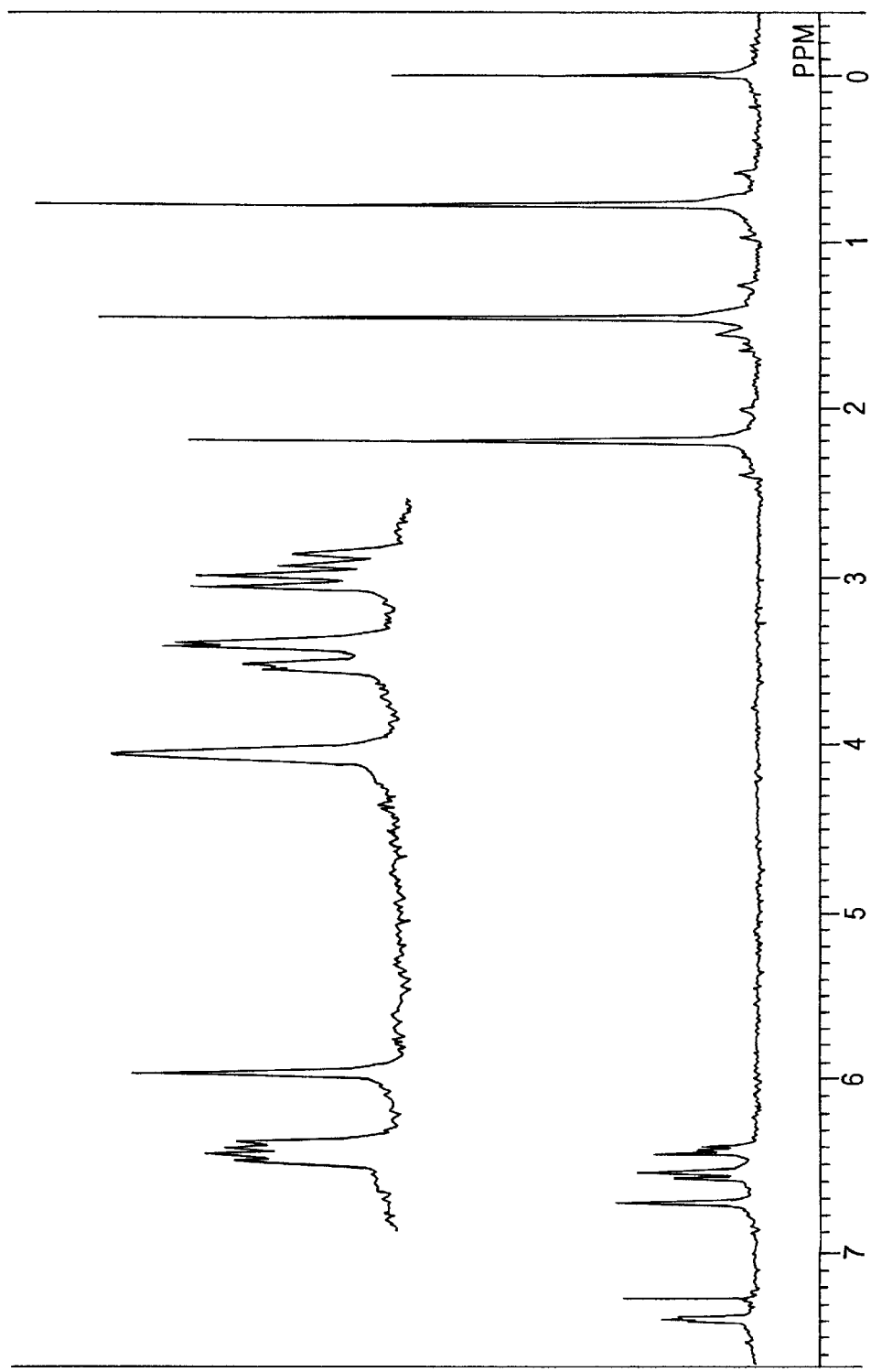
FIG. 1 is $^1$H-NMR chart determined in deuteriochloroform for compound No. 95 synthesized in Example 3, rac-dimethylsilylenebis[2-(2-furyl)-4,5-dimethyl-cyclopentadienyl]zirconium dichloride.

The metallocene compounds of the present invention represented by said formula (1) are largely classified into the compounds having a fundamental structure wherein Z is $(Ra)_q(R^1)_n(CA^2)$ and the compounds having a fundamental structure wherein Z is selected from —O—, —S—, —NR$^1$— and —PR$^1$—.

The substituted cycloalkadienyl group CA$^1$ is a substituted cyclopentadienyl group, a substituted indenyl group, a substituted tetrahydroindenyl group, a substituted benzoindenyl group or a substituted fluorenyl group, one or more hydrogens in the cycloalkadiene ring are substituted by the heteroaromatic group Ra and may be further substituted by the substituent R$^1$.

Preferably, the heteroaromatic group Ra substitutes a hydrogen atom on the 5-membered ring in the substituted cycloalkadienyl group CA$^1$, i.e., a hydrogen atom is substituted at a 2- and/or 3-position of the substituted cycloalkadienyl group CA$^1$. Thus, preferable substituted cycloalkadienyl group CA$^1$ is a substituted cyclopentadienyl group, a substituted indenyl group, a substituted tetrahydroindenyl or benzoindenyl group, more preferably a substituted cyclopentadienyl group or a substituted indenyl group.

The number of substitution by the heteroaromatic group Ra on the substituted cycloalkadienyl group CA$^1$: p is an integer of 1 to 8, preferably 1 to 4, more preferably 1 or 2.

CA$^2$ in $(Ra)_q(R^1)_n(CA^2)$ selected for the group Z is an unsubstituted or substituted cyclopentadienyl group, an unsubstituted or substituted indenyl group, an unsubstituted or substituted tetrahydroindenyl group, an unsubstituted or substituted benzoindenyl group, or an unsubstituted or substituted fluorenyl group. These substituted cycloalkadienyl groups are those wherein one or more hydrogen atoms on the cycloalkadienyl ring are substituted by either or both of the heteroaromatic group Ra and the substituent R$^1$.

For the case where CA$^2$ is the cycloalkadienyl group substituted by the heteroaromatic group Ra, it is preferable that the heteroaromatic group Ra substitutes a hydrogen atom on the 5-membered ring in the cycloalkadienyl group, similarly to the substituted cycloalkadienyl group CA$^1$.

The number of substitution by the heteroaromatic group Ra on CA$^2$: q is 0 or an integer of 1 to 8, preferably 1 to 4, more preferably 1 or 2.

The heteroaromatic group Ra which substitutes a hydrogen atom on the respective cyclopentadienyl rings of CA$^1$ and CA$^2$ is the groups containing an oxygen atom, a sulfur atom or a nitrogen atom in the aromatic ring, e.g., furyl, thienyl, pyridyl, benzofliryl, benzothienyl, quinolyl, or pyrrolyl or indolyl having a bond at positions other than the 1-position, and those groups may be further substituted by the substituent R$^1$ as mentioned later. Where CA$^1$ and CA$^2$ are respectively substituted by Ra or plural Ra, said Ra may be identical or different.

Each of the substituents R$^1$ on CA$^1$ and CA$^2$ is a halogen atom such as fluorine, chlorine, bromine, iodine or the like; a hydrocarbon group of 1–20 carbons such as an alkyl group of 1–20 carbons, an aryl group of 6–20 carbons, an aralkyl group of 7–20 carbons, an alkoxy group of 1–20 carbons, an aryloxy group of 6–20 carbons, an aralkyloxy group of 7–20 carbons or the like; a halogenated hydrocarbon group wherein a part or all of the hydrogen atoms in said hydrocarbon group are substituted by said halogen atom; a silyl group tri-substituted by said hydrocarbon group and/or said halogenated hydrocarbon group; an amino group di-substituted by said hydrocarbon group; or a monocyclic or polycyclic amino group. Where CA$^1$ and CA$^2$ are respectively substituted by R$^1$ or plural R$^1$, said R$^1$ may be identical or different.

The number of substitution by R$^1$ on CA$^1$ and CA$^2$: each of m and n is 0 or an integer of 1 to 8, preferably 1 to 4, more preferably 1 or 2.

As the alkyl group of 1–20 carbons are recited, for example, a straight- or branched-chain alkyl group such as methyl, ethyl, propyl, i-propyl, n-butyl, i-butyl, tert-butyl, sec-butyl, pentyl, hexyl, heptyl, octyl, 2-ethylhexyl, nonyl, decyl, dodecyl, octadecyl or the like, and a cyclic alkyl group which may be substituted by said chain alkyl group such as cyclopropyl, cycloheptyl, cyclohexyl or the like.

As the aryl group of 6–20 carbons are recited, for example, phenyl, naphthyl, anthryl or the like; and tolyl, xylyl, trimethylphenyl or the like which are further substituted by said alkyl group or the like. As the aralkyl group of 7–20 carbons are recited benzyl, naphthylmethyl, anthrylmethyl or the like; and (methylphenyl)methyl, (dimethylphenyl) methyl, (trimethylphenyl) methyl, (ethylphenyl)methyl, (propylphenyl)methyl, (butylphenyl) methyl or the like which are further substituted by said alkyl group or the like.

As the alkoxy group of 1–20 carbons are recited chain and cyclic alkoxy groups having said alkyl group, such as methoxy, ethoxy, propoxy, isopropoxy, butoxy, t-butoxy, hexyloxy, cyclohexyloxy or the like; as the aryloxy group of 6–20 carbons are recited substituted or unsubstituted aryloxy groups having said aryl group such as phenoxy, naphthyloxy, anthryloxy or the like; and as the aralkyloxy group of 7–20 carbons are recited aralkyloxy groups having said aralkyl group such as benzyloxy or the like.

As the halogenated hydrocarbon group are recited halogenated alkyl groups, halogenated aryl groups, halogenated aralkyl groups, halogenated alkoxy groups, halogenated aryloxy groups, halogenated aralkyloxy groups or the like wherein a part or all of the hydrogen atoms in said hydrocarbon group are substituted by said halogen atom, such as monochloromethyl, dichloromethyl, trichloromethyl, perfluoroethyl, monochlorophenyl, difluorophenyl, monochlorobenzyl or the like.

As the silyl group are recited silyl groups substituted by said hydrocarbon group and/or said halogenated hydrocarbon group, e.g., trimethylsilyl, triethylsilyl, triphenylsilyl, tribenzylsilyl, triethoxysilyl, dimethylphenoxysilyl or the like.

As the amino group are recited amino groups having said hydrocarbon group such as dimethylamino, diethylamino, methylethylamino or the like, and saturated or unsaturated monocyclic or polycyclic amino groups such as 1-pyrrolidyl, 1-pyrrolyl, 1-indolyl or the like.

The divalent linking group Y is —C($R^2$)$_2$—, e.g., methylene; —C$_2$($R^2$)$_4$—, e.g., ethylene; —C$_6$($R^2$)$_{10}$—, e.g., cyclohexylene; —C$_6$($R^2$)$_4$—, e.g., phenylene; —Si($R^2$)$_2$—, e.g., silylene; —Ge($R^2$)$_2$—, e.g., germanylene; or —Sn($R^2$)$_2$—, e.g., stanylene wherein the substituent $R^2$ is independently a hydrogen atom, a halogen atom, a hydrocarbon group of 1–20 carbons as defined above for the substituent $R^1$, a halogenated hydrocarbon group or a silyl group.

Preferred linking group Y is —C($R^2$)$_2$—, e.g., methylene, dichloromethylene, dimethylmethylene, diphenylmethylene, etc., —C$_2$($R^2$)$_4$—, e.g., ethylene, tetrachloroethylene, tetramethylethylene, tetraethylethylene, dimethyldiphenylethylene, etc., —Si($R^2$)$_2$—, e.g., dichlorosilylene, dimethylsilylene, diethylsilylene, etc., and —Ge($R^2$)$_2$—, e.g., dichlorogermanylene, dimethylgermanylene, etc.

The transition metal atom M is selected from the group consisting of Ti, Zr and Hf.

The substituent $X^1$ for M is a hydrogen atom, a halogen atom, a similar hydrocarbon or halogenated hydrocarbon group as defined above for the substituent $R^1$, preferably a halogen atom, more preferably chlorine.

The metallocene compound of formula (1) wherein Z is $(CA^2)(R^1)_n(Ra)_q$ can be represented by the following formula (2)

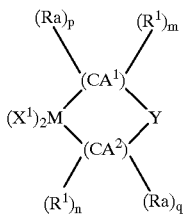

(2)

wherein each symbol has the meaning as defined above.

$CA^1$ and $CA^2$ in the formula may be identical or different. In addition to the identity of $CA^1$ with $CA^2$, the compound of the following formula (2A) wherein Z is $(Ra)_p(R^1)_m(CA^1)$ in said formula (1) shows high olefin polymerization activity excellent as the below-mentioned catalyst for olefin polymerization.

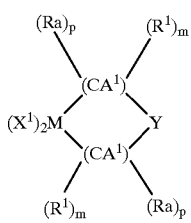

(2A)

wherein each symbol has the meaning as defined above. This compound includes a racemic form consisting of a stereostructurally unsymmetrical compound with respect to the plane containing M and its enantiomer, a meso form consisting of a stereostructurally symmetrical compound with respect to the plain containing M and the mixture thereof.

The metallocene compounds wherein concrete combination of $CA^1$ and $CA^2$ is specified are represented by the following formulas (2a) to (2g).

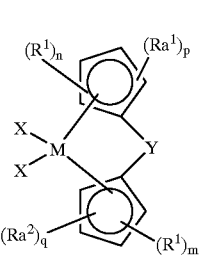

(2a)

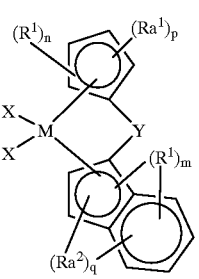

(2b)

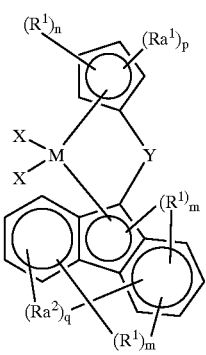

(2c)

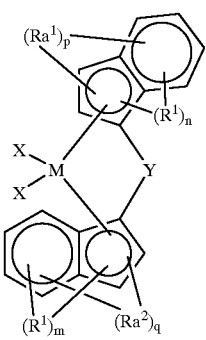

(2d)

-continued

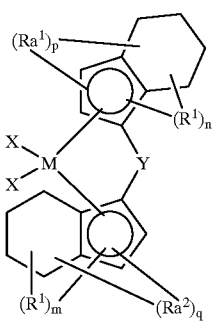

(2e)

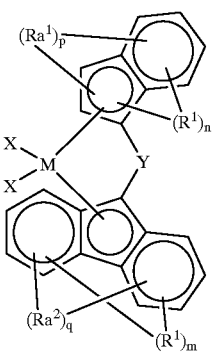

(2f)

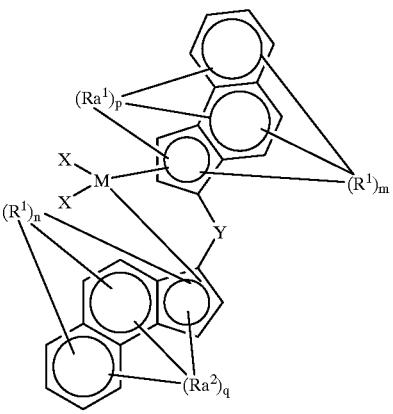

(2g)

Further, concrete examples of metallocene compounds represented by formula (2a) are shown in the attached Tables 2–9, concrete examples of metallocene compounds represented by formula (2d) are shown in the attached Tables 10–13, concrete examples of metallocene compounds represented by formula (2e) are shown in the attached Tables 14–17 and concrete examples of metallocene compounds represented by formula (2g) are shown in the attached Tables 18 and 19, by way of indicating concrete groups corresponding to each symbol in each formula and without distinction of the racemic and meso forms.

For instance, the compound denoted by Number 1 in Table 2 represents ethylenebis[2-(2-furyl)-cyclopentadienyl] [2'-(2-furyl)-cyclopentadienyl]zirconium dichloride, ethylenebis[2-(2-furyl)-cyclopentadienyl] [5'-(2-furyl)-cyclopentadienyl]zirconium dichloride and the mixture thereof. For the compounds wherein the substituent $R^1$ is present on both $CA^1$ and $CA^2$, they represent the compounds having the relationship of the racemic form and the meso form from a substitution position of each substituent $R^1$ on $CA^1$ and $CA^2$, and the mixture thereof.

The abbreviations used in Tables 2–19 are as follows:
Fu: furyl, MeFu: methyl furyl,
Thie: thienyl, Py: pyridyl,
BzFu: benzofuryl, 1-MePyr: 1-methylpyrrolyl,
Me: methyl, Et: ethyl,
i-Pr: isopropyl, t-Bu: tert-butyl,
Ph: phenyl, Np: naphthyl,
Tol: toluyl Bzl: benzyl,
OMe: methoxy, OPh: phenoxy,
OBzl: benzyloxy, TMS: trimethylsilyl,
Pyr: pyrrolyl, Indo: indolyl The combinations of $CA^1$ and $CA^2$ may be, in addition to the above, those of a substituted cyclopentadienyl group and a substituted tetrahydroindenyl group, a substituted cyclopentadienyl group and a substituted benzoindenyl group, a substituted indenyl group and a substituted tetrahydroindenyl group, a substituted indenyl group and a substituted benzoindenyl group, a substituted tetrahydroindenyl group and a substituted benzoindenyl group, a substituted tetrahydroindenyl group and a substituted fluorenyl group, a substituted benzoindenyl group and a substituted fluorenyl group.

The metallocene compounds of said formula (1) wherein Z is —$(R^1)N$—, —O—, —S— and —$(R^1)P$—, respectively are represented by the following formulas (3a)–(3d). Concrete examples of the compounds of formula (3a) are shown in the attached Tables 20 and 21, by way of indicating concrete groups corresponding to each symbol using the above abbreviations.

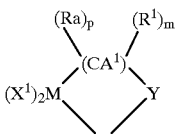

(3a)

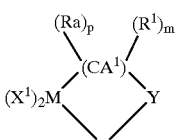

(3b)

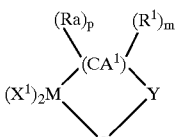

(3c)

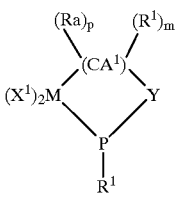

(3d)

The metallocene compounds of the present invention can be prepared by the following methods.

(a) A substituted cycloalkadiene anion represented by the following formula (4Aa)

$$(Ra)_p(R^1)_m(CA^1)^- \text{---} \qquad (4Aa)$$

wherein $CA^1$, Ra, $R^1$, p and m have respectively the meanings as defined above, is reacted with a binding agent represented by the following formula (5A), at a molar ratio of 2:1, $$X^2\text{---}Y\text{---}X^2 \qquad (5A)$$

wherein Y has the meaning as defined above and $X^2$ represents a hydrogen atom or a halogen atom, said anion being prepared by reacting a substituted cycloalkadiene represented by the following formula (4A)

$$(Ra)_p(R^1)_m(CA^1)H \qquad (4A)$$

with a metal salt type base to effect an anionization; or a substituted cycloalkadiene anion represented by said formula (4Aa) is reacted with any one of the compounds represented by the following formulas (5B) to (5F), at a molar ratio of 1:1, $$X^2\text{---}Y\text{---}(CA^2)(R^1)_n(Ra)_q \qquad (5B)$$

$$X^2\text{---}Y\text{---}(R^1)NH \qquad (5C)$$

$$X^2\text{---}Y\text{---}OH \qquad (5D)$$

$$X^2\text{---}Y\text{---}SH \qquad (5E)$$

$$X^2\text{---}Y\text{---}(R^1)PH \qquad (5F)$$

wherein Y, $CA^2$, Ra, $R^1$, n, q and $X^2$ have respectively the meanings as defined above, to form a compound represented by the following formula (6)

$$(Ra)_p(R^1)_m(CA^1)\text{---}Y\text{---}Z^1 \qquad (6)$$

wherein $Z^1$ represents $(CA^1)(R^1)_m(Ra)_p$, $(CA^2)(R^1)_n(Ra)_q$, $(R^1)$ NH, ---OH, ---SH or $(R^1)$PH.

(b) Subsequently, a dianion represented by the following formula (6A)

$$(Ra)_p(R^1)_m(CA^1)\text{---}Y\text{---}Z\text{---} \qquad (6A)$$

wherein each symbol has the meaning as defined above, is reacted with a transition metal compound represented by the following formula (7)

$$(X^1)_2\text{---}M\text{---}(X^3)_2 \qquad (7)$$

wherein M and $X^1$ have the meaning as defined above and $X^3$ represents hydrogen or a halogen atom, said dianion being prepared by reacting the compound represented by said formula (6) with a metal salt type base to anionize each of the cycloalkadienyl ring and $Z^1$, thus preparing the metallocene compound represented by said formula (1).

The compound represented by said formula (2A) can be prepared by reacting the substituted cycloalkadiene anion represented by said formula (4Aa) with the binding agent represented by said formula (5A) at a molar ratio of 2:1 to obtain a bis-substituted cyclopentadiene of formula (6) wherein $Z^1$ is $(CA^1)(R^1)_m(Ra)_p$ and subsequently conducting said (b) step.

The compounds represented by said formula (5B) can be prepared by reacting a substituted or unsubstituted cycloalkadiene anion represented by the following formula (4Ba)

$$(Ra)_q(R^1)_n(CA^2)^- \text{---} \qquad (4Ba)$$

with a binding agent represented by said formula (5A) at a molar ratio of 1:1, said anion being prepared by reacting a substituted or unsubstituted cycloalkadiene represented by the following formula (4B)

$$(Ra)_q(R^1)_n(CA^2)H \qquad (4B)$$

with a metal salt type base to carry out an anionization. The compound of said formula (5B) can produce the metallocene compounds of said formula (2) wherein $CA^1$ and $CA^2$ are different each other.

The compounds represented by formula (5c): $X^2\text{---}Y\text{---}(R^1)NH$ are secondary amines wherein Y is a hydrocarbon group, a silylene group, a germanium group or a stannyl group.

The compounds represented by formula (5d): $X^2\text{---}Y\text{---}OH$ are alcohols wherein Y is a hydrocarbon group, silanols wherein Y is a silylene group, germaniols wherein Y is a germanium group and stannyols wherein Y is a stannyl group.

The compounds represented by formula (5e): $X^2\text{---}Y\text{---}SH$ are thiols derived from the alcohols of said formula (5d) by replacing OH with ---SH.

The compounds represented by formula (Sf): $X^2\text{---}Y\text{---}(R^1)PH$ are secondary phosphines wherein Y is as defined above.

In these compounds represented by formulas (5b)–(5f), $X^2$ is preferably a halogen atom.

As the binding agents represented by said formula (5A) are recited the compounds wherein Y is a hydrocarbon group, e.g., dichlorodimethylmethane, dichlorodiethylmethane, dichloro-di-n-propylmethane, dichloro-di-n-butylmethane, dichlorodiphenylmethane, dibromodimethylmethane, dibromodiethylmethane, dibromo-di-n-propylmethane, dibromo-di-n-butylmethane, dibromodiphenylmethane, dichlorotetramethylethane, dibromotetraethylethane or the like; the compounds wherein Y is a silylene group, e.g., dichlorodimethylsilane, dichlorodiethylsilane, dichloro-di-n-propylsilane, dichloro-di-n-butylsilane, dichlorodiphenylsilane, dibromodimethylsilane, dibromodiethylsilane, dibromo-di-n-propylsilane, dibromo-di-n-butylsilane, dibromodiphenylsilane or the like; the compounds wherein Y is a germanium group, e.g., dichlorogermaniumdimethyl, dichlorogermaniumdiethyl, dichlorogermanium-di-n-propyl, dichlorogermanium-di-n-butyl, dichlorogermaniumdiphenyl, dibromogermaniumdimethyl, dibromogermaniumdiethyl, dibromogermanium-di-n-propyl, dibromogermanium-di-n-butyl, dibromogermaniumdiphenyl or the like; and similar compounds wherein Y is a stannyl group.

The substituted cycloalkadienes represented by said formulas (4A) and (4B) are substituted cyclopentadienes, substituted indenes, substituted tetrahydroindenes, substituted benzoindenes or substituted fluorenes wherein a hydrogen atom on the cycloalkadiene ring is substituted by a heteroaromatic group Ra and/or a substituent $R^1$.

These substituted cycloalkadienes can be prepared by reacting a heteroaromatic anion anionized by reacting a heteroaromatic compound with or without a halogen atom at the position bonding to the cycloalkadiene ring with a metal salt type base, with a cycloalken-one wherein a hydrogen atom on the cycloalkadiene ring to be substituted by the heteroaromatic group is substituted by an oxygen atom, thus converting into a keto form.

The transition metal compounds represented by said formula (7) are metal tetrahalide compounds, e.g., titanium tetrachloride, titanium tetrabromide, titanium tetraiodide, titanium tetrafluoride, titanium trichloride, titanium tribromide, titanium triiodide, titanium trifluoride, zirconium tetrachloride, zirconium tetrabromide, zirconium tetraiodide, zirconium tetrafluoride, hafnium tetrachloride, hafnium tetrabromide, hafnium tetraiodide, hafnium tetrafluoride or the like; metal tri- or di-halide compounds wherein up to two of the halogen atoms are substituted by said hydrocarbon group, halogenated hydrocarbon group or silyl group, preferably metal tetrahalide compounds.

In the above-described processes, the anionization of substituted cycloalkadienes sustitued by the heteroaromatic group and the dianionization of the bis- or di-substituted cycloalkadienes mean the anionization of each 5-membered ring, i.e., cyclopentadiene ring. The former permits a linkage of two molecules by reaction with a binding agent subsequent to anionization, and the latter permits an intramolecular linkage for ring closure by reaction with a transition metal compound subsequent to dianionization.

As the metal salt type bases used in the anionization of the cyclopentadiene and aromatic rings in each step of the above-mentioned processes are recited, for example, methyllithium, n-butyllithium, t-butyllithium, phenyllithium, lithium hydride, sodium hydride, potassium hydride, calcium hydride, lithium diisopropylamide, t-butyloxypotassium, methylmagnesium iodide, ethylmagnesium iodide, phenylmagnesium bromide, t-butylmagnesium bromide or the like.

The anionization reaction of substituted cycloalkadienes substituted by the heteroaromatic group and bis- or di-substituted cycloalkadienes can be carried out with said metal salt type base in the presence of an amine compound which includes primary amines, e.g. methylamine, ethylamine, n-propyl-amine, isopropylamine, n-butylamine, tert-butylamine, aniline, ethylenediamine or the like; secondary amines, e.g. dimethylamine, diethylamine, di-n-propylamine, diisopropylamine, di-n-butylamine, di-tert-butylamine, pyrrolidine, hexamethyldisilazane, diphenylamine or the like; and tertiary amines, e.g. trimethylamine, triethylamine, tri-n-propylamine, triisopropylamine, tri-n-butylamine, tri-tert-butylamine, triphenylamine, N,N-dimethylaniline, N,N,N',N'-tetramethylethylenediamine, N-methylpyrrolidine, 4-dimethylaminopyridine or the like.

Each of the above-mentioned reactions is usually carried out in an organic solvent at a reaction temperature between not lower than −100° C. and not higher than a boiling point of the solvent, preferably in the range of −70° C. to 100° C.

The solvents used in the reaction can be used without any limitation, if they are not reactive to the above starting compounds and reaction products and do not decompose them. Preferably, ethers, halogenated hydrocarbons or aromatic compounds are used. For ethers are preferable relatively low-molecular ethers such as diethylether, diisopropylether, tetrahydrofuran, dimethoxyethane or the like. Dichloromethane is preferable for halogenated hydrocarbons. For aromatic compounds are preferable toluene, anisol and xylene. Further, a mixed solvent of these two or more compounds can be used.

The synthesis of the metallocene compounds represented by said formula (2A) is mentioned below.

The bis-substituted cycloalkadiene prepared by reacting the substituted cycloalkadiene anion represented by said formula (4Aa) with the binding agent represented by formula (5A) is generally formed as a mixture of a racemic form consisting of a compound having a steric structure unsymmetrical with respect to Y and the enantiomer thereof and a compound having a steric structure symmetrical with respect to Y.

Usually, the resultant reaction mixture to which water has been added, is allowed to stand to separate into an organic layer and a water layer, thus obtaining the bis-substituted cycloalkadiene as an organic layer. The bis-substituted cycloalkadiene can be used as it is in the form of a resulting solution for the subsequent step, but usually used after separation from the solution. As the method of separating the bis-substituted cycloalkadiene from the solution can be employed, for example, the method wherein the solvent is distilled off. The separated cycloalkadiene is further purified by recrystallization, distillation, column chromatography or the like, and may be further separated into the racemic and meso forms, and each form may be further purified and used for the subsequent step.

The bis-substituted cycloalkadiene as prepared above is reacted with a metal salt type base to anionize each 5-membered ring, thereby forming the dianion represented by formula (4Ba), and then this bis-substituted cycloalkadiene dianion is reacted with the transition metal compound represented by formula (7) to achieve an intramolecular linkage for ring closure, thus forming a mixture of the racemic and meso forms of the metallocene compound represented by said formula (2A).

Finally, each of the racemic and meso forms of the metallocene compounds is isolated from the above-mentioned reaction solution in the usual way and purified to obtain the racemic and meso metallocene compounds. Isolation and purification of the racemic and meso metallocene compounds can be effected by distilling the solvent off, if necessary, extraction with a suitable solvent, adsorption, filtration, recrystallization or the like. Usually, each compound is crystallized out by utilizing the difference in solubility of the compound in a solvent and then purified by recrystallization or the like.

Figure 3A:
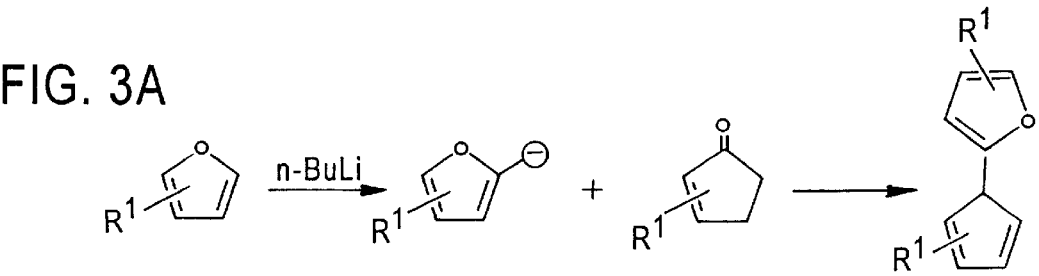
FIGS. 3A, 3B and 3C represent three reaction steps in the synthesis of the metallocene compounds according to the present invention.
Figure 3B:
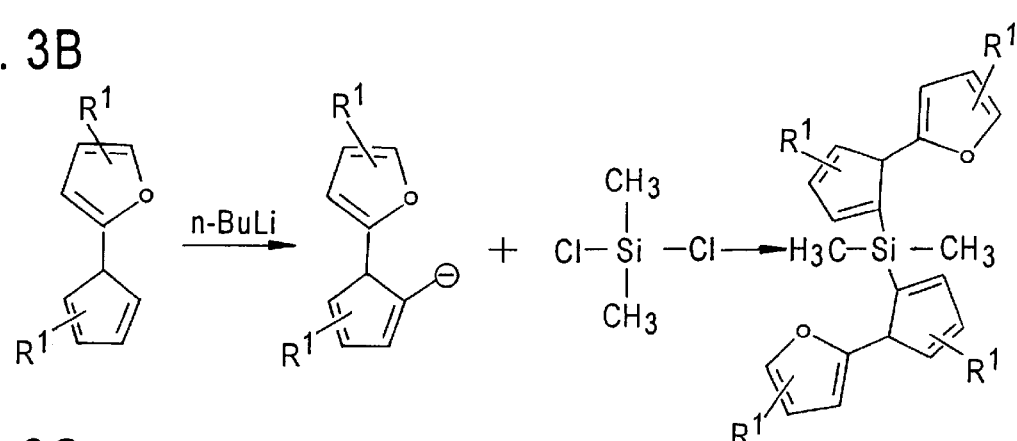
Figure 3C:
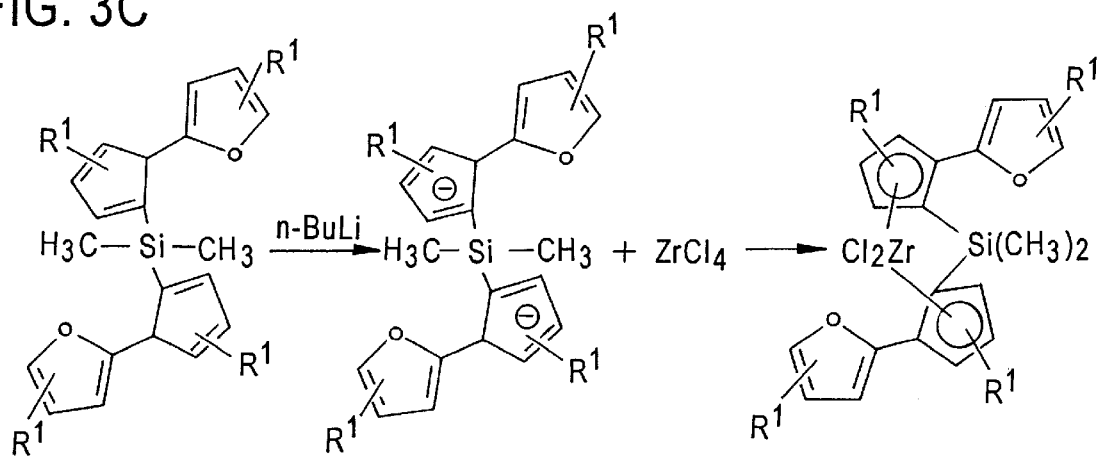

The scheme for the synthesis of dimethyl-silylenebis[2-(2-furyl)-3,5-dimethyl-cyclopentadienyl]-zirconium dichloride (Compound No. 94 in the attached Table 3), represented by said formula (2A) wherein $CA^1$ is a cyclopentadienyl ring substituted by furyl and two methyl groups, Y is dimethylsilylene, M is zirconium and $X^1$ is chlorine, is shown in the attached FIG. 3.

The catalysts for olefin polymerization of the present invention contain the metallocene compound represented by said formula (1) as a principal component. Preferably, the metallocene compounds represented by said formula (2), and more preferably, the metallocene compounds represented by said formula (2A) are used as the principal component.

The metallocene compounds represented by said formula (2A) may be the racemic or meso forms isolated in said processes for the preparation, or may be those separated from the solution and purified in the form of the mixture without isolation of each form.

Other components constituting the catalyst for polymerization of olefin in combination with said metallocene compounds can include one or more compounds which are generally used in the polyolefin polymerization, selected from, for example, an aluminoxane, an ionic compound which can react with a metallocene compound to form an ionic complex and Lewis acid.

The aluminoxane is an organoaluminum compound represented by the following formula (8) or (9):

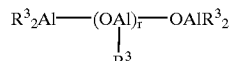  (8)

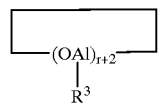  (9)

in which $R^3$ is a hydrocarbon group of 1–20 carbons, preferably 1–4 carbons and concretely represents methyl, ethyl, propyl, isopropyl, butyl, isobutyl, $R^3$ may be identical or different, and r is an integer of 1 to 1000, but said compound may be a mixture of aluminoxanes having different r values.

The ionic compounds are salts of cationic and anionic compounds. An anion has an action to cationize the metallocene compound by reaction therewith and to stabilize the cation species in the metallocene compound by formation of an ion pair. As such anions are recited the anions of organoboron compounds, organoaluminum compounds or the like. As the cations are recited metallic cations, organometallic cations, carbonium cations, tropium cations, oxonium cations, sulfonium cations, phosphonium cations, ammonium cations or the like. Of these, preferable are ionic compounds containing a boron atom as an anion. In the concrete, there are recited N,N-dimethylanilinium tetrakis(pentafluorophenyl)borate, trityltetrakis-(pentafluorophenyl)borate or the like.

For Lewis acid is preferable a boron-containing Lewis acid. In the concrete, there are recited tri(n-butyl)boron, triphenyl boron, tris[3,5-bis(trifluoromethyl)-phenyl]boron, tris[(4-fluoromethyl)phenyl]boron, tris(3,5-difluorophenyl)boron, tris(2,4,6-trifluorophenyl)boron, tris(pentafluorophenyl)boron or the like.

In addition to the above, known ionic compounds which can react with the metallocene compounds to form the ionic complexes and Lewis acids can be also used.

The proportion of the metallocene compounds and these catalyst components used is in such a range that the Al atom in the aluminoxane is 1–50,000 mols, preferably 50–20,000 mols per mol of the transition metal atom in the metallocene compound, when the aluminoxane is used as a catalyst component. When the ionic compound or Lewis acid is used as a catalyst component, the ionic compound or Lewis acid is in the range of 0.01–2,000 mols, preferably 0.1–500 mols, per mol of the transition metal atom in the metallocene compound.

In the present invention, another embodiment of the catalyst for olefin polymerization is composed of said metallocene compound, said aluminoxane and a support in the form of finely divided particles. Usually, each of the metallocene compound and the aluminoxane or a reaction product of the metallocene compound and the aluminoxane is used by supporting it on said support. As such supports are employed finely divided inorganic or organic solid particles in the form of granules or spheres, the particle size of which is in the range of 5–300 μm, preferably 10–200 μm.

For the inorganic supports are preferable metal oxides, e.g., $SiO_2$, $Al_2O_3$, MgO, $TiO_2$, ZnO or the like, or the mixture thereof. The supports containing as a principal component at least one selected from the group consisting of $SiO_2$, $Al_2O_3$ and MgO are especially preferable. More specifically, inorganic compounds can include $SiO_2$, $Al_2O_3$, MgO, $SiO_2$—$Al_2O_3$, $SiO_2$—MgO, $SiO_2$—$TiO_2$, $SiO_2$—$Al_2O_3$—MgO or the like. These inorganic oxide supports are usually calcined at a temperature of 100–1000° C. for 1–40 hrs.

The organic supports can include the polymers or copolymers of α-olefins of 2–12 carbons such as ethylene, propylene, 1-butene, 4-methyl-1-pentene or the like, and the polymers or copolymers of styrene or styrene derivatives.

The process for the production of an olefin polymer according to the present invention comprises polymerizing an olefin in the presence of said catalyst for olefin polymerization. Preferably, an olefin is polymerized in the presence of the catalyst for olefin polymerization formed from metallocene compounds, aluminoxanes and said supports as well as organoaluminum compounds.

The term "polymerization" in the present specification is used in the sense to include a homopolymerization and copolymerization. Thus, the term "olefin polymer" includes a homopolymer of one olefin and a copolymer of two or more olefins.

In the present invention, as the polymerizable olefins are recited straight-chain α-olefins such as ethylene, propylene, 1-butene, 1-hexene, 1-pentene, 1-decene, 1-dodecene, 1-tetradecene, 1-hexadecene, 1-octadecene, 1-eicosene or the like, branched-chain α-olefins such as 3-methyl-1-butene, 4-methyl-1-pentene, 2-methyl-1-pentene or the like, and the mixture of these two or more species.

The processes for the production of the olefin polymer according to the present invention can produce not only homopolymers of said olefins, but also random copolymers comprising e.g., a combination of two components such as ethylene/propylene, propylene/1-butene, a combination of three components such as ethylene/propylene/1-butene, block copolymers by varying kinds of olefins which feed in a multistage polymerization.

The polymerization of a cyclic olefin, a diene, a styrene and the derivatives thereof and other polymerizable monomers having a double bond or the copolymerization with an α-olefin can be carried out by use of the above-mentioned processes for the production of olefin polymers.

As the polymerizable cyclic olefins are recited, for example, cyclobutene, cyclopentene, cyclohexene, cycloheptene, norbornene, 5-methyl-2-norbornene, 5-ethyl-2-norbornene, phenylnorbornene, indanylnorbornene or the like. As the dienes are recited, for example, cyclic dienes such as 5-methylene-2-norbornene, 5-ethylidene-2-norbornene, 5-propylidene-5-norbornene, dicyclopentadiene, 5-vinyl-2-norbornene or the like, and acyclic dienes such as 1,3-butadiene, isoprene, 1,4-hexadiene, 4-methyl-1,4-hexadiene, 5-methyl-1,4-hexadiene, 5-methyl-1,5-heptadiene, 6-methyl-1,5-heptadiene, 1,7-octadiene, 6-methyl-1,7-octadiene, 7-methyl-1,6-octadiene, 1,8-nonadiene, 1,9-decadiene or the like. As the styrenes and the derivatives thereof are recited, for example, styrene, p-chlorostyrene, p-methylstyrene, p-tert-butylstyrene, α-methylstyrene, vinylnaphthalene or the like. As other polymerizable monomers having a double bond are recited, for example, vinylcyclohexane, vinyl chloride, 4-trimethylsiloxy-1,6-heptadiene, 5-(N,N-diisopropylamino)-1-pentene, methylmethacrylate, ethylacrylate or the like.

The organoaluminum compounds coexistent with the olefin polymerization catalyst in the olefin polymerization system are triethylaluminum, triisopropylaluminum, triisobutylaluminum, tri-n-butylaluminum, tri-n-hexylaluminum, diisobutylaluminum hydride or the like and the mixture thereof, and triethylaluminum and triisobutylaluminum are preferably used.

In the processes for the production of olefin polymers according to the present invention, both of a liquid-phase polymerization and a vapor-phase polymerization can be employed as a process for the polymerization of olefins. In the liquid-phase polymerization, an inert hydrocarbon may be a solvent, and further a liquid olefin itself such as a liquid propylene, a liquid 1-butene or the like can be used as a solvent. As the solvents for polymerization are recited an aromatic hydrocarbon such as benzene, toluene, ethylbenzene, xylene or the like, an aliphatic hydrocarbon such as butane, isobutane, pentane, hexane, heptane, octane, decane, dodecane, hexadecane, octadecane or the like, an alicyclic hydrocarbon such as cyclopentane, methylcyclopentane, cyclohexane, cyclooctane or the like and a petroleum cut such as gasoline, kerosene, gas oil or the like.

The polymerization process may employ either of batch-wise, semi-continuous and continuous methods. Further, the polymerization may be carried out in two or more stages divided by changing the reaction conditions.

The metallocene compounds used in said polymerization process, particularly the metallocene compounds of said formula (2A) may be either of an isolated racemic or meso form, or the separated and purified mixture thereof. In particular, the isolated racemic form achieves an extremely great effect in making the molecular weight of the produced polypropylene higher.

The concentration of the metallocene compound within the polymerization reaction system, with no particular limitation thereon, is preferably in the range of $10^{-2}$–$10^{-10}$ mol/l based on the transition metal.

The pressure of olefins in the polymerization reaction system, with no particular limitation thereon, is preferably in the range of normal pressure to 50 kg/cm$^2$. Further, the polymerization temperature, with no particular limitation thereon, is usually in the range of −50 to 250° C., preferably −30 to 100° C. The regulation of the molecular weight upon the polymerization can be effected by known means, for example, choice of the temperature or introduction of hydrogen.

The olefin polymers produced by the above-mentioned processes are provided for various forming or molding materials, through conventional process steps such as the deactivation treatment of catalyst, the treatment for catalyst residue, drying or the like.

EXAMPLE

Example 1

Synthesis of dimethylsilylenebis[3-(2-furyl)-2,5-dimethyl-cyclopentadienyl]zirconium dichloride (Compound No. 254)

(a1) Synthesis of 1-(2-furyl)-2,4-dimethylcyclopentadiene

A 500 ml glass reaction vessel was charged with 9.4 g (0.14 mol) of furan and 150 ml of tetrahydrofuran (THF) and cooled to −20° C. on a dry ice/methanol bath. To the mixture were added dropwise 90 ml (0.14 mmol) of an n-butyllithium/hexane solution of 1.54 mol/l. After the addition was completed, the mixture was raised to room temperature and stirred for 6 hrs. The mixture was again cooled to −20° C. on a dry ice/methanol bath and 30 ml of a THF solution containing 15.2 g (0.14 mol) of 2,4-dimethyl-cyclopenten-1-one were added dropwise. After the addition was completed, the mixture was raised to room temperature and stirred for 16 hrs.

The reaction solution was cooled to −20° C. on a dry ice/methanol bath and 10 ml of 2N-hydrochloric acid were added dropwise. This reaction solution was transferred into a separatory funnel and washed with a brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 20.3 g (92% yield) of a yellow liquid of 1-(2-furyl)-2,4-dimethylcyclopenta-diene. The structure was identified by NMR.

(a2) Synthesis of dimethylbis[3-(2-furyl)-2,5-dimethyl-cyclopentadienyl] silane

A 500 ml glass reaction vessel was charged with 20.3 g (0.13 mol) of 1-(2-furyl)-2,4-dimethylcyclopentadiene and 130 ml of THF and cooled to −30° C. on a dry ice/methanol bath. To the mixture were added dropwise 85 ml (0.13 mmol) of an n-butyllithium/hexane solution of 1.54 mol/l. After the addition was completed, the mixture was raised to room temperature and stirred for 16 hrs. The mixture was again cooled to −30° C. on a dry ice/methanol bath and 30 ml of a THF solution containing 8.2 g (0.064 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with a brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 7.7 g (33% yield) of dimethylbis[3-(2-furyl)-2,5-dimethyl-cyclopentadienyl] silane as a yellow liquid. The structure was identified by NMR.

(b) Synthesis of dimethylsilylenebis[3-(2-furyl)-2,5-dimethylcyclopentadienyl]zirconium dichloride A 100 ml glass reaction vessel was charged with 2.0 g (0.050 mol) of potassium hydride (KH) and 40 ml of THF and cooled to −70° C. on a dry ice/methanol bath. To the mixture were added dropwise 40 ml of a THF solution containing 7.7 g (0.021 mol) of dimethylbis[3-(2-furyl)-2, 5-dimethylcyclopentadienyl] silane as synthesized above. After the addition was completed, the mixture was returned to room temperature and stirred for 16 hrs. The reaction solution was allowed to stand and a supernatant solution was transferred into a 100 ml glass reaction vessel. The solvent in the supernatant solution was distilled off under reduced pressure, 15 ml of dichloromethane were added, and the reaction solution was solidified with liquid nitrogen, to which were added 45 ml of a dichloromethane suspension containing 6.2 g (0.027 mol) of tetrachlorozirconium. Subsequently, the mixture was raised to room temperature and stirred for 16 hrs. A part of the reaction solution was withdrawn and determined by $^1$H-NMR, by which it was found to be a mixture of a racemic form/meso form (molar ratio=58/42).

The solvent was distilled off under reduced pressure, the residue was extracted with hexane and recrystallized from toluene/hexane to obtain 90 mg (0.8% yield) of dimethylsilylenebis[3-(2-furyl)-2,5-dimethyl-cyclopentadienyl]zirconium dichloride (racemic form/meso form (molar ratio)=49/51).

¹H-NMR (CDCl₃)

Racemic form δ: 1.04 (s, 6H), δ: 2.24 (s, 6H), δ: 2.31 (s, 6H), δ: 6.47 (m, 4H), δ: 7.06 (s, 2H), δ: 7.44 (dd, 2H), Meso form δ: 1.04 (s, 3H), δ: 1.06 (s, 3H), δ: 2.23 (s, 6H), δ: 2.35 (s, 6H), δ: 6.42 (d, 4H), δ: 6.94 (s, 2H), δ: 7.41 (t, 2H).

Example 2

Synthesis of dimethylsilylenebis[2-(2-furyl)-3,5-dimethyl-cyclopentadienyl]zirconium dichloride (Compound No. 94)

(b) Synthesis of dimethylsilylenebis[2-(2-furyl)-3,5-dimethylcyclopentadienyl]zirconium dichloride A 100 ml glass reaction vessel was charged with 3.98 g (0.011 mol) of dimethylsilylenebis[2-(2-furyl)-4,5-dimethylcyclopentadienyl] silane synthesized by a similar procedure as in step (a) of Example 1 and 30 ml of THF, and cooled to −30° C. on a dry ice/methanol bath. To the mixture were added dropwise 15 ml (0.023 mmol) of an n-butyllithium/hexane solution of 1.52 mol/l. After the addition was completed, the mixture was raised to room temperature and stirred for 16 hrs. The solvent in the reaction solution was distilled off under reduced pressure, 10 ml of dichloromethane were added, and the reaction solution was solidified with liquid nitrogen, to which were added 30 ml of a dichloromethane suspension containing 2.5 g (0.011 mol) of tetrachloro-zirconium. Subsequently, the mixture was raised to room temperature and stirred for 16 hrs. A part of the reaction solution was withdrawn and determined by ¹H-NMR, by which it was found to be a racemic form/meso form (molar ratio=77/23).

The solvent was distilled off under reduced pressure and the residue was extracted with hexane to afford 2.3 g of dimethylsilylenebis[2-(2-furyl)-3,5-dimethyl-cyclopentadienyl]zirconium dichloride (racemic form/meso form (molar ratio)=78/22, yield 40.6%). Recrystallization gave 140 mg of the racemic form (purity 99% or more).

Figure 2:
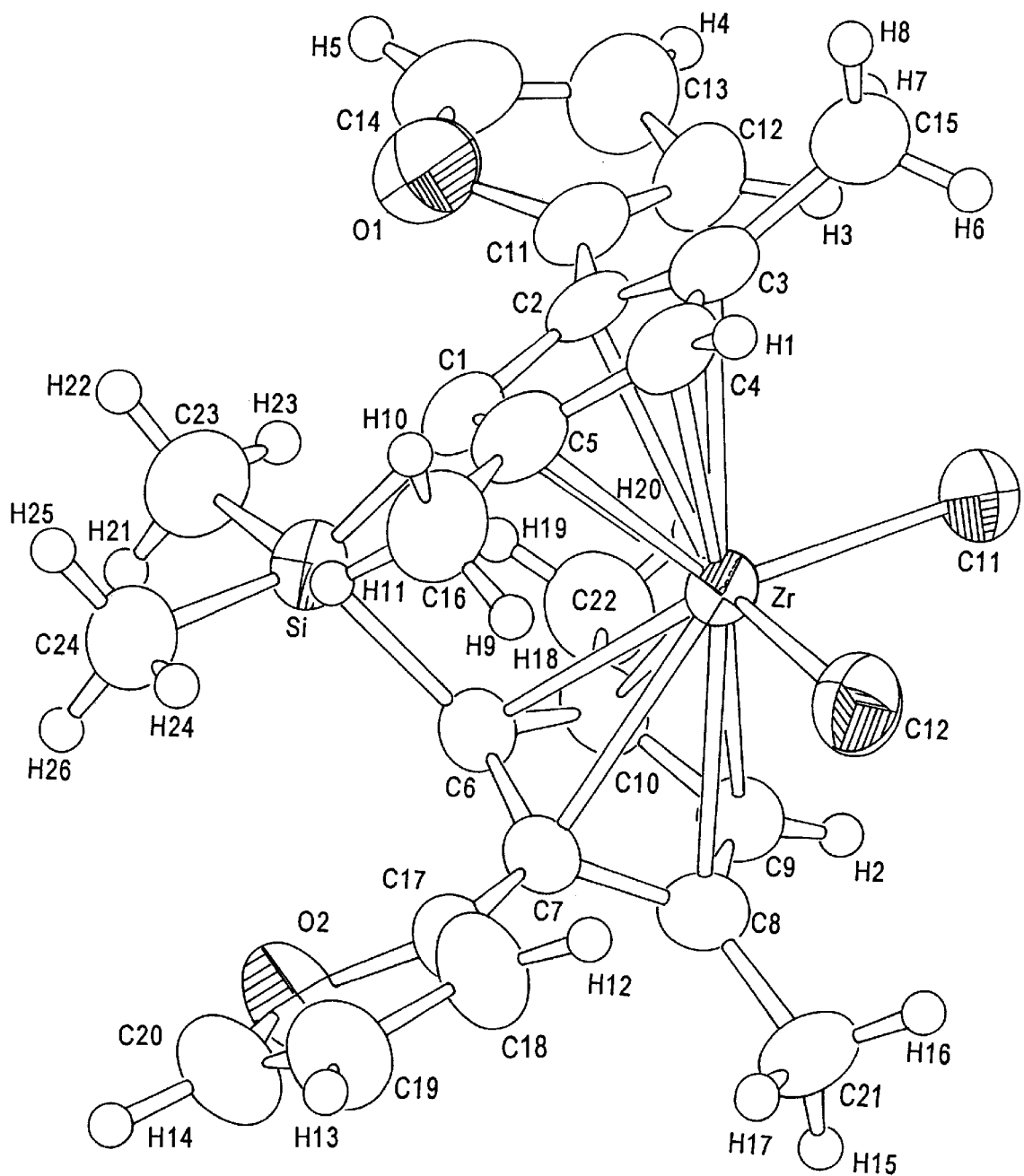
FIG. 2 is an ORTEP diagram obtained from a single crystal, X-ray structural analysis of compound No. 94 synthesized in Example 2, rac-dimethylsilylenebis[2-(2-furyl)-3,5-dimethyl-cyclopentadienyl]zirconium dichloride.

The ORTEP diagram of the resultant rac-dimethylsilylenebis[2-(2-furyl)-3,5-dimethyl-cyclopentadienyl]zirconium dichloride is shown in FIG. 2.

¹H-NMR (CDCl₃)

Racemic form δ: 0.62 (s, 6H), δ: 1.66 (s, 6H), δ: 2.27 (s, 6H), δ: 6.38 (dd, 2H), δ: 6.44 (dd, 2H), δ: 6.59 (s, 2H), δ: 7.42 (dd, 2H)

Meso form δ: 0.18 (s, 3H), δ: 1.06 (s, 3H), δ: 2.26 (s, 6H), δ: 2.36 (s, 6H), δ: 5.94 (dd, 2H), δ: 6.14 (dd, 2H), δ: 6.50 (s, 2H), δ: 7.14 (dd, 2H).

Example 3

Synthesis of dimethylsilylenebis[2-(2-furyl)-4,5-dimethyl-cyclopentadienyl]zirconium dichloride (Compound No. 95)

(a1) Synthesis of 1-(2-furyl)-3,4-dimethyl-cyclopentadiene

A 1 l glass reaction vessel was charged with 21.0 g (0.31 mol) of furan and 400 ml of diethyl ether and cooled to −30° C. on a dry ice/methanol bath. To the mixture were added dropwise 200 ml (0.31 mmol) of an n-butyllithium/hexane solution of 1.53 mol/l. After the addition was completed, the mixture was raised to room temperature and stirred for 4 hrs. The mixture was again cooled to −30° C. on a dry ice/methanol bath and 100 ml of a diethyl ether solution containing 33.0 g (0.30 mol) of 3,4-dimethyl-cyclopenten-1-one were added dropwise. After the addition was completed, the mixture was returned to room temperature and stirred for 16 hrs.

To the reaction solution was added distilled water, this solution was transferred into a separatory funnel and washed three times with brine. Subsequently, the solution was shaken twice with 50 ml of 5N hydrochloric acid and washed with a brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 24.6 g (51% yield) of 1-(2-furyl)-3,4-dimethyl-cyclopentadiene as a red liquid. The structure was identified by NMR.

(a2) Synthesis of dimethlbis[2-(2-furyl)-4,5-dimethyl-cyclopentadienyl] silane

A 1 l glass reaction vessel was charged with 24.3 g (0.15 mol) of 1-(2-furyl)-3,4-dimethylcyclopentadiene and 300 ml of THF and cooled to −30° C. on a dry ice/methanol bath. To the mixture were added dropwise 100 ml (0.15 mmol) of a n-butyllithium/hexane solution of 1.52 mol/l. After the addition was completed, the mixture was raised to room temperature and stirred for 3 hrs. The mixture was again cooled to −30° C. on a dry ice/methanol bath and 50 ml of of a THF solution containing 9.8 g (0.076 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column and recrystallization with toluene/hexane gave 19.4 g (68% yield) of dimethyl bis[2-(2-furyl)-4,5-dimethyl-cyclopentadienyl] silane as yellow crystals.

(b) Synthesis of dimethylsilylenebis[2-(2-furyl)-4,5-dimethyl-cyclopentadienyl]zirconium dichloride A 500 ml glass reaction vessel was charged with 10.0 g (0.027 mol) of dimethylbis[2-(2-furyl-)-4,5-dimethyl-cyclopentadienyl] silane and 200 ml of THF and cooled to −30° C. on a dry ice/methanol bath. To the mixture was added dropwise 35 ml (0.053 mmol) of an n-butyllithium/hexane solution of 1.52 mol/l. After the addition was completed, the mixture was raised to room temperature and stirred for 16 hrs. The solvent was distilled off under reduced pressure, 200 ml of toluene were added, and the solution was cooled to −70° C. on a dry ice/methanol bath. To the solution, 6.2 g (0.027 mol) of tetrachlorozirconium were added as it was solid. Subsequently, the mixture was raised to room temperature, stirred for 16 hrs. and heated at 80° C. for 4 hrs. A part of the reaction solution was withdrawn and determined by ¹H-NMR, by which it was found to be a racemic form/meso form (molar ratio=61/39).

The solvent was distilled off under reduced pressure and the residue was extracted with hexane to afford 2.5 g of dimethylsilylenebis[2-(2-furyl)-4,5-dimethyl-cyclopentadienyl]zirconium dichloride (racemic form/meso form=58/42, 17.5% yield) as yellow powders. Further recrystallization gave 120 mg of the racemic form (purity 99% or more) and 170 mg of the meso form (purity 99% or more).

¹H-NMR (CDCl₃) (See, FIG. 1)

Racemic form δ: 0.79 (s, 6H), δ: 1.45 (s, 6H), δ: 2.19 (s, 6H), δ: 6.41 (dd, 2H), δ: 6.55 (dd, 2H), δ: 6.72 (s, 2H), δ: 7.39 (dd, 2H)

Meso form δ: 0.62 (s, 3H), δ: 1.00 (s, 3H), δ: 2.02 (s, 6H), δ: 2.29 (s, 6H), δ: 6.12 (d, 4H), δ: 6.65 (d, 2H), δ: 7.13 (t, 2H).

Example 4

Synthesis of dimethylsilylenebis[3-(2-thienyl)-2,5-dimethyl-cyclopentadienyl]zirconium dichloride (Compound No. 274)

(a1) Synthesis of 1-(2-thienyl)-2,4-dimethyl-cyclopentadiene

A 200 ml glass reaction vessel was charged with 5.3 g (0.063 mol) of thiophene and 60 ml of THF and cooled to −10° C. on a dry ice/methanol bath. To the mixture were added dropwise 41 ml (0.064 mmol) of a n-butyllithium/hexane solution of 1.56 mol/l. After the addition was completed, the mixture was raised to room temperature and stirred for one hour. The mixture was again cooled to −20° C. on a dry ice/methanol bath and 30 ml of a THF solution containing 7.0 g (0.064 mol) of 2,4-dimethyl-cyclopenten-1-one were added dropwise. After the addition was completed, the mixture was raised to room temperature and stirred for 16 hrs.

The reaction solution was cooled to −20° C. on a dry ice/methanol bath and 7 ml of 2N-hydrochloric acid were added dropwise. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 9.7 g (87% yield) of a yellow-orange liquid of 1-(2-thienyl)-2,4-dimethyl-cyclopentadiene. The structure was identified by NMR.

(a2) Synthesis of dimethylbis[3-(2-thienyl)-2,5-dimethyl-cyclopentadienyl] silane A 100 ml glass reaction vessel was charged with 3.53 g (0.020 mol) of 1-(2-thienyl)-2,4-dimethyl-cyclopentadiene as synthesized above and 40 ml of THF and cooled to −30° C. on a dry ice/methanol bath. To the mixture were added dropwise 14 ml (0.022 mmol) of an n-butyllithium/hexane solution of 1.56 mol/l. After the addition was completed, the mixture was raised to room temperature and stirred for 16 hrs. The mixture was again cooled to −30° C. on a dry ice/methanol bath and 20 ml of a THF solution containing 1.3 g (0.010 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 1.3 g (16% yield) of a yellow liquid of dimethylbis[3-(2-thienyl)-2,5-dimethyl-cyclopentadienyl] silane. The structure was identified by NMR.

(b) Synthesis of dimethylsilylenebis[3-(2-thienyl)-2,5-dimethyl-cyclopentadienyl]zirconium dichloride A 100 ml glass reaction vessel was charged with 0.4 g (0.010 mol) of potassium hydride (KH) and 30 ml of THF and cooled to −70° C. on a dry ice/methanol bath. To the mixture were added dropwise 20 ml of a THF solution containing 1.2 g (0.0030 mol) of dimethylbis[3-(2-thienyl)-2,5-dimethyl-cyclopentadienyl] silane as synthesized above. After the addition was completed, the mixture was raised to room temperature and stirred for 16 hrs. The reaction solution was allowed to stand and a supernatant solution was transferred into a 100 ml glass reaction vessel. The solvent in the supernatant solution was distilled off under reduced pressure, 15 ml of dichloromethane were added, and the reaction solution was solidified with liquid nitrogen, to which were added 45 ml of a dichloromethane suspension containing 0.7 g (0.0031 mol) of tetrachlorozirconium. Subsequently, the mixture was raised to room temperature and stirred for 16 hrs. A part of the reaction solution was withdrawn and determined by $^1$H-NMR, by which it was found to be a racemic form/meso form (molar ratio=55/45).

The solvent was distilled off under reduced pressure, the residue was extracted with hexane and recrystallized with toluene/hexane to obtain 30 mg (2% yield) as yellow crystals of dimethylsilylenebis[3-(2-thienyl)-2,5-dimethyl-cyclopentadienyl)zirconium dichloride (racemic form/meso form (molar ratio)=60/40).

$^1$H-NMR (CDCl$_3$)

Racemic form δ: 1.05 (s, 6H), δ: 2.25 (s, 6H), δ: 2.35 (s, 6H), δ: 6.99 (s, 2H), δ: 7.09 (dd, 2H), δ: 7.20 (dd, 2H), δ: 7.30 (dd, 2H)

Meso form δ: 1.05 (s, 3H), δ: 1.06 (s, 3H), δ: 2.26 (s, 6H), δ: 2.36 (s, 6H), δ: 6.87 (s, 2H), δ: 7.05 (dd, 2H), δ: 7.19 (dd, 2H), δ: 7.26 (dd, 2H).

Example 5

Synthesis of dimethylsilylenebis[2-(2-furyl)-indenyl]-zirconium dichloride (Compound No. 424)

(a1) Synthesis of 2-(2-furyl)-indene

A 500 ml glass reaction vessel was charged with 4.7 g (0.069 mol) of furan and 100 ml of THF and cooled to −50° C. on a dry ice/methanol bath. To the mixture were added dropwise 48 ml (0.073 mmol) of an n-butyllithium/hexane solution of 1.52 mol/l. After the addition was completed, the mixture was raised to room temperature and stirred for 3 hrs. The mixture was again cooled to −30° C. on a dry ice/methanol bath and 100 ml of a THF solution containing 9.1 g (0.069 mol) of 2-indanone were added dropwise. After the addition was completed, the mixture was raised to room temperature and stirred for 16 hrs.

The reaction solution was cooled to −20° C. on a dry ice/methanol bath and 10 ml of 2N-hydrochloric acid were added dropwise. This reaction solution was transferred into a separatory funnel and washed with a brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 3.2 g (25% yield) of 2-(2-furyl)-indene as colorless crystals. The structure was identified by NMR.

(a2) Synthesis of dimethylbis[2-(2-furyl)-indenyl] silane

A 200 ml glass reaction vessel was charged with 1.3 g (0.0070 mol) of 2-(2-furyl)-indene as synthesized above, 0.09 g (0.001 mol) of copper cyanide and 30 ml of THF and cooled to −50° C. on a dry ice/methanol bath. To the mixture were added dropwise 5.2 ml (0.0079 mmol) of an n-butyllithium/hexane solution of 1.52 mol/l. After the addition was completed, the mixture was raised to room temperature and stirred for 16 hrs. The mixture was again cooled to −50° C. on a dry ice/methanol bath and 20 ml of THF solution containing 0.5 g (0.0039 mol) of dimethyl dichlorosilane were added dropwise. After the addition was completed, the mixture was raised to room temperature and stirred for 16 hrs.

To the reaction solution was added distilled water. This reaction solution was transferred into a separatory funnel and washed with brine until it was neutral. Anhydrous sodium sulfate was added and the solution was allowed to stand overnight and dried. Anhydrous sodium sulfate was filtered off and the solvent was distilled off under reduced pressure. Purification of the residue with a silica gel column gave 1.1 g (72% yield) of dimethylbis[2-(2-furyl)-indenyl] silane as light green crystals.

(b) Synthesis of dimethylsilylenebis[2-(2-furyl)-indenyl]-zirconium dichloride

A 100 ml glass reaction vessel was charged with 1.1 g (0.0025 mol) of dimethylbis[2-(2-furyl)-indenyl] silane as synthesized above and 30 ml of THF and cooled to −50° C. on a dry ice/methanol bath. To the mixture were added dropwise 3.6 ml (0.0055 mmol) of an n-butyllithium/hexane solution of 1.52 mol/l. After the addition was completed, the mixture was raised to room temperature and stirred for 16 hrs. The solvent in the reaction solution was distilled off under reduced pressure, 10 ml of dichloromethane were added, and the reaction solution was solidified with liquid nitrogen, to which were added 30 ml of a dichloromethane suspension containing 0.6 g (0.0026 mol) of tetrachloro-zirconium. Subsequently, the mixture was raised to room temperature and stirred for 16 hrs. A part of the reaction solution was withdrawn and determined by $^1$H-NMR, by which it was found to be dimethylsilylenebis[2-(2-furyl)-indenyl]-zirconium dichloride (racemic form/meso form (molar ratio=75/25).

The solvent was distilled off under reduced pressure, the residue was extracted with toluene and recrystallized with toluene to obtain 140 mg (10% yield) of a racemic form (purity 99% or more) of dimethylsilylenebis-[2-(2-furyl)-indenyl) zirconium dichloride.
$^1$H-NMR (CDCl$_3$)

Racemic form δ: 1.11 (s, 6H), δ: 6.41 (dd, 2H), δ: 6.48 (dd, 2H), δ: 6.72 (m, 2H), δ: 6.89 (m, 2H), δ: 6.97 (s, 2H), δ: 7.33 (m, 2H), δ: 7.52 (dd, 2H), δ: 7.55 (m, 2H).

Example 6

Polymerization of propylene

A SUS autoclave was charged with 1 liter of toluene and a toluene solution of methylaluminoxane (MMAO3A, manufactured by Toso-Aczo Co. Ltd.) in an amount equivalent to Al/Zr (molar ratio)=101000, to which was added separately each solution containing in 3 ml of a toluene solution, 1.35×10$^{-6}$ mol of the metallocene compound of Compound No. 254 (racemic form/meso form (molar ratio)= 49/51) synthesized in Example 1, 0.62×10$^{-6}$ mol of the metallocene compound of Compound No. 94 (racemic form 99%) synthesized in Example 2, 0.55×10$^{-6}$ mol of the metallocene compound of Compound No. 95 (racemic form 99%) synthesized in Example 3, 1.61×10$^{-6}$ mol of the metallocene compound of Compound No. 274 (racemic form/meso form (molar ratio)=60/40) synthesized in Example 4, and 0.30×10$^{-6}$ mol of the metallocene compound of Compound No. 424 (racemic form 99%) synthesized in Example 5, respectively, and each mixture was heated to 30° C. Into the autoclave was introduced propylene at a pressure of 0.3 MPa and a polymerization was carried out for one hour. After the polymerization was completed, a polymer was filtered and a catalyst component was decomposed with 1 liter of hydrochloric acidic methanol. Subsequently, filtration, washing and drying were carried out in order to obtain a polypropylene in an amount of 43.1 g, 42.7 g, 20.9 g, 33.6 g and 4.6 g, respectively.

The analytical values for the resultant polypropylene are shown in Table 1.

TABLE 1

| | Analytical Values for Polypropylene | | | | | | |
|---|---|---|---|---|---|---|---|
| Metallocene compound | Amount of Zr ×10$^{-6}$ mol | Yield g | Activity kg-pp/ mmol -M-h | Mw ×10$^4$ | Mw/Mn | Tm ° C. | Mmmm |
| 1 Me$_2$Si | 1.35 | 43.1 | 67 | 13.3 | 1.77 | 153.6 | 0.941 |
| 2 Me$_2$Si(2-Furyl-3,5-Me$_2$-Cp)$_2$ZrCl$_2$ | 0.62 | 42.7 | 69 | 48.3 | 1.91 | 156.9 | 0.956 |
| 3 Me$_2$Si(2-Furyl-4,5-Me$_2$-Cp)$_2$ZrCl$_2$ | 0.55 | 20.9 | 38 | 47.8 | 2.01 | 154.0 | 0.943 |
| 4 Me$_2$Si(3-Thienyl-3,5-Me$_2$-Cp)$_2$ZrCl$_2$ | 1.61 | 33.6 | 35 | 23.8 | 1.77 | 148.9 | 0.938 |
| 5 Me$_2$Si (3-Furyl-3,5-Me$_2$-Cp)$_2$ZrCl$_2$ | 0.30 | 4.6 | 15 | 128 | 2.30 | 148.0 | 0.925 |

TABLE 2

| | | | CA$^1$: Cyclopentadiene | | | CA$^2$: Cyclopentadiene | | | |
|---|---|---|---|---|---|---|---|---|---|
| No. | M | X | Ra | R$^1$ | p + m | Ra | R$^1$ | q + n | Y |
| 1 | Zr | Cl | 2-(2-Fu) | — | 1 | 2-(2-Fu) | — | 1 | —CH$_2$— |
| 2 | Zr | Cl | 2-(2-Fu) | — | 1 | 2-(2-Fu) | — | 1 | —C(Me)$_2$— |
| 3 | Zr | Cl | 2-(2-Fu) | 5-Me | 2 | 2-(2-Fu) | 5-Me | 2 | —C(Me)$_2$— |
| 4 | Zr | Cl | 2-(2-Fu) | 4-Me | 2 | 2-(2-Fu) | 4-Me | 2 | —C(Me)$_2$— |
| 5 | Zr | Cl | 2-(2-Fu) | 4-OMe | 2 | 2-(2-Fu) | 4-OMe | 2 | —C(Me)$_2$— |
| 6 | Zr | Cl | 2-(2-Fu) | 4-OPh | 2 | 2-(2-Fu) | 4-OPh | 2 | —C(Me)$_2$— |
| 7 | Zr | Cl | 2-(2-Fu) | 4-Bzl | 2 | 2-(2-Fu) | 4-Bzl | 2 | —C(Me)$_2$— |
| 8 | Zr | Cl | 2-(2-Fu) | 4-Tol | 2 | 2-(2-Fu) | 4-Tol | 2 | —C(Me)$_2$— |
| 9 | Zr | Cl | 2-(2-Fu) | 4-OBzl | 2 | 2-(2-Fu) | 4-OBzl | 2 | —C(Me)$_2$— |
| 10 | Zr | Cl | 2-(2-Fu) | 4-TMS | 2 | 2-(2-Fu) | 4-TMS | 2 | —C(Me)$_2$— |
| 11 | Zr | Cl | 2-(2-Fu) | 4-(1-Pyr) | 2 | 2-(2-Fu) | 4-(1-Pyr) | 2 | —C(Me)$_2$— |

TABLE 2-continued

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 12 | Zr | Cl | 2-(2-Fu) | 4-(1-Indo) | 2 | 2-(2-Fu) | 4-(1-Indo) | 2 | —C(Me)$_2$— |
| 13 | Zr | Cl | 2-(2-Fu) | 3-Me | 2 | 2-(2-Fu) | 3-Me | 2 | —C(Me)$_2$— |
| 14 | Zr | Cl | 2-(2-Fu) | 3-Me, 5-Me | 3 | 2-(2-Fu) | 3-Me, 5-Me | 3 | —C(Me)$_2$— |
| 15 | Zr | Cl | 2-(2-Fu) | 4-Me, 5-Me | 3 | 2-(2-Fu) | 4-Me, 5-Me | 3 | —C(Me)$_2$— |
| 16 | Zr | Cl | 2-(2-Fu) | 4-Et, 5-Me | 3 | 2-(2-Fu) | 4-Et, 5-Me | 3 | —C(Me)$_2$— |
| 17 | Zr | Cl | 2-(2-Fu) | 4-(i-Pr), 5-Me | 3 | 2-(2-Fu) | 4-(i-Pr), 5-Me | 3 | —C(Me)$_2$— |
| 18 | Zr | Cl | 2-(2-Fu) | 4-(t-Bu), 5-Me | 3 | 2-(2-Fu) | 4-(t-Bu), 5-Me | 3 | —C(Me)$_2$— |
| 19 | Zr | Cl | 2-(2-Fu) | 4-Ph, 5-Me | 3 | 2-(2-Fu) | 4-Ph, 5-Me | 3 | —C(Me)$_2$— |
| 20 | Zr | Cl | 2-(2-Fu) | 3-Ph, 5-Me | 3 | 2-(2-Fu) | 3-Ph, 5-Me | 3 | —C(Me)$_2$— |
| 21 | Zr | Cl | 2-(2-Fu) | 4-Me, 5-Me | 3 | 2-(2-Fu) | 4-Me, 5-Me | 3 | —C(Me)$_2$— |
| 22 | Zr | Cl | 2-(2-Fu) | 4-Me, 5-Me | 3 | 2-(2-Fu) | 4-Me, 5-Me | 3 | —C(Me)$_2$— |
| 23 | Zr | Me | 2-(2-Fu) | 4-Me, 5-Me | 3 | 2-(2-Fu) | 4-Me, 5-Me | 3 | —C(Me)$_2$— |
| 24 | Zr | Bzl | 2-(2-Fu) | 4-Me, 5-Me | 3 | 2-(2-Fu) | 4-Me, 5-Me | 3 | —C(Me)$_2$— |
| 25 | Hf | Cl | 2-(2-Fu) | 4-Me, 5-Me | 3 | 2-(2-Fu) | 4-Me, 5-Me | 3 | —C(Me)$_2$— |
| 26 | Ti | Cl | 2-(2-Fu) | 4-Me, 5-Me | 3 | 2-(2-Fu) | 4-Me, 5-Me | 3 | —C(Me)$_2$— |
| 27 | Hf | Cl | 2-(2-Fu) | 3-Me, 5-Me | 3 | 2-(2-Fu) | 3-Me, 5-Me | 3 | —C(Me)$_2$— |
| 28 | Ti | Cl | 2-(2-Fu) | 3-Me, 5-Me | 3 | 2-(2-Fu) | 3-Me, 5-Me | 3 | —C(Me)$_2$— |
| 29 | Zr | Cl | 2-(3-Fu) | 4-Me, 5-Me | 3 | 2-(3-Fu) | 4-Me, 5-Me | 3 | —C(Me)$_2$— |
| 30 | Zr | Cl | 2-(3-Fu) | 3-Me, 5-Me | 3 | 2-(3-Fu) | 3-Me, 5-Me | 3 | —C(Me)$_2$— |
| 31 | Zr | Cl | 2-[2-(3-Me-Fu)] | 4-Me, 5-Me | 3 | 2-[2-(3-Me-Fu)] | 4-Me, 5-Me | 3 | —C(Me)$_2$— |
| 32 | Zr | Cl | 2-[2-(3-Me-Fu)] | 3-Me, 5-Me | 3 | 2-[2-(3-Me-Fu)] | 3-Me, 5-Me | 3 | —C(Me)$_2$— |
| 33 | Zr | Cl | 2-(2-Thie) | 4-Me, 5-Me | 3 | 2-(2-Thie) | 4-Me, 5-Me | 3 | —C(Me)$_2$— |
| 34 | Zr | Cl | 2-(2-Thie) | 3-Me, 5-Me | 3 | 2-(2-Thie) | 3-Me, 5-Me | 3 | —C(Me)$_2$— |
| 35 | Zr | Cl | 2-(2-Py) | 4-Me, 5-Me | 3 | 2-(2-Py) | 4-Me, 5-Me | 3 | —C(Me)$_2$— |
| 36 | Zr | Cl | 2-(2-Py) | 3-Me, 5-Me | 3 | 2-(2-Py) | 3-Me, 5-Me | 3 | —C(Me)$_2$— |
| 37 | Zr | Cl | 2-(2-BzFu) | 4-Me, 5-Me | 3 | 2-(2-BzFu) | 4-Me, 5-Me | 3 | —C(Me)$_2$— |
| 38 | Zr | Cl | 2-(2-BzFu) | 3-Me, 5-Me | 3 | 2-(2-BzFu) | 3-Me, 5-Me | 3 | —C(Me)$_2$— |
| 39 | Zr | Cl | 2-[2-(1-Me-Pyr)] | 4-Me, 5-Me | 3 | 2-[2-(1-Me-Pyr)] | 4-Me, 5-Me | 3 | —C(Me)$_2$— |
| 40 | Zr | Cl | 2-[2-(1-Me-Pyr)] | 3-Me, 5-Me | 3 | 2-[2-(1-Me-Pyr)] | 3-Me, 5-Me | 3 | —C(Me)$_2$— |

TABLE 3

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 41 | Zr | Cl | 2-(2-Fu) | — | 1 | 2-(2-Fu) | — | 1 | —CH$_2$CH$_2$— |
| 42 | Zr | Cl | 2-(2-Fu) | — | 1 | 2-(2-Fu) | — | 1 | —C$_2$(Me)$_4$— |
| 43 | Zr | Cl | 2-(2-Fu) | 5-Me | 2 | 2-(2-Fu) | 5-Me | 2 | —C$_2$(Me)$_4$— |
| 44 | Zr | Cl | 2-(2-Fu) | 4-Me | 2 | 2-(2-Fu) | 4-Me | 2 | —C$_2$(Me)$_4$— |
| 45 | Zr | Cl | 2-(2-Fu) | 4-OMe | 2 | 2-(2-Fu) | 4-OMe | 2 | —C$_2$(Me)$_4$— |
| 46 | Zr | Cl | 2-(2-Fu) | 4-OPh | 2 | 2-(2-Fu) | 4-OPh | 2 | —C$_2$(Me)$_4$— |
| 47 | Zr | Cl | 2-(2-Fu) | 4-Bzl | 2 | 2-(2-Fu) | 4-Bzl | 2 | —C$_2$(Me)$_4$— |
| 48 | Zr | Cl | 2-(2-Fu) | 4-Tol | 2 | 2-(2-Fu) | 4-Tol | 2 | —C$_2$(Me)$_4$— |
| 49 | Zr | Cl | 2-(2-Fu) | 4-OBzl | 2 | 2-(2-Fu) | 4-OBzl | 2 | —C$_2$(Me)$_4$— |
| 50 | Zr | Cl | 2-(2-Fu) | 4-TMS | 2 | 2-(2-Fu) | 4-TMS | 2 | —C$_2$(Me)$_4$— |
| 51 | Zr | Cl | 2-(2-Fu) | 4-(1-Pyr) | 2 | 2-(2-Fu) | 4-(1-Pyr) | 2 | —C$_2$(Me)$_4$— |
| 52 | Zr | Cl | 2-(2-Fu) | 4-(1-Indo) | 2 | 2-(2-Fu) | 4-(1-Indo) | 2 | —C$_2$(Me)$_4$— |
| 53 | Zr | Cl | 2-(2-Fu) | 3-Me | 2 | 2-(2-Fu) | 3-Me | 2 | —C$_2$(Me)$_4$— |
| 54 | Zr | Cl | 2-(2-Fu) | 3-Me, 5-Me | 3 | 2-(2-Fu) | 3-Me, 5-Me | 3 | —C$_2$(Me)$_4$— |
| 55 | Zr | Cl | 2-(2-Fu) | 4-Me, 5-Me | 3 | 2-(2-Fu) | 4-Me, 5-Me | 3 | —C$_2$(Me)$_4$— |
| 56 | Zr | Cl | 2-(2-Fu) | 4-Et, 5-Me | 3 | 2-(2-Fu) | 4-Et, 5-Me | 3 | —C$_2$(Me)$_4$— |
| 57 | Zr | Cl | 2-(2-Fu) | 4-(i-Pr), 5-Me | 3 | 2-(2-Fu) | 4-(i-Pr), 5-Me | 3 | —C$_2$(Me)$_4$— |
| 58 | Zr | Cl | 2-(2-Fu) | 4-(t-Bu), 5-Me | 3 | 2-(2-Fu) | 4-(t-Bu), 5-Me | 3 | —C$_2$(Me)$_4$— |
| 59 | Zr | Cl | 2-(2-Fu) | 4-Ph, 5-Me | 3 | 2-(2-Fu) | 4-Ph, 5-Me | 3 | —C$_2$(Me)$_4$— |
| 60 | Zr | Cl | 2-(2-Fu) | 3-Ph, 5-Me | 3 | 2-(2-Fu) | 3-Ph, 5-Me | 3 | —C$_2$(Me)$_4$— |
| 61 | Zr | Cl | 2-(2-Fu) | 4-Me, 5-Me | 3 | 2-(2-Fu) | 4-Me, 5-Me | 3 | —C$_2$(Me)$_4$— |
| 62 | Zr | Cl | 2-(2-Fu) | 4-Me, 5-Me | 3 | 2-(2-Fu) | 4-Me, 5-Me | 3 | —C$_2$(Me)$_4$— |
| 63 | Zr | Me | 2-(2-Fu) | 4-Me, 5-Me | 3 | 2-(2-Fu) | 4-Me, 5-Me | 3 | —C$_2$(Me)$_4$— |
| 64 | Zr | Bzl | 2-(2-Fu) | 4-Me, 5-Me | 3 | 2-(2-Fu) | 4-Me, 5-Me | 3 | —C$_2$(Me)$_4$— |
| 65 | Hf | Cl | 2-(2-Fu) | 4-Me, 5-Me | 3 | 2-(2-Fu) | 4-Me, 5-Me | 3 | —C$_2$(Me)$_4$— |
| 66 | Ti | Cl | 2-(2-Fu) | 4-Me, 5-Me | 3 | 2-(2-Fu) | 4-Me, 5-Me | 3 | —C$_2$(Me)$_4$— |
| 67 | Hf | Cl | 2-(2-Fu) | 3-Me, 5-Me | 3 | 2-(2-Fu) | 3-Me, 5-Me | 3 | —C$_2$(Me)$_4$— |
| 68 | Ti | Cl | 2-(2-Fu) | 3-Me, 5-Me | 3 | 2-(2-Fu) | 3-Me, 5-Me | 3 | —C$_2$(Me)$_4$— |
| 69 | Zr | Cl | 2-(3-Fu) | 4-Me, 5-Me | 3 | 2-(3-Fu) | 4-Me, 5-Me | 3 | —C$_2$(Me)$_4$— |
| 70 | Zr | Cl | 2-(3-Fu) | 3-Me, 5-Me | 3 | 2-(3-Fu) | 3-Me, 5-Me | 3 | —C$_2$(Me)$_4$— |
| 71 | Zr | Cl | 2-[2-(3-Me-Fu)] | 4-Me, 5-Me | 3 | 2-[2-(3-Me-Fu)] | 4-Me, 5-Me | 3 | —C$_2$(Me)$_4$— |
| 72 | Zr | Cl | 2-[2-(3-Me-Fu)] | 3-Me, 5-Me | 3 | 2-[2-(3-Me-Fu)] | 3-Me, 5-Me | 3 | —C$_2$(Me)$_4$— |
| 73 | Zr | Cl | 2-(2-Thie) | 4-Me, 5-Me | 3 | 2-(2-Thie) | 4-Me, 5-Me | 3 | —C$_2$(Me)$_4$— |
| 74 | Zr | Cl | 2-(2-Thie) | 3-Me, 5-Me | 3 | 2-(2-Thie) | 3-Me, 5-Me | 3 | —C$_2$(Me)$_4$— |
| 75 | Zr | Cl | 2-(2-Py) | 4-Me, 5-Me | 3 | 2-(2-Py) | 4-Me, 5-Me | 3 | —C$_2$(Me)$_4$— |
| 76 | Zr | Cl | 2-(2-Py) | 3-Me, 5-Me | 3 | 2-(2-Py) | 3-Me, 5-Me | 3 | —C$_2$(Me)$_4$— |
| 77 | Zr | Cl | 2-(2-BzFu) | 4-Me, 5-Me | 3 | 2-(2-BzFu) | 4-Me, 5-Me | 3 | —C$_2$(Me)$_4$— |
| 78 | Zr | Cl | 2-(2-BzFu) | 3-Me, 5-Me | 3 | 2-(2-BzFu) | 3-Me, 5-Me | 3 | —C$_2$(Me)$_4$— |

TABLE 3-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 79 | Zr | Cl | 2-[2-(1-Me-Pyr)] | 4-Me, 5-Me | 3 | 2-[2-(1-Me-Pyr)] | 4-Me, 5-Me | 3 | —C$_2$(Me)$_4$— |
| 80 | Zr | Cl | 2-[2-(1-Me-Pyr)] | 3-Me, 5-Me | 3 | 2-[2-(1-Me-Pyr)] | 3-Me, 5-Me | 3 | —C$_2$(Me)$_4$— |

TABLE 4

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 81 | Zr | Cl | 2-(2-Fu) | — | 1 | 2-(2-Fu) | — | 1 | —SiH$_2$— |
| 82 | Zr | Cl | 2-(2-Fu) | — | 1 | 2-(2-Fu) | — | 1 | —Si(Me)$_2$— |
| 83 | Zr | Cl | 2-(2-Fu) | 5-Me | 2 | 2-(2-Fu) | 5-Me | 2 | —Si(Me)$_2$— |
| 84 | Zr | Cl | 2-(2-Fu) | 4-Me | 2 | 2-(2-Fu) | 4-Me | 2 | —Si(Me)$_2$— |
| 85 | Zr | Cl | 2-(2-Fu) | 4-OMe | 2 | 2-(2-Fu) | 4-OMe | 2 | —Si(Me)$_2$— |
| 86 | Zr | Cl | 2-(2-Fu) | 4-OPh | 2 | 2-(2-Fu) | 4-OPh | 2 | —Si(Me)$_2$— |
| 87 | Zr | Cl | 2-(2-Fu) | 4-Bzl | 2 | 2-(2-Fu) | 4-Bzl | 2 | —Si(Me)$_2$— |
| 88 | Zr | Cl | 2-(2-Fu) | 4-Tol | 2 | 2-(2-Fu) | 4-Tol | 2 | —Si(Me)$_2$— |
| 89 | Zr | Cl | 2-(2-Fu) | 4-OBzl | 2 | 2-(2-Fu) | 4-OBzl | 2 | —Si(Me)$_2$— |
| 90 | Zr | Cl | 2-(2-Fu) | 4-TMS | 2 | 2-(2-Fu) | 4-TMS | 2 | —Si(Me)$_2$— |
| 91 | Zr | Cl | 2-(2-Fu) | 4-(1-Pyr) | 2 | 2-(2-Fu) | 4-(1-Pyr) | 2 | —Si(Me)$_2$— |
| 92 | Zr | Cl | 2-(2-Fu) | 4-(1-Indo) | 2 | 2-(2-Fu) | 4-(1-Indo) | 2 | —Si(Me)$_2$— |
| 93 | Zr | Cl | 2-(2-Fu) | 3-Me | 2 | 2-(2-Fu) | 3-Me | 2 | —Si(Me)$_2$— |
| 94 | Zr | Cl | 2-(2-Fu) | 3-Me, 5-Me | 3 | 2-(2-Fu) | 3-Me, 5-Me | 3 | —Si(Me)$_2$— |
| 95 | Zr | Cl | 2-(2-Fu) | 4-Me, 5-Me | 3 | 2-(2-Fu) | 4-Me, 5-Me | 3 | —Si(Me)$_2$— |
| 96 | Zr | Cl | 2-(2-Fu) | 4-Et, 5-Me | 3 | 2-(2-Fu) | 4-Et, 5-Me | 3 | —Si(Me)$_2$— |
| 97 | Zr | Cl | 2-(2-Fu) | 4-(i-Pr), 5-Me | 3 | 2-(2-Fu) | 4-(i-Pr), 5-Me | 3 | —Si(Me)$_2$— |
| 98 | Zr | Cl | 2-(2-Fu) | 4-(t-Bu), 5-Me | 3 | 2-(2-Fu) | 4-(t-Bu), 5-Me | 3 | —Si(Me)$_2$— |
| 99 | Zr | Cl | 2-(2-Fu) | 4-Ph, 5-Me | 3 | 2-(2-Fu) | 4-Ph, 5-Me | 3 | —Si(Me)$_2$— |
| 100 | Zr | Cl | 2-(2-Fu) | 3-Ph, 5-Me | 3 | 2-(2-Fu) | 3-Ph, 5-Me | 3 | —Si(Me)$_2$— |
| 101 | Zr | Cl | 2-(2-Fu) | 4-Me, 5-Me | 3 | 2-(2-Fu) | 4-Me, 5-Me | 3 | —Si(Me)$_2$— |
| 102 | Zr | Cl | 2-(2-Fu) | 4-Me, 5-Me | 3 | 2-(2-Fu) | 4-Me, 5-Me | 3 | —Si(Me)$_2$— |
| 103 | Zr | Me | 2-(2-Fu) | 4-Me, 5-Me | 3 | 2-(2-Fu) | 4-Me, 5-Me | 3 | —Si(Me)$_2$— |
| 104 | Zr | Bzl | 2-(2-Fu) | 4-Me, 5-Me | 3 | 2-(2-Fu) | 4-Me, 5-Me | 3 | —Si(Me)$_2$— |
| 105 | Hf | Cl | 2-(2-Fu) | 4-Me, 5-Me | 3 | 2-(2-Fu) | 4-Me, 5-Me | 3 | —Si(Me)$_2$— |
| 106 | Ti | Cl | 2-(2-Fu) | 4-Me, 5-Me | 3 | 2-(2-Fu) | 4-Me, 5-Me | 3 | —Si(Me)$_2$— |
| 107 | Hf | Cl | 2-(2-Fu) | 3-Me, 5-Me | 3 | 2-(2-Fu) | 3-Me, 5-Me | 3 | —Si(Me)$_2$— |
| 108 | Ti | Cl | 2-(2-Fu) | 3-Me, 5-Me | 3 | 2-(2-Fu) | 3-Me, 5-Me | 3 | —Si(Me)$_2$— |
| 109 | Zr | Cl | 2-(3-Fu) | 4-Me, 5-Me | 3 | 2-(3-Fu) | 4-Me, 5-Me | 3 | —Si(Me)$_2$— |
| 110 | Zr | Cl | 2-(3-Fu) | 3-Me, 5-Me | 3 | 2-(3-Fu) | 3-Me, 5-Me | 3 | —Si(Me)$_2$— |
| 111 | Zr | Cl | 2-[2-(3-Me-Fu)] | 4-Me, 5-Me | 3 | 2-[2-(3-Me-Fu)] | 4-Me, 5-Me | 3 | —Si(Me)$_2$— |
| 112 | Zr | Cl | 2-[2-(3-Me-Fu)] | 3-Me, 5-Me | 3 | 2-[2-(3-Me-Fu)] | 3-Me, 5-Me | 3 | —Si(Me)$_2$— |
| 113 | Zr | Cl | 2-(2-Thie) | 4-Me, 5-Me | 3 | 2-(2-Thie) | 4-Me, 5-Me | 3 | —Si(Me)$_2$— |
| 114 | Zr | Cl | 2-(2-Thie) | 3-Me, 5-Me | 3 | 2-(2-Thie) | 3-Me, 5-Me | 3 | —Si(Me)$_2$— |
| 115 | Zr | Cl | 2-(2-Py) | 4-Me, 5-Me | 3 | 2-(2-Py) | 4-Me, 5-Me | 3 | —Si(Me)$_2$— |
| 116 | Zr | Cl | 2-(2-Py) | 3-Me, 5-Me | 3 | 2-(2-Py) | 3-Me, 5-Me | 3 | —Si(Me)$_2$— |
| 117 | Zr | Cl | 2-(2-BzFu) | 4-Me, 5-Me | 3 | 2-(2-BzFu) | 4-Me, 5-Me | 3 | —Si(Me)$_2$— |
| 118 | Zr | Cl | 2-(2-BzFu) | 3-Me, 5-Me | 3 | 2-(2-BzFu) | 3-Me, 5-Me | 3 | —Si(Me)$_2$— |
| 119 | Zr | Cl | 2-[2-(N-Me-Pyr)] | 4-Me, 5-Me | 3 | 2-[2-(N-Me-Pyr)] | 4-Me, 5-Me | 3 | —Si(Me)$_2$— |
| 120 | Zr | Cl | 2-[2-(N-Me-Pyr)] | 3-Me, 5-Me | 3 | 2-[2-(N-Me-Pyr)] | 3-Me, 5-Me | 3 | —Si(Me)$_2$— |

TABLE 5

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 121 | Zr | Cl | 2-(2-Fu) | — | 1 | 2-(2-Fu) | — | 1 | —GeH$_2$— |
| 122 | Zr | Cl | 2-(2-Fu) | — | 1 | 2-(2-Fu) | — | 1 | —Ge(Me)$_2$— |
| 123 | Zr | Cl | 2-(2-Fu) | 5-Me | 2 | 2-(2-Fu) | 5-Me | 2 | —Ge(Me)$_2$— |
| 124 | Zr | Cl | 2-(2-Fu) | 4-Me | 2 | 2-(2-Fu) | 4-Me | 2 | —Ge(Me)$_2$— |
| 125 | Zr | Cl | 2-(2-Fu) | 4-OMe | 2 | 2-(2-Fu) | 4-OMe | 2 | —Ge(Me)$_2$— |
| 126 | Zr | Cl | 2-(2-Fu) | 4-OPh | 2 | 2-(2-Fu) | 4-OPh | 2 | —Ge(Me)$_2$— |
| 127 | Zr | Cl | 2-(2-Fu) | 4-Bzl | 2 | 2-(2-Fu) | 4-Bzl | 2 | —Ge(Me)$_2$— |
| 128 | Zr | Cl | 2-(2-Fu) | 4-Tol | 2 | 2-(2-Fu) | 4-Tol | 2 | —Ge(Me)$_2$— |
| 129 | Zr | Cl | 2-(2-Fu) | 4-OBzl | 2 | 2-(2-Fu) | 4-OBzl | 2 | —Ge(Me)$_2$— |
| 130 | Zr | Cl | 2-(2-Fu) | 4-TMS | 2 | 2-(2-Fu) | 4-TMS | 2 | —Ge(Me)$_2$— |
| 131 | Zr | Cl | 2-(2-Fu) | 4-(1-Pyr) | 2 | 2-(2-Fu) | 4-(1-Pyr) | 2 | —Ge(Me)$_2$— |
| 132 | Zr | Cl | 2-(2-Fu) | 4-(1-Indo) | 2 | 2-(2-Fu) | 4-(1-Indo) | 2 | —Ge(Me)$_2$— |
| 133 | Zr | Cl | 2-(2-Fu) | 3-Me | 2 | 2-(2-Fu) | 3-Me | 2 | —Ge(Me)$_2$— |
| 134 | Zr | Cl | 2-(2-Fu) | 3-Me, 5-Me | 3 | 2-(2-Fu) | 3-Me, 5-Me | 3 | —Ge(Me)$_2$— |
| 135 | Zr | Cl | 2-(2-Fu) | 4-Me, 5-Me | 3 | 2-(2-Fu) | 4-Me, 5-Me | 3 | —Ge(Me)$_2$— |
| 136 | Zr | Cl | 2-(2-Fu) | 4-Et, 5-Me | 3 | 2-(2-Fu) | 4-Et, 5-Me | 3 | —Ge(Me)$_2$— |
| 137 | Zr | Cl | 2-(2-Fu) | 4-(i-Pr), 5-Me | 3 | 2-(2-Fu) | 4-(i-Pr), 5-Me | 3 | —Ge(Me)$_2$— |

TABLE 5-continued

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 138 | Zr | Cl | 2-(2-Fu) | 4-(t-Bu), 5-Me | 3 | 2-(2-Fu) | 4-(t-Bu), 5-Me | 3 | —Ge(Me)₂— |
| 139 | Zr | Cl | 2-(2-Fu) | 4-Ph, 5-Me | 3 | 2-(2-Fu) | 4-Ph, 5-Me | 3 | —Ge(Me)₂— |
| 140 | Zr | Cl | 2-(2-Fu) | 3-Ph, 5-Me | 3 | 2-(2-Fu) | 3-Ph, 5-Me | 3 | —Ge(Me)₂— |
| 141 | Zr | Cl | 2-(2-Fu) | 4-Me, 5-Me | 3 | 2-(2-Fu) | 4-Me, 5-Me | 3 | —Ge(Me)₂— |
| 142 | Zr | Cl | 2-(2-Fu) | 4-Me, 5-Me | 3 | 2-(2-Fu) | 4-Me, 5-Me | 3 | —Ge(Me)₂— |
| 143 | Zr | Me | 2-(2-Fu) | 4-Me, 5-Me | 3 | 2-(2-Fu) | 4-Me, 5-Me | 3 | —Ge(Me)₂— |
| 144 | Zr | Bzl | 2-(2-Fu) | 4-Me, 5-Me | 3 | 2-(2-Fu) | 4-Me, 5-Me | 3 | —Ge(Me)₂— |
| 145 | Hf | Cl | 2-(2-Fu) | 4-Me, 5-Me | 3 | 2-(2-Fu) | 4-Me, 5-Me | 3 | —Ge(Me)₂— |
| 146 | Ti | Cl | 2-(2-Fu) | 4-Me, 5-Me | 3 | 2-(2-Fu) | 4-Me, 5-Me | 3 | —Ge(Me)₂— |
| 147 | Hf | Cl | 2-(2-Fu) | 3-Me, 5-Me | 3 | 2-(2-Fu) | 3-Me, 5-Me | 3 | —Ge(Me)₂— |
| 148 | Ti | Cl | 2-(2-Fu) | 3-Me, 5-Me | 3 | 2-(2-Fu) | 3-Me, 5-Me | 3 | —Ge(Me)₂— |
| 149 | Zr | Cl | 2-(3-Fu) | 4-Me, 5-Me | 3 | 2-(3-Fu) | 4-Me, 5-Me | 3 | —Ge(Me)₂— |
| 150 | Zr | Cl | 2-(3-Fu) | 3-Me, 5-Me | 3 | 2-(3-Fu) | 3-Me, 5-Me | 3 | —Ge(Me)₂— |
| 151 | Zr | Cl | 2-[2-(3-Me-Fu)] | 4-Me, 5-Me | 3 | 2-[2-(3-Me-Fu)] | 4-Me, 5-Me | 3 | —Ge(Me)₂— |
| 152 | Zr | Cl | 2-[2-(3-Me-Fu)] | 3-Me, 5-Me | 3 | 2-[2-(3-Me-Fu)] | 3-Me, 5-Me | 3 | —Ge(Me)₂— |
| 153 | Zr | Cl | 2-(2-Thie) | 4-Me, 5-Me | 3 | 2-(2-Thie) | 4-Me, 5-Me | 3 | —Ge(Me)₂— |
| 154 | Zr | Cl | 2-(2-Thie) | 3-Me, 5-Me | 3 | 2-(2-Thie) | 3-Me, 5-Me | 3 | —Ge(Me)₂— |
| 155 | Zr | Cl | 2-(2-Py) | 4-Me, 5-Me | 3 | 2-(2-Py) | 4-Me, 5-Me | 3 | —Ge(Me)₂— |
| 156 | Zr | Cl | 2-(2-Py) | 3-Me, 5-Me | 3 | 2-(2-Py) | 3-Me, 5-Me | 3 | —Ge(Me)₂— |
| 157 | Zr | Cl | 2-(2-BzFu) | 4-Me, 5-Me | 3 | 2-(2-BzFu) | 4-Me, 5-Me | 3 | —Ge(Me)₂— |
| 158 | Zr | Cl | 2-(2-BzFu) | 3-Me, 5-Me | 3 | 2-(2-BzFu) | 3-Me, 5-Me | 3 | —Ge(Me)₂— |
| 159 | Zr | Cl | 2-[2-(N-Me-Pyr)] | 4-Me, 5-Me | 3 | 2-[2-(N-Me-Pyr)] | 4-Me, 5-Me | 3 | —Ge(Me)₂— |
| 160 | Zr | Cl | 2-[2-(N-Me-Pyr)] | 3-Me, 5--Me | 3 | 2-[2-(N-Me-Pyr)] | 3-Me, 5-Me | 3 | —Ge(Me)₂— |

TABLE 6

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 161 | Zr | Cl | 3-(2-Fu) | — | 1 | 3-(2-Fu) | — | 1 | —GeH₂— |
| 162 | Zr | Cl | 3-(2-Fu) | — | 1 | 3-(2-Fu) | — | 1 | —Ge(Me)₂— |
| 163 | Zr | Cl | 3-(2-Fu) | 5-Me | 2 | 3-(2-Fu) | 5-Me | 2 | —Ge(Me)₂— |
| 164 | Zr | Cl | 3-(2-Fu) | 4-Me | 2 | 3-(2-Fu) | 4-Me | 2 | —Ge(Me)₂— |
| 165 | Zr | Cl | 3-(2-Fu) | 4-OMe | 2 | 3-(2-Fu) | 4-OMe | 2 | —Ge(Me)₂— |
| 166 | Zr | Cl | 3-(2-Fu) | 4-OPh | 2 | 3-(2-Fu) | 4-OPh | 2 | —Ge(Me)₂— |
| 167 | Zr | Cl | 3-(2-Fu) | 4-Bzl | 2 | 3-(2-Fu) | 4-Bzl | 2 | —Ge(Me)₂— |
| 168 | Zr | Cl | 3-(2-Fu) | 4-Tol | 2 | 3-(2-Fu) | 4-Tol | 2 | —Ge(Me)₂— |
| 169 | Zr | Cl | 3-(2-Fu) | 4-OBzl | 2 | 3-(2-Fu) | 4-OBzl | 2 | —Ge(Me)₂— |
| 170 | Zr | Cl | 3-(2-Fu) | 4-TMS | 2 | 3-(2-Fu) | 4-TMS | 2 | —Ge(Me)₂— |
| 171 | Zr | Cl | 3-(2-Fu) | 4-(1-Pyr) | 2 | 3-(2-Fu) | 4-(1-Pyr) | 2 | —Ge(Me)₂— |
| 172 | Zr | Cl | 3-(2-Fu) | 4-(1-Indo) | 2 | 3-(2-Fu) | 4-(1-Indo) | 2 | —Ge(Me)₂— |
| 173 | Zr | Cl | 3-(2-Fu) | 2-Me | 2 | 3-(2-Fu) | 3-Me | 2 | —Ge(Me)₂— |
| 174 | Zr | Cl | 3-(2-Fu) | 4-Me, 5-Me | 3 | 3-(2-Fu) | 3-Me, 5-Me | 3 | —Ge(Me)₂— |
| 175 | Zr | Cl | 3-(2-Fu) | 4-Me, 5-Me | 3 | 3-(2-Fu) | 4-Me, 5-Me | 3 | —Ge(Me)₂— |
| 176 | Zr | Cl | 3-(2-Fu) | 4-Et, 5-Me | 3 | 3-(2-Fu) | 4-Et, 5-Me | 3 | —Ge(Me)₂— |
| 177 | Zr | Cl | 3-(2-Fu) | 4-(i-Pr), 5-Me | 3 | 3-(2-Fu) | 4-(i-Pr), 5-Me | 3 | —Ge(Me)₂— |
| 178 | Zr | Cl | 3-(2-Fu) | 4-(t-Bu), 5-Me | 3 | 3-(2-Fu) | 4-(t-Bu), 5-Me | 3 | —Ge(Me)₂— |
| 179 | Zr | Cl | 3-(2-Fu) | 4-Ph, 5-Me | 3 | 3-(2-Fu) | 4-Ph, 5-Me | 3 | —Ge(Me)₂— |
| 180 | Zr | Cl | 3-(2-Fu) | 2-Ph, 5-Me | 3 | 3-(2-Fu) | 3-Ph, 5-Me | 3 | —Ge(Me)₂— |
| 181 | Zr | Cl | 3-(2-Fu) | 4-Me, 5-Me | 3 | 3-(2-Fu) | 4-Me, 5-Me | 3 | —Ge(Me)₂— |
| 182 | Zr | Cl | 3-(2-Fu) | 4-Me, 5-Me | 3 | 3-(2-Fu) | 4-Me, 5-Me | 3 | —Ge(Me)₂— |
| 183 | Zr | Me | 3-(2-Fu) | 4-Me, 5-Me | 3 | 3-(2-Fu) | 4-Me, 5-Me | 3 | —Ge(Me)₂— |
| 184 | Zr | Bzl | 3-(2-Fu) | 4-Me, 5-Me | 3 | 3-(2-Fu) | 4-Me, 5-Me | 3 | —Ge(Me)₂— |
| 185 | Hf | Cl | 3-(2-Fu) | 4-Me, 5-Me | 3 | 3-(2-Fu) | 4-Me, 5-Me | 3 | —Ge(Me)₂— |
| 186 | Ti | Cl | 3-(2-Fu) | 4-Me, 5-Me | 3 | 3-(2-Fu) | 4-Me, 5-Me | 3 | —Ge(Me)₂— |
| 187 | Hf | Cl | 3-(2-Fu) | 2-Me, 5-Me | 3 | 3-(2-Fu) | 3-Me, 5-Me | 3 | —Ge(Me)₂— |
| 188 | Ti | Cl | 3-(2-Fu) | 2-Me, 5-Me | 3 | 3-(2-Fu) | 3-Me, 5-Me | 3 | —Ge(Me)₂— |
| 189 | Zr | Cl | 3-(3-Fu) | 4-Me, 5-Me | 3 | 3-(3-Fu) | 4-Me, 5-Me | 3 | —Ge(Me)₂— |
| 190 | Zr | Cl | 3-(3-Fu) | 2-Me, 5-Me | 3 | 3-(3-Fu) | 3-Me, 5-Me | 3 | —Ge(Me)₂— |
| 191 | Zr | Cl | 3-[2-(3-Me-Fu)] | 4-Me, 5-Me | 3 | 3-[2-(3-Me-Fu)] | 4-Me, 5-Me | 3 | —Ge(Me)₂— |
| 192 | Zr | Cl | 3-[2-(3-Me-Fu)] | 2-Me, 5-Me | 3 | 3-[2-(3-Me-Fu)] | 3-Me, 5-Me | 3 | —Ge(Me)₂— |
| 193 | Zr | Cl | 3-(2-Thie) | 4-Me, 5-Me | 3 | 3-(2-Thie) | 4-Me, 5-Me | 3 | —Ge(Me)₂— |
| 194 | Zr | Cl | 3-(2-Thie) | 2-Me, 5-Me | 3 | 3-(2-Thie) | 3-Me, 5-Me | 3 | —Ge(Me)₂— |
| 195 | Zr | Cl | 3-(2-Py) | 4-Me, 5-Me | 3 | 3-(2-Py) | 4-Me, 5-Me | 3 | —Ge(Me)₂— |
| 196 | Zr | Cl | 3-(2-Py) | 2-Me, 5-Me | 3 | 3-(2-Py) | 3-Me, 5-Me | 3 | —Ge(Me)₂— |
| 197 | Zr | Cl | 3-(2-BzFu) | 4-Me, 5-Me | 3 | 3-(2-BzFu) | 4-Me, 5-Me | 3 | —Ge(Me)₂— |
| 198 | Zr | Cl | 3-(2-BzFu) | 2-Me, 5-Me | 3 | 3-(2-BzFu) | 3-Me, 5-Me | 3 | —Ge(Me)₂— |
| 199 | Zr | Cl | 3-[2-(N-Me-Pyr)] | 4-Me, 5-Me | 3 | 3-[2-(N-Me-Pyr)] | 4-Me, 5-Me | 3 | —Ge(Me)₂— |
| 200 | Zr | Cl | 3-[2-(N-Me-Pyr)] | 2-Me, 5-Me | 3 | 3-[2-(N-Me-Pyr)] | 3-Me, 5-Me | 3 | —Ge(Me)₂— |

TABLE 7

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 201 | Zr | Cl | 3-(2-Fu) | — | 1 | 3-(2-Fu) | — | 1 | —CH$_2$CH$_2$— |
| 202 | Zr | Cl | 3-(2-Fu) | — | 1 | 3-(2-Fu) | — | 1 | —C$_2$(Me)$_4$— |
| 203 | Zr | Cl | 3-(2-Fu) | 5-Me | 2 | 3-(2-Fu) | 5-Me | 2 | —C$_2$(Me)$_4$— |
| 204 | Zr | Cl | 3-(2-Fu) | 4-Me | 2 | 3-(2-Fu) | 4-Me | 2 | —C$_2$(Me)$_4$— |
| 205 | Zr | Cl | 3-(2-Fu) | 4-OMe | 2 | 3-(2-Fu) | 4-OMe | 2 | —C$_2$(Me)$_4$— |
| 206 | Zr | Cl | 3-(2-Fu) | 4-OPh | 2 | 3-(2-Fu) | 4-OPh | 2 | —C$_2$(Me)$_4$— |
| 207 | Zr | Cl | 3-(2-Fu) | 4-Bzl | 2 | 3-(2-Fu) | 4-Bzl | 2 | —C$_2$(Me)$_4$— |
| 208 | Zr | Cl | 3-(2-Fu) | 4-Tol | 2 | 3-(2-Fu) | 4-Tol | 2 | —C$_2$(Me)$_4$— |
| 209 | Zr | Cl | 3-(2-Fu) | 4-OBzl | 2 | 3-(2-Fu) | 4-OBzl | 2 | —C$_2$(Me)$_4$— |
| 210 | Zr | Cl | 3-(2-Fu) | 4-TMS | 2 | 3-(2-Fu) | 4-TMS | 2 | —C$_2$(Me)$_4$— |
| 211 | Zr | Cl | 3-(2-Fu) | 4-(1-Pyr) | 2 | 3-(2-Fu) | 4-(1-Pyr) | 2 | —C$_2$(Me)$_4$— |
| 212 | Zr | Cl | 3-(2-Fu) | 4-(1-Indo) | 2 | 3-(2-Fu) | 4-(1-Indo) | 2 | —C$_2$(Me)$_4$— |
| 213 | Zr | Cl | 3-(2-Fu) | 2-Me | 2 | 3-(2-Fu) | 2-Me | 2 | —C$_2$(Me)$_4$— |
| 214 | Zr | Cl | 3-(2-Fu) | 2-Me, 5-Me | 3 | 3-(2-Fu) | 2-Me, 5-Me | 3 | —C$_2$(Me)$_4$— |
| 215 | Zr | Cl | 3-(2-Fu) | 4-Me, 5-Me | 3 | 3-(2-Fu) | 4-Me, 5-Me | 3 | —C$_2$(Me)$_4$— |
| 216 | Zr | Cl | 3-(2-Fu) | 4-Et, 5-Me | 3 | 3-(2-Fu) | 4-Et, 5-Me | 3 | —C$_2$(Me)$_4$— |
| 217 | Zr | Cl | 3-(2-Fu) | 4-(i-Pr), 5-Me | 3 | 3-(2-Fu) | 4-(i-Pr), 5-Me | 3 | —C$_2$(Me)$_4$— |
| 218 | Zr | Cl | 3-(2-Fu) | 4-(t-Bu), 5-Me | 3 | 3-(2-Fu) | 4-(t-Bu), 5-Me | 3 | —C$_2$(Me)$_4$— |
| 219 | Zr | Cl | 3-(2-Fu) | 4-Ph, 5-Me | 3 | 3-(2-Fu) | 4-Ph, 5-Me | 3 | —C$_2$(Me)$_4$— |
| 220 | Zr | Cl | 3-(2-Fu) | 2-Ph, 5-Me | 3 | 3-(2-Fu) | 2-Ph, 5-Me | 3 | —C$_2$(Me)$_4$— |
| 221 | Zr | Cl | 3-(2-Fu) | 4-Me, 5-Me | 3 | 3-(2-Fu) | 4-Me, 5-Me | 3 | —C$_2$(Me)$_4$— |
| 222 | Zr | Cl | 3-(2-Fu) | 4-Me, 5-Me | 3 | 3-(2-Fu) | 4-Me, 5-Me | 3 | —C$_2$(Me)$_4$— |
| 223 | Zr | Me | 3-(2-Fu) | 4-Me, 5-Me | 3 | 3-(2-Fu) | 4-Me, 5-Me | 3 | —C$_2$(Me)$_4$— |
| 224 | Zr | Bzl | 3-(2-Fu) | 4-Me, 5-Me | 3 | 3-(2-Fu) | 4-Me, 5-Me | 3 | —C$_2$(Me)$_4$— |
| 225 | Hf | Cl | 3-(2-Fu) | 4-Me, 5-Me | 3 | 3-(2-Fu) | 4-Me, 5-Me | 3 | —C$_2$(Me)$_4$— |
| 226 | Ti | Cl | 3-(2-Fu) | 4-Me, 5-Me | 3 | 3-(2-Fu) | 4-Me, 5-Me | 3 | —C$_2$(Me)$_4$— |
| 227 | Hf | Cl | 3-(2-Fu) | 2-Me, 5-Me | 3 | 3-(2-Fu) | 2-Me, 5-Me | 3 | —C$_2$(Me)$_4$— |
| 228 | Ti | Cl | 3-(2-Fu) | 2-Me, 5-Me | 3 | 3-(2-Fu) | 2-Me, 5-Me | 3 | —C$_2$(Me)$_4$— |
| 229 | Zr | Cl | 3-(3-Fu) | 4-Me, 5-Me | 3 | 3-(3-Fu) | 4-Me, 5-Me | 3 | —C$_2$(Me)$_4$— |
| 230 | Zr | Cl | 3-(3-Fu) | 2-Me, 5-Me | 3 | 3-(3-Fu) | 2-Me, 5-Me | 3 | —C$_2$(Me)$_4$— |
| 231 | Zr | Cl | 3-[2-(3-Me-Fu)] | 4-Me, 5-Me | 3 | 3-[2-(3-Me-Fu)] | 4-Me, 5-Me | 3 | —C$_2$(Me)$_4$— |
| 232 | Zr | Cl | 3-[2-(3-Me-Fu)] | 2-Me, 5-Me | 3 | 3-[2-(3-Me-Fu)] | 2-Me, 5-Me | 3 | —C$_2$(Me)$_4$— |
| 233 | Zr | Cl | 3-(2-Thie) | 4-Me, 5-Me | 3 | 3-(2-Thie) | 4-Me, 5-Me | 3 | —C$_2$(Me)$_4$— |
| 234 | Zr | Cl | 3-(2-Thie) | 2-Me, 5-Me | 3 | 3-(2-Thie) | 2-Me, 5-Me | 3 | —C$_2$(Me)$_4$— |
| 235 | Zr | Cl | 3-(2-Py) | 4-Me, 5-Me | 3 | 3-(2-Py) | 4-Me, 5-Me | 3 | —C$_2$(Me)$_4$— |
| 236 | Zr | Cl | 3-(2-Py) | 2-Me, 5-Me | 3 | 3-(2-Py) | 2-Me, 5-Me | 3 | —C$_2$(Me)$_4$— |
| 237 | Zr | Cl | 3-(2-BzFu) | 4-Me, 5-Me | 3 | 3-(2-BzFu) | 4-Me, 5-Me | 3 | —C$_2$(Me)$_4$— |
| 238 | Zr | Cl | 3-(2-BzFu) | 2-Me, 5-Me | 3 | 3-(2-BzFu) | 2-Me, 5-Me | 3 | —C$_2$(Me)$_4$— |
| 239 | Zr | Cl | 3-[2-(N-Me-Pyr)] | 4-Me, 5-Me | 3 | 3-[2-(N-Me-Pyr)] | 4-Me, 5-Me | 3 | —C$_2$(Me)$_4$— |
| 240 | Zr | Cl | 3-[2-(N-Me-Pyr)] | 2-Me, 5-Me | 3 | 3-[2-(N-Me-Pyr)] | 2-Me, 5-Me | 3 | —C$_2$(Me)$_4$— |

TABLE 8

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 241 | Zr | Cl | 3-(2-Fu) | — | 1 | 3-(2-Fu) | — | 1 | —SiH$_2$— |
| 242 | Zr | Cl | 3-(2-Fu) | — | 1 | 3-(2-Fu) | — | 1 | —Si(Me)$_2$— |
| 243 | Zr | Cl | 3-(2-Fu) | 5-Me | 2 | 3-(2-Fu) | 5-Me | 2 | —Si(Me)$_2$— |
| 244 | Zr | Cl | 3-(2-Fu) | 4-Me | 2 | 3-(2-Fu) | 4-Me | 2 | —Si(Me)$_2$— |
| 245 | Zr | Cl | 3-(2-Fu) | 4-OMe | 2 | 3-(2-Fu) | 4-OMe | 2 | —Si(Me)$_2$— |
| 246 | Zr | Cl | 3-(2-Fu) | 4-OPh | 2 | 3-(2-Fu) | 4-OPh | 2 | —Si(Me)$_2$— |
| 247 | Zr | Cl | 3-(2-Fu) | 4-Bzl | 2 | 3-(2-Fu) | 4-Bzl | 2 | —Si(Me)$_2$— |
| 248 | Zr | Cl | 3-(2-Fu) | 4-Tol | 2 | 3-(2-Fu) | 4-Tol | 2 | —Si(Me)$_2$— |
| 249 | Zr | Cl | 3-(2-Fu) | 4-OBzl | 2 | 3-(2-Fu) | 4-OBzl | 2 | —Si(Me)$_2$— |
| 250 | Zr | Cl | 3-(2-Fu) | 4-TMS | 2 | 3-(2-Fu) | 4-TMS | 2 | —Si(Me)$_2$— |
| 251 | Zr | Cl | 3-(2-Fu) | 4-(1-Pyr) | 2 | 3-(2-Fu) | 4-(1-Pyr) | 2 | —Si(Me)$_2$— |
| 252 | Zr | Cl | 3-(2-Fu) | 4-(1-Indo) | 2 | 3-(2-Fu) | 4-(1-Indo) | 2 | —Si(Me)$_2$— |
| 253 | Zr | Cl | 3-(2-Fu) | 2-Me | 2 | 3-(2-Fu) | 2-Me | 2 | —Si(Me)$_2$— |
| 254 | Zr | Cl | 3-(2-Fu) | 2-Me, 5-Me | 3 | 3-(2-Fu) | 2-Me, 5-Me | 3 | —Si(Me)$_2$— |
| 255 | Zr | Cl | 3-(2-Fu) | 4-Me, 5-Me | 3 | 3-(2-Fu) | 4-Me, 5-Me | 3 | —Si(Me)$_2$— |
| 256 | Zr | Cl | 3-(2-Fu) | 4-Et, 5-Me | 3 | 3-(2-Fu) | 4-Et, 5-Me | 3 | —Si(Me)$_2$— |
| 257 | Zr | Cl | 3-(2-Fu) | 4-(i-Pr), 5-Me | 3 | 3-(2-Fu) | 4-(i-Pr), 5-Me | 3 | —Si(Me)$_2$— |
| 258 | Zr | Cl | 3-(2-Fu) | 4-(t-Bu), 5-Me | 3 | 3-(2-Fu) | 4-(t-Bu), 5-Me | 3 | —Si(Me)$_2$— |
| 259 | Zr | Cl | 3-(2-Fu) | 4-Ph, 5-Me | 3 | 3-(2-Fu) | 4-Ph, 5-Me | 3 | —Si(Me)$_2$— |
| 260 | Zr | Cl | 3-(2-Fu) | 2-Ph, 5-Me | 3 | 3-(2-Fu) | 2-Ph, 5-Me | 3 | —Si(Me)$_2$— |
| 261 | Zr | Cl | 3-(2-Fu) | 4-Me, 5-Me | 3 | 3-(2-Fu) | 4-Me, 5-Me | 3 | —Si(Me)$_2$— |
| 262 | Zr | Cl | 3-(2-Fu) | 4-Me, 5-Me | 3 | 3-(2-Fu) | 4-Me, 5-Me | 3 | —Si(Me)$_2$— |
| 263 | Zr | Me | 3-(2-Fu) | 4-Me, 5-Me | 3 | 3-(2-Fu) | 4-Me, 5-Me | 3 | —Si(Me)$_2$— |

TABLE 8-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 264 | Zr | Bzl | 3-(2-Fu) | 4-Me, 5-Me | 3 | 3-(2-Fu) | 4-Me, 5-Me | 3 | —Si(Me)₂— |
| 265 | Hf | Cl | 3-(2-Fu) | 4-Me, 5-Me | 3 | 3-(2-Fu) | 4-Me, 5-Me | 3 | —Si(Me)₂— |
| 266 | Ti | Cl | 3-(2-Fu) | 4-Me, 5-Me | 3 | 3-(2-Fu) | 4-Me, 5-Me | 3 | —Si(Me)₂— |
| 267 | Hf | Cl | 3-(2-Fu) | 2-Me, 5-Me | 3 | 3-(2-Fu) | 2-Me, 5-Me | 3 | —Si(Me)₂— |
| 268 | Ti | Cl | 3-(2-Fu) | 2-Me, 5-Me | 3 | 3-(2-Fu) | 2-Me, 5-Me | 3 | —Si(Me)₂— |
| 269 | Zr | Cl | 3-(3-Fu) | 4-Me, 5-Me | 3 | 3-(3-Fu) | 4-Me, 5-Me | 3 | —Si(Me)₂— |
| 270 | Zr | Cl | 3-(3-Fu) | 2-Me, 5-Me | 3 | 3-(3-Fu) | 2-Me, 5-Me | 3 | —Si(Me)₂— |
| 271 | Zr | Cl | 3-[2-(3-Me-Fu)] | 4-Me, 5-Me | 3 | 3-[2-(3-Me-Fu)] | 4-Me, 5-Me | 3 | —Si(Me)₂— |
| 272 | Zr | Cl | 3-[2-(3-Me-Fu)] | 2-Me, 5-Me | 3 | 3-[2-(3-Me-Fu)] | 2-Me, 5-Me | 3 | —Si(Me)₂— |
| 273 | Zr | Cl | 3-(2-Thie) | 4-Me, 5-Me | 3 | 3-(2-Thie) | 4-Me, 5-Me | 3 | —Si(Me)₂— |
| 274 | Zr | Cl | 3-(2-Thie) | 2-Me, 5-Me | 3 | 3-(2-Thie) | 2-Me, 5-Me | 3 | —Si(Me)₂— |
| 275 | Zr | Cl | 3-(2-Py) | 4-Me, 5-Me | 3 | 3-(2-Py) | 4-Me, 5-Me | 3 | —Si(Me)₂— |
| 276 | Zr | Cl | 3-(2-Py) | 2-Me, 5-Me | 3 | 3-(2-Py) | 2-Me, 5-Me | 3 | —Si(Me)₂— |
| 277 | Zr | Cl | 3-(2-BzFu) | 4-Me, 5-Me | 3 | 3-(2-BzFu) | 4-Me, 5-Me | 3 | —Si(Me)₂— |
| 278 | Zr | Cl | 3-(2-BzFu) | 2-Me, 5-Me | 3 | 3-(2-BzFu) | 2-Me, 5-Me | 3 | —Si(Me)₂— |
| 279 | Zr | Cl | 3-[2-(N-Me-Pyr)] | 4-Me, 5-Me | 3 | 3-[2-(N-Me-Pyr)] | 4-Me, 5-Me | 3 | —Si(Me)₂— |
| 280 | Zr | Cl | 3-[2-(N-Me-Pyr)] | 2-Me, 5-Me | 3 | 3-[2-(N-Me-Pyr)] | 2-Me, 5-Me | 3 | —Si(Me)₂— |

TABLE 9

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 281 | Zr | Cl | 3-(2-Fu) | — | 1 | 3-(2-Fu) | — | 1 | —GeH₂— |
| 282 | Zr | Cl | 3-(2-Fu) | — | 1 | 3-(2-Fu) | — | 1 | —Ge(Me)₂— |
| 283 | Zr | Cl | 3-(2-Fu) | 5-Me | 2 | 3-(2-Fu) | 5-Me | 2 | —Ge(Me)₂— |
| 284 | Zr | Cl | 3-(2-Fu) | 4-Me | 2 | 3-(2-Fu) | 4-Me | 2 | —Ge(Me)₂— |
| 285 | Zr | Cl | 3-(2-Fu) | 4-OMe | 2 | 3-(2-Fu) | 4-OMe | 2 | —Ge(Me)₂— |
| 286 | Zr | Cl | 3-(2-Fu) | 4-OPh | 2 | 3-(2-Fu) | 4-OPh | 2 | —Ge(Me)₂— |
| 287 | Zr | Cl | 3-(2-Fu) | 4-Bzl | 2 | 3-(2-Fu) | 4-Bzl | 2 | —Ge(Me)₂— |
| 288 | Zr | Cl | 3-(2-Fu) | 4-Tol | 2 | 3-(2-Fu) | 4-Tol | 2 | —Ge(Me)₂— |
| 289 | Zr | Cl | 3-(2-Fu) | 4-OBzl | 2 | 3-(2-Fu) | 4-OBzl | 2 | —Ge(Me)₂— |
| 290 | Zr | Cl | 3-(2-Fu) | 4-TMS | 2 | 3-(2-Fu) | 4-TMS | 2 | —Ge(Me)₂— |
| 291 | Zr | Cl | 3-(2-Fu) | 4-(1-Pyr) | 2 | 3-(2-Fu) | 4-(1-Pyr) | 2 | —Ge(Me)₂— |
| 292 | Zr | Cl | 3-(2-Fu) | 4-(1-Indo) | 2 | 3-(2-Fu) | 4-(1-Indo) | 2 | —Ge(Me)₂— |
| 293 | Zr | Cl | 3-(2-Fu) | 2-Me | 2 | 3-(2-Fu) | 2-Me | 2 | —Ge(Me)₂— |
| 294 | Zr | Cl | 3-(2-Fu) | 4-Me, 5-Me | 3 | 3-(2-Fu) | 2-Me, 5-Me | 3 | —Ge(Me)₂— |
| 295 | Zr | Cl | 3-(2-Fu) | 4-Me, 5-Me | 3 | 3-(2-Fu) | 4-Me, 5-Me | 3 | —Ge(Me)₂— |
| 296 | Zr | Cl | 3-(2-Fu) | 4-Et, 5-Me | 3 | 3-(2-Fu) | 4-Et, 5-Me | 3 | —Ge(Me)₂— |
| 297 | Zr | Cl | 3-(2-Fu) | 4-(i-Pr), 5-Me | 3 | 3-(2-Fu) | 4-(i-Pr), 5-Me | 3 | —Ge(Me)₂— |
| 298 | Zr | Cl | 3-(2-Fu) | 4-(t-Bu), 5-Me | 3 | 3-(2-Fu) | 4-(t-Bu), 5-Me | 3 | —Ge(Me)₂— |
| 299 | Zr | Cl | 3-(2-Fu) | 4-Ph, 5-Me | 3 | 3-(2-Fu) | 4-Ph, 5-Me | 3 | —Ge(Me)₂— |
| 300 | Zr | Cl | 3-(2-Fu) | 2-Ph, 5-Me | 3 | 3-(2-Fu) | 2-Ph, 5-Me | 3 | —Ge(Me)₂— |
| 301 | Zr | Cl | 3-(2-Fu) | 4-Me, 5-Me | 3 | 3-(2-Fu) | 4-Me, 5-Me | 3 | —Ge(Me)₂— |
| 302 | Zr | Cl | 3-(2-Fu) | 4-Me, 5-Me | 3 | 3-(2-Fu) | 4-Me, 5-Me | 3 | —Ge(Me)₂— |
| 303 | Zr | Me | 3-(2-Fu) | 4-Me, 5-Me | 3 | 3-(2-Fu) | 4-Me, 5-Me | 3 | —Ge(Me)₂— |
| 304 | Zr | Bzl | 3-(2-Fu) | 4-Me, 5-Me | 3 | 3-(2-Fu) | 4-Me, 5-Me | 3 | —Ge(Me)₂— |
| 305 | Hf | Cl | 3-(2-Fu) | 4-Me, 5-Me | 3 | 3-(2-Fu) | 4-Me, 5-Me | 3 | —Ge(Me)₂— |
| 306 | Ti | Cl | 3-(2-Fu) | 4-Me, 5-Me | 3 | 3-(2-Fu) | 4-Me, 5-Me | 3 | —Ge(Me)₂— |
| 307 | Hf | Cl | 3-(2-Fu) | 2-Me, 5-Me | 3 | 3-(2-Fu) | 2-Me, 5-Me | 3 | —Ge(Me)₂— |
| 308 | Ti | Cl | 3-(2-Fu) | 2-Me, 5-Me | 3 | 3-(2-Fu) | 2-Me, 5-Me | 3 | —Ge(Me)₂— |
| 309 | Zr | Cl | 3-(3-Fu) | 4-Me, 5-Me | 3 | 3-(3-Fu) | 4-Me, 5-Me | 3 | —Ge(Me)₂— |
| 310 | Zr | Cl | 3-(3-Fu) | 2-Me, 5-Me | 3 | 3-(3-Fu) | 2-Me, 5-Me | 3 | —Ge(Me)₂— |
| 311 | Zr | Cl | 3-[2-(3-Me-Fu)] | 4-Me, 5-Me | 3 | 3-[2-(3-Me-Fu)] | 4-Me, 5-Me | 3 | —Ge(Me)₂— |
| 312 | Zr | Cl | 3-[2-(3-Me-Fu)] | 2-Me, 5-Me | 3 | 3-[2-(3-Me-Fu)] | 2-Me, 5-Me | 3 | —Ge(Me)₂— |
| 313 | Zr | Cl | 3-(2-Thie) | 4-Me, 5-Me | 3 | 3-(2-Thie) | 4-Me, 5-Me | 3 | —Ge(Me)₂— |
| 314 | Zr | Cl | 3-(2-Thie) | 2-Me, 5-Me | 3 | 3-(2-Thie) | 2-Me, 5-Me | 3 | —Ge(Me)₂— |
| 315 | Zr | Cl | 3-(2-Py) | 4-Me, 5-Me | 3 | 3-(2-Py) | 4-Me, 5-Me | 3 | —Ge(Me)₂— |
| 316 | Zr | Cl | 3-(2-Py) | 2-Me, 5-Me | 3 | 3-(2-Py) | 2-Me, 5-Me | 3 | —Ge(Me)₂— |
| 317 | Zr | Cl | 3-(2-BzFu) | 4-Me, 5-Me | 3 | 3-(2-BzFu) | 4-Me, 5-Me | 3 | —Ge(Me)₂— |
| 318 | Zr | Cl | 3-(2-BzFu) | 2-Me, 5-Me | 3 | 3-(2-BzFu) | 2-Me, 5-Me | 3 | —Ge(Me)₂— |
| 319 | Zr | Cl | 3-[2-(N-Me-Pyr)] | 4-Me, 5-Me | 3 | 3-[2-(N-Me-Pyr)] | 4-Me, 5-Me | 3 | —Ge(Me)₂— |
| 320 | Zr | Cl | 3-[2-(N-Me-Pyr)] | 2-Me, 5-Me | 3 | 3-[2-(N-Me-Pyr)] | 2-Me, 5-Me | 3 | —Ge(Me)₂— |

TABLE 10

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 321 | Zr | Cl | 2-(2-Fu) | — | 1 | 2-(2-Fu) | — | 1 | —CH₂— |
| 322 | Zr | Cl | 2-(2-Fu) | — | 1 | 2-(2-Fu) | — | 1 | —C(Me)₂— |

TABLE 10-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 323 | Zr | Cl | 2-(2-Fu) | 7-Me | 2 | 2-(2-Fu) | 5-Me | 2 | —C(Me)$_2$— |
| 324 | Zr | Cl | 2-(2-Fu) | 4-Me | 2 | 2-(2-Fu) | 4-Me | 2 | —C(Me)$_2$— |
| 325 | Zr | Cl | 2-(2-Fu) | 3-Me | 2 | 2-(2-Fu) | 4-OMe | 2 | —C(Me)$_2$— |
| 326 | Zr | Cl | 2-(2-Fu) | 3-Me, 7-Me | 3 | 2-(2-Fu) | 4-OPh | 3 | —C(Me)$_2$— |
| 327 | Zr | Cl | 2-(2-Fu) | 4-Me, 7-Me | 3 | 2-(2-Fu) | 4-Bzl | 3 | —C(Me)$_2$— |
| 328 | Zr | Cl | 2-(2-Fu) | 4-Cl | 2 | 2-(2-Fu) | 4-Tol | 2 | —C(Me)$_2$— |
| 329 | Zr | Cl | 2-(2-Fu) | 4-Et | 2 | 2-(2-Fu) | 4-OBzl | 2 | —C(Me)$_2$— |
| 330 | Zr | Cl | 2-(2-Fu) | 4-i-Pr | 2 | 2-(2-Fu) | 4-TMS | 2 | —C(Me)$_2$— |
| 331 | Zr | Cl | 2-(2-Fu) | 4-t-Bu | 2 | 2-(2-Fu) | 4-(1-Pyr) | 2 | —C(Me)$_2$— |
| 332 | Zr | Cl | 2-(2-Fu) | 4-Ph | 2 | 2-(2-Fu) | 4-(1-Indo) | 2 | —C(Me)$_2$— |
| 333 | Zr | Cl | 2-(2-Fu) | 4-Np | 2 | 2-(2-Fu) | 2-Me | 2 | —C(Me)$_2$— |
| 334 | Zr | Cl | 2-(2-Fu) | 4-OMe | 2 | 2-(2-Fu) | 2-Me, 5-Me | 2 | —C(Me)$_2$— |
| 335 | Zr | Cl | 2-(2-Fu) | 4-OPh | 2 | 2-(2-Fu) | 4-Me, 5-Me | 2 | —C(Me)$_2$— |
| 336 | Zr | Cl | 2-(2-Fu) | 4-Bzl | 2 | 2-(2-Fu) | 4-Et, 5-Me | 2 | —C(Me)$_2$— |
| 337 | Zr | Cl | 2-(2-Fu) | 4-Tol | 2 | 2-(2-Fu) | 4-(i-Pr), 5-Me | 2 | —C(Me)$_2$— |
| 338 | Zr | Cl | 2-(2-Fu) | 4-Obzl | 2 | 2-(2-Fu) | 4-(t-Bu), 5-Me | 2 | —C(Me)$_2$— |
| 339 | Zr | Cl | 2-(2-Fu) | 4-TMS | 2 | 2-(2-Fu) | 4-Ph, 5-Me | 2 | —C(Me)$_2$— |
| 340 | Zr | Cl | 2-(2-Fu) | 4-(1-Pyr) | 2 | 2-(2-Fu) | 2-Ph, 5-Me | 2 | —C(Me)$_2$— |
| 341 | Zr | Cl | 2-(2-Fu) | 4-(1-Indo) | 2 | 2-(2-Fu) | 4-Me, 5-Me | 2 | —C(Me)$_2$— |
| 342 | Zr | Cl | 2-(2-Fu), 4-(2-Fu) | — | 2 | 2-(2-Fu) | 4-Me, 5-Me | 2 | —C(Me)$_2$— |
| 343 | Zr | Me | 2-(2-Fu), 4-(2-Thie) | — | 2 | 2-(2-Fu) | 4-Me, 5-Me | 2 | —C(Me)$_2$— |
| 344 | Zr | Bzl | 2-(2-Fu), 4-(2-BzFu) | — | 2 | 2-(2-Fu) | 4-Me, 5-Me | 2 | —C(Me)$_2$— |
| 345 | Hf | Cl | 2-(2-Fu), 4-(2-Py) | — | 2 | 2-(2-Fu) | 4-Me, 5-Me | 2 | —C(Me)$_2$— |
| 346 | Ti | Cl | 2-(2-Fu), 4-(1-MePyr) | — | 2 | 2-(2-Fu) | 4-Me, 5-Me | 2 | —C(Me)$_2$— |
| 347 | Hf | Cl | 2-(2-Fu) | 4-Et, 7-Et | 3 | 2-(2-Fu) | 2-Me, 5-Me | 3 | —C(Me)$_2$— |
| 348 | Ti | Cl | 2-(2-Fu) | 4-i-Pr, 7-i-Pr | 3 | 2-(2-Fu) | 2-Me, 5-Me | 3 | —C(Me)$_2$— |
| 349 | Zr | Cl | 2-(2-Fu) | 4-t-Bu, 7-t-Bu | 3 | 2-(2-Fu) | 4-Me, 5-Me | 3 | —C(Me)$_2$— |
| 350 | Zr | Cl | 2-(2-Fu) | 4-Ph, 7-Me | 3 | 2-(2-Fu) | 2-Me, 5-Me | 3 | —C(Me)$_2$— |
| 351 | Zr | Cl | 2-(2-Fu) | 3-Ph, 7-Me | 3 | 2-(2-Fu) | 4-Me, 5-Me | 3 | —C(Me)$_2$— |
| 352 | Zr | Cl | 2-(2-Fu) | 4-Me, 7-Me | 3 | 2-(2-Fu) | 2-Me, 5-Me | 3 | —C(Me)$_2$— |
| 353 | Zr | Cl | 2-(2-Fu) | 4-Me, 7-Me | 3 | 2-(2-Fu) | 4-Me, 5-Me | 3 | —C(Me)$_2$— |
| 354 | Zr | Cl | 2-(2-Fu) | 4-Ph | 2 | 2-(2-Fu) | 2-Me, 5-Me | 2 | —C(Me)$_2$— |
| 355 | Zr | Cl | 2-(2-Fu) | 4-Ph | 2 | 2-(2-Fu) | 4-Me, 5-Me | 2 | —C(Me)$_2$— |
| 356 | Zr | Cl | 2-(2-Fu) | 4-Ph | 2 | 2-(2-Fu) | 2-Me, 5-Me | 2 | —C(Me)$_2$— |
| 357 | Zr | Cl | 2-(2-Fu) | 4-Ph | 2 | 2-(2-Fu) | 4-Me, 5-Me | 2 | —C(Me)$_2$— |
| 358 | Zr | Cl | 2-(2-Fu) | 3-Me, 7-Me | 3 | 2-(2-Fu) | 2-Me, 5-Me | 3 | —C(Me)$_2$— |
| 359 | Zr | Cl | 2-(2-Fu) | 3-Me, 7-Me | 3 | 2-(2-Fu) | 4-Me, 5-Me | 3 | —C(Me)$_2$— |
| 360 | Zr | Cl | 2-(3-Fu) | 4-Ph | 2 | 2-(3-Fu) | 2-Me, 5-Me | 2 | —C(Me)$_2$— |
| 361 | Zr | Cl | 2-(3-Fu) | 4-Ph | 2 | 2-(3-Fu) | 4-Ph | 2 | —C(Me)$_2$— |
| 362 | Zr | Cl | 2-[2-(3-Me-Fu)] | 4-Ph | 2 | 2-[2-(3-Me-Fu)] | 4-Ph | 2 | —C(Me)$_2$— |
| 363 | Zr | Cl | 2-[2-(3-Me-Fu)] | — | 1 | 2-[2-(3-Me-Fu)] | — | 1 | —C(Me)$_2$— |
| 364 | Zr | Cl | 2-(2-Thie) | 4-Ph | 2 | 2-(2-Thie) | 4-Ph | 2 | —C(Me)$_2$— |
| 365 | Zr | Cl | 2-(2-Thie) | — | 1 | 2-(2-Thie) | — | 1 | —C(Me)$_2$— |
| 366 | Zr | Cl | 2-(2-Py) | 4-Ph | 2 | 2-(2-Py) | 4-Ph | 2 | —C(Me)$_2$— |
| 367 | Zr | Cl | 2-(2-Py) | — | 1 | 2-(2-Py) | — | 1 | —C(Me)$_2$— |
| 368 | Zr | Cl | 2-(2-BzFu) | 4-Ph | 2 | 2-(2-BzFu) | 4-Ph | 2 | —C(Me)$_2$— |
| 369 | Zr | Cl | 2-(2-BzFu) | — | 1 | 2-(2-BzFu) | — | 1 | —C(Me)$_2$— |
| 370 | Zr | Cl | 2-[2-(1-Me-Pyr)] | 4-Ph | 2 | 2-[2-(1-Me-Pyr)] | 4-Ph | 2 | —C(Me)$_2$— |
| 371 | Zr | Cl | 2-[2-(1-Me-Pyr)] | — | 1 | 2-[2-(1-Me-Pyr)] | — | 1 | —C(Me)$_2$— |

TABLE 11

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 372 | Zr | Cl | 2-(2-Fu) | — | 1 | 2-(2-Fu) | — | 1 | —CH$_2$CH$_2$— |
| 373 | Zr | Cl | 2-(2-Fu) | — | 1 | 2-(2-Fu) | — | 1 | —C$_2$(Me)$_4$— |
| 374 | Zr | Cl | 2-(2-Fu) | 7-Me | 2 | 2-(2-Fu) | 7-Me | 2 | —C$_2$(Me)$_4$— |
| 375 | Zr | Cl | 2-(2-Fu) | 4-Me | 2 | 2-(2-Fu) | 4-Me | 2 | —C$_2$(Me)$_4$— |
| 376 | Zr | Cl | 2-(2-Fu) | 3-Me | 2 | 2-(2-Fu) | 3-Me | 2 | —C$_2$(Me)$_4$— |
| 377 | Zr | Cl | 2-(2-Fu) | 3-Me, 7-Me | 2 | 2-(2-Fu) | 3-Me, 7-Me | 3 | —C$_2$(Me)$_4$— |
| 378 | Zr | Cl | 2-(2-Fu) | 4-Me, 7-Me | 2 | 2-(2-Fu) | 4-Me, 7-Me | 3 | —C$_2$(Me)$_4$— |
| 379 | Zr | Cl | 2-(2-Fu) | 4-Cl | 2 | 2-2-Fu) | 4-Cl | 2 | —C$_2$(Me)$_4$— |
| 380 | Zr | Cl | 2-(2-Fu) | 4-Et | 2 | 2-(2-Fu) | 4-Et | 2 | —C$_2$(Me)$_4$— |
| 381 | Zr | Cl | 2-(2-Fu) | 4-i-Pr | 2 | 2-(2-Fu) | 4-i-Pr | 2 | —C$_2$(Me)$_4$— |
| 382 | Zr | Cl | 2-(2-Fu) | 4-t-Bu | 2 | 2-(2-Fu) | 4-t-Bu | 2 | —C$_2$(Me)$_4$— |
| 383 | Zr | Cl | 2-(2-Fu) | 4-Ph | 2 | 2-(2-Fu) | 4-Ph | 2 | —C$_2$(Me)$_4$— |
| 384 | Zr | Cl | 2-(2-Fu) | 2-Np | 2 | 2-(2-Fu) | 2-Np | 2 | —C$_2$(Me)$_4$— |
| 385 | Zr | Cl | 2-(2-Fu) | 2-OMe | 2 | 2-(2-Fu) | 2-OMe | 2 | —C$_2$(Me)$_4$— |
| 386 | Zr | Cl | 2-(2-Fu) | 4-Oph | 2 | 2-(2-Fu) | 4-Oph | 2 | —C$_2$(Me)$_4$— |
| 387 | Zr | Cl | 2-(2-Fu) | 4-Bzl | 2 | 2-(2-Fu) | 4-Bzl | 2 | —C$_2$(Me)$_4$— |
| 388 | Zr | Cl | 2-(2-Fu) | 4-Tol | 2 | 2-(2-Fu) | 4-Tol | 2 | —C$_2$(Me)$_4$— |
| 389 | Zr | Cl | 2-(2-Fu) | 4-OBzl | 2 | 2-(2-Fu) | 4-Obzl | 2 | —C$_2$(Me)$_4$— |

TABLE 11-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 390 | Zr | Cl | 2-(2-Fu) | 4-TMS | 2 | 2-(2-Fu) | 4-TMS | 2 | —C$_2$(Me)$_4$— |
| 391 | Zr | Cl | 2-(2-Fu) | 4-(1-Pyr) | 2 | 2-(2-Fu) | 4-(1-Pyr) | 2 | —C$_2$(Me)$_4$— |
| 392 | Zr | Cl | 2-(2-Fu) | 4-(1-Indo) | 2 | 2-(2-Fu) | 4-(1-Indo) | 2 | —C$_2$(Me)$_4$— |
| 393 | Zr | Cl | 2-(2-Fu), (4-(2-Fu) | — | 2 | 2-(2-Fu), 4-(2-Fu) | — | 2 | —C$_2$(Me)$_4$— |
| 394 | Zr | Me | 2-(2-Fu), 4-(2-Thie) | — | 2 | 2-(2-Fu), 4-(2-Thie) | — | 2 | —C$_2$(Me)$_4$— |
| 395 | Zr | Bzl | 2-(2-Fu), 4-(2-BzFu) | — | 2 | 2-(2-Fu), 4-(2-BzFu) | — | 2 | —C$_2$(Me)$_4$— |
| 396 | Hf | Cl | 2-(2-Fu), 4-(2-Py) | — | 2 | 2-(2-Fu), 4-(2-Py) | — | 2 | —C$_2$(Me)$_4$— |
| 397 | Ti | Cl | 2-(2-Fu), 4-(1-MePyr) | — | 2 | 2-(2-Fu), 4-(1-MePyr) | — | 2 | —C$_2$(Me)$_4$— |
| 398 | Hf | Cl | 2-(2-Fu) | 4-Et, 7-Et | 3 | 2-(2-Fu) | 4-Et, 7-Et | 3 | —C$_2$(Me)$_4$— |
| 399 | Ti | Cl | 2-(2-Fu) | 4-i-Pr, 7-i-Pr | 3 | 2-(2-Fu) | 4-i-Pr, 7-i-Pr | 3 | —C$_2$(Me)$_4$— |
| 400 | Zr | Cl | 2-(2-Fu) | 4-t-Bu, 7-t-Bu | 3 | 2-(2-Fu) | 4-t-Bu, 7-t-Bu | 3 | —C$_2$(Me)$_4$— |
| 401 | Zr | Cl | 2-(2-Fu) | 4-Ph, 7-Ph | 3 | 2-(2-Fu) | 4-Ph, 7-Ph | 3 | —C$_2$(Me)$_4$— |
| 402 | Zr | Cl | 2-(2-Fu) | 3-Ph, 7-Me | 3 | 2-(2-Fu) | 3-Ph, 7-Me | 3 | —C$_2$(Me)$_4$— |
| 403 | Zr | Cl | 2-(2-Fu) | 4-Me, 7-Me | 3 | 2-2-(2-Fu) | 4-Me, 7-Me | 3 | —C$_2$(Me)$_4$— |
| 404 | Zr | Cl | 2-(2-Fu) | 4-Me, 7-Me | 3 | 2-(2-Fu) | 4-Me, 7-Me | 3 | —C$_2$(Me)$_4$— |
| 405 | Zr | Me | 2-(2-Fu) | 4-Ph | 2 | 2-(2-Fu) | 4-Ph | 2 | —C$_2$(Me)$_4$— |
| 406 | Zr | Bzl | 2-(2-Fu) | 4-Ph | 2 | 2-(2-Fu) | 4-Ph | 2 | —C$_2$(Me)$_4$— |
| 407 | Hf | Cl | 2-(2-Fu) | 4-Ph | 2 | 2-(2-Fu) | 4-Ph | 2 | —C$_2$(Me)$_4$— |
| 408 | Ti | Cl | 2-(2-Fu) | 4-Ph | 2 | 2-(2-Fu) | 4-Ph | 2 | —C$_2$(Me)$_4$— |
| 409 | Hf | Cl | 2-(2-Fu) | 3-Me, 7-Me | 3 | 2-(2-Fu) | 3-Me, 7-Me | 3 | —C$_2$(Me)$_4$— |
| 410 | Ti | Cl | 2-(2-Fu) | 3-Me, 7-Me | 3 | 2-(2-Fu) | 3-Me, 7-Me | 3 | —C$_2$(Me)$_4$— |
| 411 | Zr | Cl | 2-(3-Fu) | 4-Ph | 2 | 2-(3-Fu) | 4-Ph | 2 | —C$_2$(Me)$_4$— |
| 412 | Zr | Cl | 2-(3-Fu) | 4-Ph | 2 | 2-(3-Fu) | 4-Ph | 2 | —C$_2$(Me)$_4$— |
| 413 | Zr | Cl | 2-[(3-Me-Fu)] | 4-Ph | 2 | 2-[2-(3-Me-Fu)] | 4-Ph | 2 | —C$_2$(Me)$_4$— |
| 414 | Zr | Cl | 2-[(3-Me-Fu)] | — | 1 | 2-[2-(3-Me-Fu)] | — | 1 | —C$_2$(Me)$_4$— |
| 415 | Zr | Cl | 2-(2-Thie) | 4-Ph | 2 | 2-(2-Thie) | 4-Ph | 2 | —C$_2$(Me)$_4$— |
| 416 | Zr | Cl | 2-(2-Thie) | — | 1 | 2-(2-Thie) | — | 1 | —C$_2$(Me)$_4$— |
| 417 | Zr | Cl | 2-(2-Py) | 4-Ph | 2 | 2-(2-Py) | 4-Ph | 2 | —C$_2$(Me)$_4$— |
| 418 | Zr | Cl | 2-(2-Py) | — | 1 | 2-(2-Py) | — | 1 | —C$_2$(Me)$_4$— |
| 419 | Zr | Cl | 2-(2-BzFu) | 4-Ph | 2 | 2-(2-BzFu) | 4-Ph | 2 | —C$_2$(Me)$_4$— |
| 420 | Zr | Cl | 2-(2-BsFu) | — | 1 | 2-(2-BsFu) | — | 1 | —C$_2$(Me)$_4$— |
| 421 | Zr | Cl | 2-[2-(1-Me-Pyr)] | 4-Ph | 2 | 2-[2-(1-Me-Pyr)] | 4-Ph | 2 | —C$_2$(Me)$_4$— |
| 422 | Zr | Cl | 2-[2-(1-Me-Pyr)] | — | 1 | 2-[2-(1-Me-Pyr)] | — | 1 | —C$_2$(Me)$_4$— |

TABLE 12

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 423 | Zr | Cl | 2-(2-Fu) | — | 1 | 3-(2-Fu) | — | 1 | —SiH$_2$— |
| 424 | Zr | Cl | 2-(2-Fu) | — | 1 | 2-(2-Fu) | — | 1 | —Si(Me)$_2$— |
| 425 | Zr | Cl | 2-(2-Fu) | 7-Me | 2 | 2-(2-Fu) | 7-Me | 2 | —Si(Me)$_2$— |
| 426 | Zr | Cl | 2-(2-Fu) | 4-Me | 2 | 2-(2-Fu) | 4-Me | 2 | —Si(Me)$_2$— |
| 427 | Zr | Cl | 2-(2-Fu) | 3-Me | 2 | 2-(2-Fu) | 3-Me | 2 | —Si(Me)$_2$— |
| 428 | Zr | Cl | 2-(2-Fu) | 3-Me, 7-Me | 3 | 2-(2-Fu) | 3-Me, 7-Me | 2 | —Si(Me)$_2$— |
| 429 | Zr | Cl | 2-(2-Fu) | 4-Me, 7-Me | 3 | 2-(2-Fu) | 3-Me, 7-Me | 2 | —Si(Me)$_2$— |
| 430 | Zr | Cl | 2-(2-Fu) | 4-Cl | 2 | 2-(2-Fu) | 4-Cl | 2 | —Si(Me)$_2$— |
| 431 | Zr | Cl | 2-(2-Fu) | 4-Et | 2 | 2-(2-Fu) | 4-Me, 7-Me | 2 | —Si(Me)$_2$— |
| 432 | Zr | Cl | 2-(2-Fu) | 4-i-Pr | 2 | 2-(2-Fu) | 4-i-Pr | 2 | —Si(Me)$_2$— |
| 433 | Zr | Cl | 2-(2-Fu) | 4-t-Bu | 2 | 2-(2-Fu) | 4-t-Bu | 2 | —Si(Me)$_2$— |
| 434 | Zr | Cl | 2-(2-Fu) | 4-Ph | 2 | 2-(2-Fu) | 4-Ph | 2 | —Si(Me)$_2$— |
| 435 | Zr | Cl | 2-(2-Fu) | 4-Np | 2 | 2-(2-Fu) | 4-Np | 2 | —Si(Me)$_2$— |
| 436 | Zr | Cl | 2-(2-Fu) | 4-OMe | 2 | 2-(2-Fu) | 4-OMe | 2 | —Si(Me)$_2$— |
| 437 | Zr | Cl | 2-(2-Fu) | 4-OPh | 2 | 2-(2-Fu) | 4-OPh | 2 | —Si(Me)$_2$— |
| 438 | Zr | Cl | 2-(2-Fu) | 4-Bzl | 2 | 2-(2-Fu) | 4-Bzl | 2 | —Si(Me)$_2$— |
| 439 | Zr | Cl | 2-(2-Fu) | 4-Tol | 2 | 2-(2-Fu) | 4-Tol | 2 | —Si(Me)$_2$— |
| 440 | Zr | Cl | 2-(2-Fu) | 4-(OBzl) | 2 | 2-(2-Fu) | 4-(OBzl) | 2 | —Si(Me)$_2$— |
| 441 | Zr | Cl | 2-(2-Fu) | 4-TMS | 2 | 2-(2-Fu) | 4-TMS | 2 | —Si(Me)$_2$— |
| 442 | Zr | Cl | 2-(2-Fu) | 4-(1-Pyr) | 2 | 2-(2-Fu) | 4-(1-Pyr) | 2 | —Si(Me)$_2$— |
| 443 | Zr | Cl | 2-(2-Fu) | 4-(1-Indo) | 2 | 2-(2-Fu) | 4-(1-Indo) | 2 | —Si(Me)$_2$— |
| 444 | Zr | Cl | 2-(2-Fu), 4-(2-Fu) | — | 2 | 2-(2-Fu), 4-(2-Fu) | — | 2 | —Si(Me)$_2$— |
| 445 | Zr | Me | 2-(2-Fu), 4-(2-Thie) | — | 2 | 2-(2-Fu), 4-(2-Thie) | — | 2 | —Si(Me)$_2$— |
| 446 | Zr | Bzl | 2-(2-Fu), 4-(2-BzFu) | — | 2 | 2-(2-Fu), 4-(2-BzFu) | — | 2 | —Si(Me)$_2$— |
| 447 | Hf | Cl | 2-(2-Fu), 4-(2-Py) | — | 2 | 2-(2-Fu), 4-(2-Py) | — | 2 | —Si(Me)$_2$— |
| 448 | Ti | Cl | 2-(2-Fu), 4-(1-MePyr) | — | 2 | 2-(2-Fu), 4-(1-MePyr) | — | 2 | —Si(Me)$_2$— |
| 449 | Hf | Cl | 2-(2-Fu) | 4-Et, 7-Et | 3 | 2-(2-Fu) | 4-Et, 7-Et | 3 | —Si(Me)$_2$— |
| 450 | Ti | Cl | 2-(2-Fu) | 4-i-Pr, 7-i-Pr | 3 | 2-(2-Fu) | 4-i-Pr, 7-i-Pr | 3 | —Si(Me)$_2$— |
| 451 | Zr | Cl | 2-(2-Fu) | 4-t-Bu, 7-t-Bu | 3 | 2-(2-Fu) | 4-t-Bu, 7-t-Bu | 3 | —Si(Me)$_2$— |
| 452 | Zr | Cl | 2-(2-Fu) | 4-Ph, 7-Ph | 3 | 2-(2-Fu) | 4-Ph, 7-Ph | 3 | —Si(Me)$_2$— |
| 453 | Zr | Cl | 2-(2-Fu) | 3-Ph, 7-Me | 3 | 2-(2-Fu) | 3-Ph, 7-Me | 3 | —Si(Me)$_2$— |
| 454 | Zr | Cl | 2-(2-Fu) | 4-Me, 7-Me | 3 | 2-(2-Fu) | 4-Me, 7-Me | 3 | —Si(Me)$_2$— |
| 455 | Zr | Cl | 2-(2-Fu) | 4-Me, 7-Me | 3 | 2-(2-Fu) | 4-Me, 7-Me | 2 | —Si(Me)$_2$— |
| 456 | Zr | Me | 2-(2-Fu) | 4-Ph | 2 | 2-(2-Fu) | 4-Ph | 2 | —Si(Me)$_2$— |

TABLE 12-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 457 | Zr | Bzl | 2-(2-Fu) | 4-Ph | 2 | 2-(2-Fu) | 4-Ph | 2 | —Si(Me)₂— |
| 458 | Hf | Cl | 2-(2-Fu) | 4-Ph | 2 | 2-(2-Fu) | 4-Ph | 2 | —Si(Me)₂— |
| 459 | Ti | Cl | 2-(2-Fu) | 4-Ph | 2 | 2-(2-Fu) | 4-Ph | 2 | —Si(Me)₂— |
| 460 | Hf | Cl | 2-(2-Fu) | 3-Me, 7-Me | 3 | 2-(2-Fu) | 3-Me, 7-Me | 3 | —Si(Me)₂— |
| 461 | Ti | Cl | 2-(2-Fu) | 3-Me, 7-Me | 3 | 2-(2-Fu) | 3-Me, 7-Me | 3 | —Si(Me)₂— |
| 462 | Zr | Cl | 2-(3-Fu) | 4-Ph | 2 | 2-(3-Fu) | 4-Ph | 2 | —Si(Me)₂— |
| 463 | Zr | Cl | 2-(3-Fu) | 4-Ph | 2 | 2-(3-Fu) | 4-Ph | 2 | —Si(Me)₂— |
| 464 | Zr | Cl | 2-[2-(3-Me-Fu)] | 4-Ph | 2 | 2-[2-(3-Me-Fu)] | 4-Ph | 2 | —Si(Me)₂— |
| 465 | Zr | Cl | 2-[2-(3-Me-Fu)] | — | 1 | 2-[2-(3-Me-Fu)] | — | 1 | —Si(Me)₂— |
| 466 | Zr | Cl | 2-(2-Thie) | 4-Ph | 2 | 2-(2-Thie) | 4-Ph | 2 | —Si(Me)₂— |
| 467 | Zr | Cl | 2-(2-Thie) | — | 1 | 2-(2-Thie) | — | 1 | —Si(Me)₂— |
| 468 | Zr | Cl | 2-(2-Py) | 4-Ph | 2 | 2-(2-Py) | 4-Ph | 2 | —Si(Me)₂— |
| 469 | Zr | Cl | 2-(2-(Py) | — | 1 | 2-(2-Py) | — | 1 | —Si(Me)₂— |
| 470 | Zr | Cl | 2-(2-BzFu) | 4-Ph | 2 | 2-(2-(BzFu) | 4-Ph | 2 | —Si(Me)₂— |
| 471 | Zr | Cl | 2-(2-BzFu) | — | 1 | 2-(2-(BzFu) | — | 1 | —Si(Me)₂— |
| 472 | Zr | Cl | 2-[2-(1-Me-Pyr)] | 4-Ph | 2 | 2-[2-(1-Me-Pyr)] | 4-Ph | 2 | —Si(Me)₂— |
| 473 | Zr | Cl | 2-[2-(1-Me-Pyr)] | — | 1 | 2-[2-(1-Me-Pyr)] | — | 1 | —Si(Me)₂— |

TABLE 13

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 474 | Zr | Cl | 2-(2-Fu) | — | 1 | 3-(2-Fu) | — | 1 | —GeH₂— |
| 475 | Zr | Cl | 2-(2-Fu) | — | 1 | 2-(2-Fu) | — | 1 | —Ge(Me)₂— |
| 476 | Zr | Cl | 2-(2-Fu) | 7-Me | 2 | 2-(2-Fu) | 7-Me | 2 | —Ge(Me)₂— |
| 477 | Zr | Cl | 2-(2-Fu) | 4-Me | 2 | 2-(2-Fu) | 4-Me | 2 | —Ge(Me)₂— |
| 478 | Zr | Cl | 2-(2-Fu) | 3-Me | 2 | 2-(2-Fu) | 3-Me | 2 | —Ge(Me)₂— |
| 479 | Zr | Cl | 2-(2-Fu) | 3-Me, 7-Me | 3 | 2-(2-Fu) | 3-Me, 7-Me | 3 | —Ge(Me)₂— |
| 480 | Zr | Cl | 2-(2-Fu) | 4-Me, 7-Me | 3 | 2-(2-Fu) | 3-Me, 7-Me | 3 | —Ge(Me)₂— |
| 481 | Zr | Cl | 2-(2-Fu) | 4-Cl | 2 | 2-(2-Fu) | 4-Me, 7-Me | 2 | —Ge(Me)₂— |
| 482 | Zr | Cl | 2-(2-Fu) | 4-Et | 2 | 2-(2-Fu) | 4-Cl | 2 | —Ge(Me)₂— |
| 483 | Zr | Cl | 2-(2-Fu) | 4-i-Pr | 2 | 2-(2-Fu) | 4-i-Pr | 2 | —Ge(Me)₂— |
| 484 | Zr | Cl | 2-(2-Fu) | 4-t-Bu | 2 | 2-(2-Fu) | 4-t-Bu | 2 | —Ge(Me)₂— |
| 485 | Zr | Cl | 2-(2-Fu) | 4-Ph | 2 | 2-(2-Fu) | 4-Ph | 2 | —Ge(Me)₂— |
| 486 | Zr | Cl | 2-(2-Fu) | 4-Np | 2 | 2-(2-Fu) | 4-Np | 2 | —Ge(Me)₂— |
| 487 | Zr | Cl | 2-(2-Fu) | 4-OMe | 2 | 2-(2-Fu) | 4-OMe | 2 | —Ge(Me)₂— |
| 488 | Zr | Cl | 2-(2-Fu) | 4-OPh | 2 | 2-(2-Fu) | 4-OPh | 2 | —Ge(Me)₂— |
| 489 | Zr | Cl | 2-(2-Fu) | 4-Bzl | 2 | 2-(2-Fu) | 4-Bzl | 2 | —Ge(Me)₂— |
| 490 | Zr | Cl | 2-(2-Fu) | 4-Tol | 2 | 2-(2-Fu) | 4-Tol | 2 | —Ge(Me)₂— |
| 491 | Zr | Cl | 2-(2-Fu) | 4-(OBzl) | 2 | 2-(2-Fu) | 4-(OBzl) | 2 | —Ge(Me)₂— |
| 492 | Zr | Cl | 2-(2-Fu) | 4-TMS | 2 | 2-(2-Fu) | 4-TMS | 2 | —Ge(Me)₂— |
| 493 | Zr | Cl | 2-(2-Fu) | 4-(1-Pyr) | 2 | 2-(2-Fu) | 4-(1-Pyr) | 2 | —Ge(Me)₂— |
| 494 | Zr | Cl | 2-(2-Fu) | 4-(1-Indo) | 2 | 2-(2-Fu) | 4-(1-Indo) | 2 | —Ge(Me)₂— |
| 495 | Zr | Cl | 2-(2-Fu), 4-(2-Fu) | — | 2 | 2-(2-Fu), 4-(2-Fu) | — | 2 | —Ge(Me)₂— |
| 496 | Zr | Me | 2-(2-Fu), 4-(2-Thie) | — | 2 | 2-(2-Fu), 4-(2-Thie) | — | 2 | —Ge(Me)₂— |
| 497 | Zr | Bzl | 2-(2-Fu), 4-(2-BzFu) | — | 2 | 2-(2-Fu), 4-(2-BzFu) | — | 2 | —Ge(Me)₂— |
| 498 | Hf | Cl | 2-(2-Fu), 4-(2-Py) | — | 2 | 2-(2-Fu), 4-(2-Py) | — | 2 | —Ge(Me)₂— |
| 499 | Ti | Cl | 2-(2-Fu), 4-(1-MePyr) | — | 2 | 2-(2-Fu), 4-(1-MePyr) | — | 2 | —Ge(Me)₂— |
| 500 | Hf | Cl | 2-(2-Fu) | 4-Et, 7-Et | 3 | 2-(2-Fu) | 4-Et, 7-Et | 3 | —Ge(Me)₂— |
| 501 | Ti | Cl | 2-(2-Fu) | 4-i-Pr, 7-i-Pr | 3 | 2-(2-Fu) | 4-i-Pr, 7-i-Pr | 3 | —Ge(Me)₂— |
| 502 | Zr | Cl | 2-(2-Fu) | 4-t-Bu, 7-t-Bu | 3 | 2-(2-Fu) | 4-t-Bu, 7-t-Bu | 3 | —Ge(Me)₂— |
| 503 | Zr | Cl | 2-(2-Fu) | 4-Ph, 7-Ph | 3 | 2-(2-Fu) | 4-Ph, 7-Ph | 3 | —Ge(Me)₂— |
| 504 | Zr | Cl | 2-(2-Fu) | 3-Ph, 7-Me | 3 | 2-(2-Fu) | 3-Ph, 7-Me | 3 | —Ge(Me)₂— |
| 505 | Zr | Cl | 2-(2-Fu) | 4-Me, 7-Me | 3 | 2-(2-Fu) | 4-Me, 7-Me | 3 | —Ge(Me)₂— |
| 506 | Zr | Cl | 2-(2-Fu) | 4-Me, 7-Me | 3 | 2-(2-Fu) | 4-Me, 7-Me | 2 | —Ge(Me)₂— |
| 507 | Zr | Me | 2-(2-Fu) | 4-Ph | 2 | 2-(2-Fu) | 4-Ph | 2 | —Ge(Me)₂— |
| 508 | Zr | Bzl | 2-(2-Fu) | 4-Ph | 2 | 2-(2-Fu) | 4-Ph | 2 | —Ge(Me)₂— |
| 509 | Hf | Cl | 2-(2-Fu) | 4-Ph | 2 | 2-(2-Fu) | 4-Ph | 2 | —Ge(Me)₂— |
| 510 | Ti | Cl | 2-(2-Fu) | 4-Ph | 2 | 2-(2-Fu) | 4-Ph | 2 | —Ge(Me)₂— |
| 511 | Hf | Cl | 2-(2-Fu) | 3-Me, 7-Me | 3 | 2-(2-Fu) | 3-Me, 7-Me | 3 | —Ge(Me)₂— |
| 512 | Ti | Cl | 2-(2-Fu) | 3-Me, 7-Me | 3 | 2-(2-Fu) | 3-Me, 7-Me | 3 | —Ge(Me)₂— |
| 513 | Zr | Cl | 2-(3-Fu) | 4-Ph | 2 | 2-(3-Fu) | 4-Ph | 2 | —Ge(Me)₂— |
| 514 | Zr | Cl | 2-(3-Fu) | 4-Ph | 2 | 2-(3-Fu) | 4-Ph | 2 | —Ge(Me)₂— |
| 515 | Zr | Cl | 2-[2-(3-Me-Fu)] | 4-Ph | 2 | 2-[2-(3-Me-Fu)] | 4-Ph | 2 | —Ge(Me)₂— |
| 516 | Zr | Cl | 2-[2-(3-Me-Fu)] | — | 1 | 2-[2-(3-Me-Fu)] | — | 1 | —Ge(Me)₂— |
| 517 | Zr | Cl | 2-(2-Thie) | 4-Ph | 2 | 2-(2-Thie) | 4-Ph | 2 | —Ge(Me)₂— |
| 518 | Zr | Cl | 2-(2-Thie) | — | 1 | 2-(2-Thie) | — | 1 | —Ge(Me)₂— |
| 519 | Zr | Cl | 2-(2-Py) | 4-Ph | 2 | 2-(2-Py) | 4-Ph | 2 | —Ge(Me)₂— |
| 520 | Zr | Cl | 2-(2-(Py) | — | 1 | 2-(2-Py) | — | 1 | —Ge(Me)₂— |
| 521 | Zr | Cl | 2-(2-BzFu) | 4-Ph | 2 | 2-(2-(BzFu) | 4-Ph | 2 | —Ge(Me)₂— |

TABLE 13-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 522 | Zr | Cl | 2-(2-BzFu) | — | 1 | 2-(2-(BzFu) | — | 1 | —Ge(Me)$_2$— |
| 523 | Zr | Cl | 2-[2-(1-Me-Pyr)] | 4-Ph | 2 | 2-[2-(1-Me-Pyr)] | 4-Ph | 2 | —Ge(Me)$_2$— |
| 524 | Zr | Cl | 2-[2-(1-Me-Pyr)] | — | 1 | 2-[2-(1-Me-Pyr)] | — | 1 | —Ge(Me)$_2$— |

TABLE 14

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 525 | Zr | Cl | 2-(2-Fu) | — | 1 | 3-(2-Fu) | — | 1 | —CH$_2$— |
| 526 | Zr | Cl | 2-(2-Fu) | — | 1 | 2-(2-Fu) | — | 1 | —C(Me)$_2$— |
| 527 | Zr | Cl | 2-(2-Fu) | 7-Me | 2 | 2-(2-Fu) | 7-Me | 2 | —C(Me)$_2$— |
| 528 | Zr | Cl | 2-(2-Fu) | 4-Me | 2 | 2-(2-Fu) | 4-Me | 2 | —C(Me)$_2$— |
| 529 | Zr | Cl | 2-(2-Fu) | 3-Me | 2 | 2-(2-Fu) | 3-Me | 2 | —C(Me)$_2$— |
| 530 | Zr | Cl | 2-(2-Fu) | 3-Me, 7-Me | 3 | 2-(2-Fu) | 3-Me, 7-Me | 2 | —C(Me)$_2$— |
| 531 | Zr | Cl | 2-(2-Fu) | 4-Me, 7-Me | 3 | 2-(2-Fu) | 3-Me, 7-Me | 2 | —C(Me)$_2$— |
| 532 | Zr | Cl | 2-(2-Fu) | 4-Cl | 2 | 2-(2-Fu) | 4-Me, 7-Me | 2 | —C(Me)$_2$— |
| 533 | Zr | Cl | 2-(2-Fu) | 4-Et | 2 | 2-(2-Fu) | 4-Cl | 2 | —C(Me)$_2$— |
| 534 | Zr | Cl | 2-(2-Fu) | 4-i-Pr | 2 | 2-(2-Fu) | 4-i-Pr | 2 | —C(Me)$_2$— |
| 535 | Zr | Cl | 2-(2-Fu) | 4-t-Bu | 2 | 2-(2-Fu) | 4-t-Bu | 2 | —C(Me)$_2$— |
| 536 | Zr | Cl | 2-(2-Fu) | 4-Ph | 2 | 2-(2-Fu) | 4-Ph | 2 | —C(Me)$_2$— |
| 537 | Zr | Cl | 2-(2-Fu) | 4-Np | 2 | 2-(2-Fu) | 4-Np | 2 | —C(Me)$_2$— |
| 538 | Zr | Cl | 2-(2-Fu) | 4-OMe | 2 | 2-(2-Fu) | 4-OMe | 2 | —C(Me)$_2$— |
| 539 | Zr | Cl | 2-(2-Fu) | 4-OPh | 2 | 2-(2-Fu) | 4-OPh | 2 | —C(Me)$_2$— |
| 540 | Zr | Cl | 2-(2-Fu) | 4-Bzl | 2 | 2-(2-Fu) | 4-Bzl | 2 | —C(Me)$_2$— |
| 541 | Zr | Cl | 2-(2-Fu) | 4-Tol | 2 | 2-(2-Fu) | 4-Tol | 2 | —C(Me)$_2$— |
| 542 | Zr | Cl | 2-(2-Fu) | 4-(OBzl) | 2 | 2-(2-Fu) | 4-(OBzl) | 2 | —C(Me)$_2$— |
| 543 | Zr | Cl | 2-(2-Fu) | 4-TMS | 2 | 2-(2-Fu) | 4-TMS | 2 | —C(Me)$_2$— |
| 544 | Zr | Cl | 2-(2-Fu) | 4-(1-Pyr) | 2 | 2-(2-Fu) | 4-(1-Pyr) | 2 | —C(Me)$_2$— |
| 545 | Zr | Cl | 2-(2-Fu) | 4-(1-Indo) | 2 | 2-(2-Fu) | 4-(1-Indo) | 2 | —C(Me)$_2$— |
| 546 | Zr | Cl | 2-(2-Fu), 4-(2-Fu) | — | 2 | 2-(2-Fu), 4-(2-Fu) | — | 2 | —C(Me)$_2$— |
| 547 | Zr | Me | 2-(2-Fu), 4-(2-Thie) | — | 2 | 2-(2-Fu), 4-(2-Thie) | — | 2 | —C(Me)$_2$— |
| 548 | Zr | Bzl | 2-(2-Fu), 4-(2-BzFu) | — | 2 | 2-(2-Fu), 4-(2-BzFu) | — | 2 | —C(Me)$_2$— |
| 549 | Hf | Cl | 2-(2-Fu), 4-(2-Py) | — | 2 | 2-(2-Fu), 4-(2-Py) | — | 2 | —C(Me)$_2$— |
| 550 | Ti | Cl | 2-(2-Fu), 4-(1-MePyr) | — | 2 | 2-(2-Fu), 4-(1-MePyr) | — | 2 | —C(Me)$_2$— |
| 551 | Hf | Cl | 2-(2-Fu) | 4-Et, 7-Et | 3 | 2-(2-Fu) | 4-Et, 7-Et | 3 | —C(Me)$_2$— |
| 552 | Ti | Cl | 2-(2-Fu) | 4-i-Pr, 7-i-Pr | 3 | 2-(2-Fu) | 4-i-Pr, 7-i-Pr | 3 | —C(Me)$_2$— |
| 553 | Zr | Cl | 2-(2-Fu) | 4-t-Bu, 7-t-Bu | 3 | 2-(2-Fu) | 4-t-Bu, 7-t-Bu | 3 | —C(Me)$_2$— |
| 554 | Zr | Cl | 2-(2-Fu) | 4-Ph, 7-Ph | 3 | 2-(2-Fu) | 4-Ph, 7-Ph | 3 | —C(Me)$_2$— |
| 555 | Zr | Cl | 2-(2-Fu) | 3-Ph, 7-Me | 3 | 2-(2-Fu) | 3-Ph, 7-Me | 3 | —C(Me)$_2$— |
| 556 | Zr | Cl | 2-(2-Fu) | 4-Me, 7-Me | 3 | 2-(2-Fu) | 4-Me, 7-Me | 3 | —C(Me)$_2$— |
| 557 | Zr | Cl | 2-(2-Fu) | 4-Me, 7-Me | 3 | 2-(2-Fu) | 4-Me, 7-Me | 2 | —C(Me)$_2$— |
| 558 | Zr | Me | 2-(2-Fu) | 4-Ph | 2 | 2-(2-Fu) | 4-Ph | 2 | —C(Me)$_2$— |
| 559 | Zr | Bzl | 2-(2-Fu) | 4-Ph | 2 | 2-(2-Fu) | 4-Ph | 2 | —C(Me)$_2$— |
| 560 | Hf | Cl | 2-(2-Fu) | 4-Ph | 2 | 2-(2-Fu) | 4-Ph | 2 | —C(Me)$_2$— |
| 561 | Ti | Cl | 2-(2-Fu) | 4-Ph | 2 | 2-(2-Fu) | 4-Ph | 2 | —C(Me)$_2$— |
| 552 | Hf | Cl | 2-(2-Fu) | 3-Me, 7-Me | 3 | 2-(2-Fu) | 3-Me, 7-Me | 3 | —C(Me)$_2$— |
| 563 | Ti | Cl | 2-(2-Fu) | 3-Me, 7-Me | 3 | 2-(2-Fu) | 3-Me, 7-Me | 3 | —C(Me)$_2$— |
| 564 | Zr | Cl | 2-(3-Fu) | 4-Ph | 2 | 2-(3-Fu) | 4-Ph | 2 | —C(Me)$_2$— |
| 565 | Zr | Cl | 2-(3-Fu) | 4-Ph | 2 | 2-(3-Fu) | 4-Ph | 2 | —C(Me)$_2$— |
| 566 | Zr | Cl | 2-[2-(3-Me-Fu)] | 4-Ph | 2 | 2-[2-(3-Me-Fu)] | 4-Ph | 2 | —C(Me)$_2$— |
| 567 | Zr | Cl | 2-[2-(3-Me-Fu)] | — | 1 | 2-[2-(3-Me-Fu)] | — | 1 | —C(Me)$_2$— |
| 568 | Zr | Cl | 2-(2-Thie) | 4-Ph | 2 | 2-(2-Thie) | 4-Ph | 2 | —C(Me)$_2$— |
| 569 | Zr | Cl | 2-(2-Thie) | — | 1 | 2-(2-Thie) | — | 1 | —C(Me)$_2$— |
| 570 | Zr | Cl | 2-(2-Py) | 4-Ph | 2 | 2-(2-Py) | 4-Ph | 2 | —C(Me)$_2$— |
| 571 | Zr | Cl | 2-(2-(Py) | — | 1 | 2-(2-Py) | — | 1 | —C(Me)$_2$— |
| 572 | Zr | Cl | 2-(2-BzFu) | 4-Ph | 2 | 2-(2-BzFu) | 4-Ph | 2 | —C(Me)$_2$— |
| 573 | Zr | Cl | 2-(2-BzFu) | — | 1 | 2-(2-(BzFu) | — | 1 | —C(Me)$_2$— |
| 574 | Zr | Cl | 2-[2-(1-Me-Pyr)] | 4-Ph | 2 | 2-[2-(1-Me-Pyr)] | 4-Ph | 2 | —C(Me)$_2$— |
| 575 | Zr | Cl | 2-[2-(1-Me-Pyr)] | — | 1 | 2-[2-(1-Me-Pyr)] | — | 1 | —C(Me)$_2$— |

TABLE 15

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 576 | Zr | Cl | 2-(2-Fu) | — | 1 | 3-(2-Fu) | — | 1 | —CH$_2$CH$_2$— |
| 577 | Zr | Cl | 2-(2-Fu) | — | 1 | 2-(2-Fu) | — | 1 | —C$_2$(Me)$_4$— |
| 578 | Zr | Cl | 2-(2-Fu) | 7-Me | 2 | 2-(2-Fu) | 7-Me | 2 | —C$_2$(Me)$_4$— |
| 579 | Zr | Cl | 2-(2-Fu) | 4-Me | 2 | 2-(2-Fu) | 4-Me | 2 | —C$_2$(Me)$_4$— |
| 580 | Zr | Cl | 2-(2-Fu) | 3-Me | 2 | 2-(2-Fu) | 3-Me | 2 | —C$_2$(Me)$_4$— |

TABLE 15-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 581 | Zr | Cl | 2-(2-Fu) | 3-Me, 7-Me | 3 | 2-(2-Fu) | 3-Me, 7-Me | 2 | —C$_2$(Me)$_4$— |
| 582 | Zr | Cl | 2-(2-Fu) | 4-Me, 7-Me | 3 | 2-(2-Fu) | 3-Me, 7-Me | 2 | —C$_2$(Me)$_4$— |
| 583 | Zr | Cl | 2-(2-Fu) | 4-Cl | 2 | 2-(2-Fu) | 4-Me, 7-Me | 2 | —C$_2$(Me)$_4$— |
| 584 | Zr | Cl | 2-(2-Fu) | 4-Et | 2 | 2-(2-Fu) | 4-Cl | 2 | —C$_2$(Me)$_4$— |
| 585 | Zr | Cl | 2-(2-Fu) | 4-i-Pr | 2 | 2-(2-Fu) | 4-i-Pr | 2 | —C$_2$(Me)$_4$— |
| 586 | Zr | Cl | 2-(2-Fu) | 4-t-Bu | 2 | 2-(2-Fu) | 4-t-Bu | 2 | —C$_2$(Me)$_4$— |
| 587 | Zr | Cl | 2-(2-Fu) | 4-Ph | 2 | 2-(2-Fu) | 4-Ph | 2 | —C$_2$(Me)$_4$— |
| 588 | Zr | Cl | 2-(2-Fu) | 4-Np | 2 | 2-(2-Fu) | 4-Np | 2 | —C$_2$(Me)$_4$— |
| 589 | Zr | Cl | 2-(2-Fu) | 4-OMe | 2 | 2-(2-Fu) | 4-OMe | 2 | —C$_2$(Me)$_4$— |
| 590 | Zr | Cl | 2-(2-Fu) | 4-OPh | 2 | 2-(2-Fu) | 4-OPh | 2 | —C$_2$(Me)$_4$— |
| 591 | Zr | Cl | 2-(2-Fu) | 4-Bzl | 2 | 2-(2-Fu) | 4-Bzl | 2 | —C$_2$(Me)$_4$— |
| 592 | Zr | Cl | 2-(2-Fu) | 4-Tol | 2 | 2-(2-Fu) | 4-Tol | 2 | —C$_2$(Me)$_4$— |
| 593 | Zr | Cl | 2-(2-Fu) | 4-(OBzl) | 2 | 2-(2-Fu) | 4-(OBzl) | 2 | —C$_2$(Me)$_4$— |
| 594 | Zr | Cl | 2-(2-Fu) | 4-TMS | 2 | 2-(2-Fu) | 4-TMS | 2 | —C$_2$(Me)$_4$— |
| 595 | Zr | Cl | 2-(2-Fu) | 4-(1-Pyr) | 2 | 2-(2-Fu) | 4-(1-Pyr) | 2 | —C$_2$(Me)$_4$— |
| 596 | Zr | Cl | 2-(2-Fu) | 4-(1-Indo) | 2 | 2-(2-Fu) | 4-(1-Indo) | 2 | —C$_2$(Me)$_4$— |
| 597 | Zr | Cl | 2-(2-Fu), 4-(2-Fu) | — | 2 | 2-(2-Fu), 4-(2-Fu) | — | 2 | —C$_2$(Me)$_4$— |
| 598 | Zr | Me | 2-(2-Fu), 4-(2-Thie) | — | 2 | 2-(2-Fu), 4-(2-Thie) | — | 2 | —C$_2$(Me)$_4$— |
| 599 | Zr | Bzl | 2-(2-Fu), 4-(2-BzFu) | — | 2 | 2-(2-Fu), 4-(2-BzFu) | — | 2 | —C$_2$(Me)$_4$— |
| 600 | Hf | Cl | 2-(2-Fu), 4-(2-Py) | — | 2 | 2-(2-Fu), 4-(2-Py) | — | 2 | —C$_2$(Me)$_4$— |
| 601 | Ti | Cl | 2-(2-Fu), 4-(1-MePyr) | — | 2 | 2-(2-Fu), 4-(1-MePyr) | — | 2 | —C$_2$(Me)$_4$— |
| 602 | Hf | Cl | 2-(2-Fu) | 4-Et, 7-Et | 3 | 2-(2-Fu) | 4-Et, 7-Et | 3 | —C$_2$(Me)$_4$— |
| 603 | Ti | Cl | 2-(2-Fu) | 4-i-Pr, 7-i-Pr | 3 | 2-(2-Fu) | 4-i-Pr, 7-i-Pr | 3 | —C$_2$(Me)$_4$— |
| 604 | Zr | Cl | 2-(2-Fu) | 4-t-Bu, 7-t-Bu | 3 | 2-(2-Fu) | 4-t-Bu, 7-t-Bu | 3 | —C$_2$(Me)$_4$— |
| 605 | Zr | Cl | 2-(2-Fu) | 4-Ph, 7-Ph | 3 | 2-(2-Fu) | 4-Ph, 7-Ph | 3 | —C$_2$(Me)$_4$— |
| 606 | Zr | Cl | 2-(2-Fu) | 3-Ph, 7-Me | 3 | 2-(2-Fu) | 3-Ph, 7-Me | 3 | —C$_2$(Me)$_4$— |
| 607 | Zr | Cl | 2-(2-Fu) | 4-Me, 7-Me | 3 | 2-(2-Fu) | 4-Me, 7-Me | 3 | —C$_2$(Me)$_4$— |
| 608 | Zr | Cl | 2-(2-Fu) | 4-Me, 7-Me | 3 | 2-(2-Fu) | 4-Me, 7-Me | 2 | —C$_2$(Me)$_4$— |
| 609 | Zr | Me | 2-(2-Fu) | 4-Ph | 2 | 2-(2-Fu) | 4-Ph | 2 | —C$_2$(Me)$_4$— |
| 610 | Zr | Bzl | 2-(2-Fu) | 4-Ph | 2 | 2-(2-Fu) | 4-Ph | 2 | —C$_2$(Me)$_4$— |
| 611 | Hf | Cl | 2-(2-Fu) | 4-Ph | 2 | 2-(2-Fu) | 4-Ph | 2 | —C$_2$(Me)$_4$— |
| 612 | Ti | Cl | 2-(2-Fu) | 4-Ph | 2 | 2-(2-Fu) | 4-Ph | 2 | —C$_2$(Me)$_4$— |
| 613 | Hf | Cl | 2-(2-Fu) | 3-Me, 7-Me | 3 | 2-(2-Fu) | 3-Me, 7-Me | 3 | —C$_2$(Me)$_4$— |
| 614 | Ti | Cl | 2-(2-Fu) | 3-Me, 7-Me | 3 | 2-(2-Fu) | 3-Me, 7-Me | 3 | —C$_2$(Me)$_4$— |
| 615 | Zr | Cl | 2-(3-Fu) | 4-Ph | 2 | 2-(3-Fu) | 4-Ph | 2 | —C$_2$(Me)$_4$— |
| 616 | Zr | Cl | 2-(3-Fu) | 4-Ph | 2 | 2-(3-Fu) | 4-Ph | 2 | —C$_2$(Me)$_4$— |
| 617 | Zr | Cl | 2-[2-(3-Me-Fu)] | 4-Ph | 2 | 2-[2-(3-Me-Fu)] | 4-Ph | 2 | —C$_2$(Me)$_4$— |
| 618 | Zr | Cl | 2-[2-(3-Me-Fu)] | — | 1 | 2-[2-(3-Me-Fu)] | — | 1 | —C$_2$(Me)$_4$— |
| 619 | Zr | Cl | 2-(2-Thie) | 4-Ph | 2 | 2-(2-Thie) | 4-Ph | 2 | —C$_2$(Me)$_4$— |
| 620 | Zr | Cl | 2-(2-Thie) | — | 1 | 2-(2-Thie) | — | 1 | —C$_2$(Me)$_4$— |
| 621 | Zr | Cl | 2-(2-Py) | 4-Ph | 2 | 2-(2-Py) | 4-Ph | 2 | —C$_2$(Me)$_4$— |
| 622 | Zr | Cl | 2-(2-(Py) | — | 1 | 2-(2-Py) | — | 1 | —C$_2$(Me)$_4$— |
| 623 | Zr | Cl | 2-(2-BzFu) | 4-Ph | 2 | 2-(2-(BzFu) | 4-Ph | 2 | —C$_2$(Me)$_4$— |
| 624 | Zr | Cl | 2-(2-BzFu) | — | 1 | 2-(2-(BzFu) | — | 1 | —C$_2$(Me)$_4$— |
| 625 | Zr | Cl | 2-[2-(N-Me-Pyr)] | 4-Ph | 2 | 2-[2-(1-Me-Pyr)] | 4-Ph | 2 | —C$_2$(Me)$_4$— |
| 626 | Zr | Cl | 2-[2-(N-Me-Pyr)] | — | 1 | 2-[2-(1-Me-Pyr)] | — | 1 | —C$_2$(Me)$_4$— |

TABLE 16

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 627 | Zr | Cl | 2-(2-Fu) | — | 1 | 3-(2-Fu) | — | 1 | —SiH$_2$— |
| 628 | Zr | Cl | 2-(2-Fu) | — | 1 | 2-(2-Fu) | — | 1 | —Si(Me)$_2$— |
| 629 | Zr | Cl | 2-(2-Fu) | 7-Me | 2 | 2-(2-Fu) | 7-Me | 2 | —Si(Me)$_2$— |
| 630 | Zr | Cl | 2-(2-Fu) | 4-Me | 2 | 2-(2-Fu) | 4-Me | 2 | —Si(Me)$_2$— |
| 631 | Zr | Cl | 2-(2-Fu) | 3-Me | 2 | 2-(2-Fu) | 3-Me | 2 | —Si(Me)$_2$— |
| 632 | Zr | Cl | 2-(2-Fu) | 3-Me, 7-Me | 3 | 2-(2-Fu) | 3-Me, 7-Me | 3 | —Si(Me)$_2$— |
| 633 | Zr | Cl | 2-(2-Fu) | 4-Me, 7-Me | 3 | 2-(2-Fu) | 4-Me, 7-Me | 3 | —Si(Me)$_2$— |
| 634 | Zr | Cl | 2-(2-Fu) | 4-Cl | 2 | 2-(2-Fu) | 4-Cl | 2 | —Si(Me)$_2$— |
| 635 | Zr | Cl | 2-(2-Fu) | 4-Et | 2 | 2-(2-Fu) | 4-Et | 2 | —Si(Me)$_2$— |
| 636 | Zr | Cl | 2-(2-Fu) | 4-I-Pr | 2 | 2-(2-Fu) | 4-I-Pr | 2 | —Si(Me)$_2$— |
| 637 | Zr | Cl | 2-(2-Fu) | 4-t-Bu | 2 | 2-(2-Fu) | 4-t-Bu | 2 | —Si(Me)$_2$— |
| 638 | Zr | Cl | 2-(2-Fu) | 4-Ph | 2 | 2-(2-Fu) | 4-Ph | 2 | —Si(Me)$_2$— |
| 639 | Zr | Cl | 2-(2-Fu) | 4-Np | 2 | 2-(2-Fu) | 4-Np | 2 | —Si(Me)$_2$— |
| 640 | Zr | Cl | 2-(2-Fu) | 4-OMe | 2 | 2-(2-Fu) | 4-OMe | 2 | —Si(Me)$_2$— |
| 641 | Zr | Cl | 2-(2-Fu) | 4-OPh | 2 | 2-(2-Fu) | 4-OPh | 2 | —Si(Me)$_2$— |
| 642 | Zr | Cl | 2-(2-Fu) | 4-Bzl | 2 | 2-(2-Fu) | 4-Bzl | 2 | —Si(Me)$_2$— |
| 643 | Zr | Cl | 2-(2-Fu) | 4-Tol | 2 | 2-(2-Fu) | 4-Tol | 2 | —Si(Me)$_2$— |
| 644 | Zr | Cl | 2-(2-Fu) | 4-(OBzl) | 2 | 2-(2-Fu) | 4-(OBzl) | 2 | —Si(Me)$_2$— |
| 645 | Zr | Cl | 2-(2-Fu) | 4-TMS | 2 | 2-(2-Fu) | 4-TMS | 2 | —Si(Me)$_2$— |
| 646 | Zr | Cl | 2-(2-Fu) | 4-(1-Pyr) | 2 | 2-(2-Fu) | 4-(1-Pyr) | 2 | —Si(Me)$_2$— |
| 647 | Zr | Cl | 2-(2-Fu) | 4-(1-Indo) | 2 | 2-(2-Fu) | 4-(1-Indo) | 2 | —Si(Me)$_2$— |

TABLE 16-continued

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 648 | Zr | Cl | 2-(2-Fu), 4-(2-Fu) | — | 2 | 2-(2-Fu), 4-(2-Fu) | — | 2 | —Si(Me)₂— |
| 649 | Zr | Me | 2-(2-Fu), 4-(2-Thie) | — | 2 | 2-(2-Fu), 4-(2-Thie) | — | 2 | —Si(Me)₂— |
| 650 | Zr | Bzl | 2-(2-Fu), 4-(2-BzFu) | — | 2 | 2-(2-Fu), 4-(2-BzFu) | — | 2 | —Si(Me)₂— |
| 651 | Hf | Cl | 2-(2-Fu), 4-(2-Py) | — | 2 | 2-(2-Fu), 4-(2-Py) | — | 2 | —Si(Me)₂— |
| 652 | Ti | Cl | 2-(2-Fu), 4-(1-MePyr) | — | 2 | 2-(2-Fu), 4-(1-MePyr) | — | 2 | —Si(Me)₂— |
| 653 | Hf | Cl | 2-(2-Fu) | 4-Et, 7-Et | 3 | 2-(2-Fu) | 4-Et, 7-Et | 3 | —Si(Me)₂— |
| 654 | Ti | Cl | 2-(2-Fu) | 4-i-Pr, 7-i-Pr | 3 | 2-(2-Fu) | 4-I-Pr, 7-I-Pr | 3 | —Si(Me)₂— |
| 655 | Zr | Cl | 2-(2-Fu) | 4-t-Bu, 7-t-Bu | 3 | 2-(2-Fu) | 4-t-Bu, 7-t-Bu | 3 | —Si(Me)₂— |
| 656 | Zr | Cl | 2-(2-Fu) | 4-Ph, 7-Ph | 3 | 2-(2-Fu) | 4-Ph, 7-Ph | 3 | —Si(Me)₂— |
| 657 | Zr | Cl | 2-(2-Fu) | 3-Ph, 7-Me | 3 | 2-(2-Fu) | 3-Ph, 7-Me | 3 | —Si(Me)₂— |
| 658 | Zr | Cl | 2-(2-Fu) | 4-Me, 7-Me | 3 | 2-(2-Fu) | 4-Me, 7-Me | 3 | —Si(Me)₂— |
| 659 | Zr | Cl | 2-(2-Fu) | 4-Me, 7-Me | 3 | 2-(2-Fu) | 4-Me, 7-Me | 2 | —Si(Me)₂— |
| 660 | Zr | Me | 2-(2-Fu) | 4-Ph | 2 | 2-(2-Fu) | 4-Ph | 2 | —Si(Me)₂— |
| 661 | Zr | Bzl | 2-(2-Fu) | 4-Ph | 2 | 2-(2-Fu) | 4-Ph | 2 | —Si(Me)₂— |
| 662 | Hf | Cl | 2-(2-Fu) | 4-Ph | 2 | 2-(2-Fu) | 4-Ph | 2 | —Si(Me)₂— |
| 663 | Ti | Cl | 2-(2-Fu) | 4-Ph | 2 | 2-(2-Fu) | 4-Ph | 2 | —Si(Me)₂— |
| 664 | Hf | Cl | 2-(2-Fu) | 3-Me, 7-Me | 3 | 2-(2-Fu) | 3-Me, 7-Me | 3 | —Si(Me)₂— |
| 665 | Ti | Cl | 2-(2-Fu) | 3-Me, 7-Me | 3 | 2-(2-Fu) | 3-Me, 7-Me | 3 | —Si(Me)₂— |
| 666 | Zr | Cl | 2-(3-Fu) | 4-Ph | 2 | 2-(3-Fu) | 4-Ph | 2 | —Si(Me)₂— |
| 667 | Zr | Cl | 2-(3-Fu) | 4-Ph | 2 | 2-(3-Fu) | 4-Ph | 2 | —Si(Me)₂— |
| 668 | Zr | Cl | 2-[2-(3-Me-Fu)] | 4-Ph | 2 | 2-[2-(3-Me—Fu)] | 4-Ph | 2 | —Si(Me)₂— |
| 669 | Zr | Cl | 2-[2-(3-Me-Fu)] | — | 1 | 2-[2-(3-Me—Fu)] | — | 1 | —Si(Me)₂— |
| 670 | Zr | Cl | 2-(2-Thie) | 4-Ph | 2 | 2-(2-Thie) | 4-Ph | 2 | —Si(Me)₂— |
| 671 | Zr | Cl | 2-(2-Thie) | — | 1 | 2-(2-Thie) | — | 1 | —Si(Me)₂— |
| 672 | Zr | Cl | 2-(2-Py) | 4-Ph | 2 | 2-(2-Py) | 4-Ph | 2 | —Si(Me)₂— |
| 673 | Zr | Cl | 2-(2-(Py) | — | 1 | 2-(2-Py) | — | 1 | —Si(Me)₂— |
| 674 | Zr | Cl | 2-(2-BzFu) | 4-Ph | 2 | 2-(2-(BzFu) | 4-Ph | 2 | —Si(Me)₂— |
| 675 | Zr | Cl | 2-(2-BzFu) | — | 1 | 2-(2-(BzFu) | — | 1 | —Si(Me)₂— |
| 676 | Zr | Cl | 2-[2-(N-Me-Pyr)] | 4-Ph | 2 | 2-[2-(N-Me—Pyr)] | 4-Ph | 2 | —Si(Me)₂— |
| 677 | Zr | Cl | 2-[2-(N-Me-Pyr)] | — | 1 | 2-[2-(N-Me—Pyr)] | — | 1 | —Si(Me)₂— |

TABLE 17

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 678 | Zr | Cl | 2-(2-Fu) | — | 1 | 3-(2-Fu) | — | 1 | —GeH₂— |
| 679 | Zr | Cl | 2-(2-Fu) | — | 1 | 2-(2-Fu) | — | 1 | —Ge(Me)₂— |
| 680 | Zr | Cl | 2-(2-Fu) | 7-Me | 2 | 2-(2-Fu) | 7-Me | 2 | —Ge(Me)₂— |
| 681 | Zr | Cl | 2-(2-Fu) | 4-Me | 2 | 2-(2-Fu) | 4-Me | 2 | —Ge(Me)₂— |
| 682 | Zr | Cl | 2-(2-Fu) | 3-Me | 2 | 2-(2-Fu) | 3-Me | 2 | —Ge(Me)₂— |
| 683 | Zr | Cl | 2-(2-Fu) | 3-Me, 7-Me | 3 | 2-(2-Fu) | 3-Me, 7-Me | 3 | —Ge(Me)₂— |
| 684 | Zr | Cl | 2-(2-Fu) | 4-Me, 7-Me | 3 | 2-(2-Fu) | 4-Me, 7-Me | 3 | —Ge(Me)₂— |
| 685 | Zr | Cl | 2-(2-Fu) | 4-Cl | 2 | 2-(2-Fu) | 4-Cl | 2 | —Ge(Me)₂— |
| 686 | Zr | Cl | 2-(2-Fu) | 4-Et | 2 | 2-(2-Fu) | 4-Et | 2 | —Ge(Me)₂— |
| 687 | Zr | Cl | 2-(2-Fu) | 4-I-Pr | 2 | 2-(2-Fu) | 4-I-Pr | 2 | —Ge(Me)₂— |
| 688 | Zr | Cl | 2-(2-Fu) | 4-t-Bu | 2 | 2-(2-Fu) | 4-t-Bu | 2 | —Ge(Me)₂— |
| 689 | Zr | Cl | 2-(2-Fu) | 4-Ph | 2 | 2-(2-Fu) | 4-Ph | 2 | —Ge(Me)₂— |
| 690 | Zr | Cl | 2-(2-Fu) | 4-Np | 2 | 2-(2-Fu) | 4-Np | 2 | —Ge(Me)₂— |
| 691 | Zr | Cl | 2-(2-Fu) | 4-OMe | 2 | 2-(2-Fu) | 4-OMe | 2 | —Ge(Me)₂— |
| 692 | Zr | Cl | 2-(2-Fu) | 4-OPh | 2 | 2-(2-Fu) | 4-OPh | 2 | —Ge(Me)₂— |
| 693 | Zr | Cl | 2-(2-Fu) | 4-Bzl | 2 | 2-(2-Fu) | 4-Bzl | 2 | —Ge(Me)₂— |
| 694 | Zr | Cl | 2-(2-Fu) | 4-Tol | 2 | 2-(2-Fu) | 4-Tol | 2 | —Ge(Me)₂— |
| 695 | Zr | Cl | 2-(2-Fu) | 4-(OBzl) | 2 | 2-(2-Fu) | 4-(OBzl) | 2 | —Ge(Me)₂— |
| 696 | Zr | Cl | 2-(2-Fu) | 4-TMS | 2 | 2-(2-Fu) | 4-TMS | 2 | —Ge(Me)₂— |
| 697 | Zr | Cl | 2-(2-Fu) | 4-(1-Pyr) | 2 | 2-(2-Fu) | 4-(1-Pyr) | 2 | —Ge(Me)₂— |
| 698 | Zr | Cl | 2-(2-Fu) | 4-(1-Indo) | 2 | 2-(2-Fu) | 4-(1-Indo) | 2 | —Ge(Me)₂— |
| 699 | Zr | Cl | 2-(2-Fu), 4-(2-Fu) | — | 2 | 2-(2-Fu), 4-(2-Fu) | — | 2 | —Ge(Me)₂— |
| 700 | Zr | Me | 2-(2-Fu), 4-(2-Thie) | — | 2 | 2-(2-Fu), 4-(2-Thie) | — | 2 | —Ge(Me)₂— |
| 701 | Zr | Bzl | 2-(2-Fu), 4-(2-BzFu) | — | 2 | 2-(2-Fu), 4-(2-BzFu) | — | 2 | —Ge(Me)₂— |
| 702 | Hf | Cl | 2-(2-Fu), 4-(2-Py) | — | 2 | 2-(2-Fu), 4-(2-Py) | — | 2 | —Ge(Me)₂— |
| 703 | Ti | Cl | 2-(2-Fu), 4-(1-MePyr) | — | 2 | 2-(2-Fu), 4-(1-MePyr) | — | 2 | —Ge(Me)₂— |
| 704 | Hf | Cl | 2-(2-Fu) | 4-Et, 7-Et | 3 | 2-(2-Fu) | 4-Et, 7-Et | 3 | —Ge(Me)₂— |
| 705 | Ti | Cl | 2-(2-Fu) | 4-i-Pr, 7-i-Pr | 3 | 2-(2-Fu) | 4-I-Pr, 7-I-Pr | 3 | —Ge(Me)₂— |
| 706 | Zr | Cl | 2-(2-Fu) | 4-t-Bu, 7-t-Bu | 3 | 2-(2-Fu) | 4-t-Bu, 7-t-Bu | 3 | —Ge(Me)₂— |
| 707 | Zr | Cl | 2-(2-Fu) | 4-Ph, 7-Ph | 3 | 2-(2-Fu) | 4-Ph, 7-Ph | 3 | —Ge(Me)₂— |
| 708 | Zr | Cl | 2-(2-Fu) | 3-Ph, 7-Me | 3 | 2-(2-Fu) | 3-Ph, 7-Me | 3 | —Ge(Me)₂— |
| 709 | Zr | Cl | 2-(2-Fu) | 4-Me, 7-Me | 3 | 2-(2-Fu) | 4-Me, 7-Me | 3 | —Ge(Me)₂— |
| 710 | Zr | Cl | 2-(2-Fu) | 4-Me, 7-Me | 3 | 2-(2-Fu) | 4-Me, 7-Me | 2 | —Ge(Me)₂— |
| 711 | Zr | Me | 2-(2-Fu) | 4-Ph | 2 | 2-(2-Fu) | 4-Ph | 2 | —Ge(Me)₂— |

TABLE 17-continued

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 712 | Zr | Bzl | 2-(2-Fu) | 4-Ph | 2 | 2-(2-Fu) | 4-Ph | 2 | —Ge(Me)₂— |
| 713 | Hf | Cl | 2-(2-Fu) | 4-Ph | 2 | 2-(2-Fu) | 4-Ph | 2 | —Ge(Me)₂— |
| 714 | Ti | Cl | 2-(2-Fu) | 4-Ph | 2 | 2-(2-Fu) | 4-Ph | 2 | —Ge(Me)₂— |
| 715 | Hf | Cl | 2-(2-Fu) | 3-Me, 7-Me | 3 | 2-(2-Fu) | 3-Me, 7-Me | 3 | —Ge(Me)₂— |
| 716 | Ti | Cl | 2-(2-Fu) | 3-Me, 7-Me | 3 | 2-(2-Fu) | 3-Me, 7-Me | 3 | —Ge(Me)₂— |
| 717 | Zr | Cl | 2-(3-Fu) | 4-Ph | 2 | 2-(3-Fu) | 4-Ph | 2 | —Ge(Me)₂— |
| 718 | Zr | Cl | 2-(3-Fu) | 4-Ph | 2 | 2-(3-Fu) | 4-Ph | 2 | —Ge(Me)₂— |
| 719 | Zr | Cl | 2-[2-(3-Me-Fu)] | 4-Ph | 2 | 2-[2-(3-Me—Fu)] | 4-Ph | 2 | —Ge(Me)₂— |
| 720 | Zr | Cl | 2-[2-(3-Me-Fu)] | — | 1 | 2-[2-(3-Me—Fu)] | — | 1 | —Ge(Me)₂— |
| 721 | Zr | Cl | 2-(2-Thie) | 4-Ph | 2 | 2-(2-Thie) | 4-Ph | 2 | —Ge(Me)₂— |
| 722 | Zr | Cl | 2-(2-Thie) | — | 1 | 2-(2-Thie) | — | 1 | —Ge(Me)₂— |
| 723 | Zr | Cl | 2-(2-Py) | 4-Ph | 2 | 2-(2-Py) | 4-Ph | 2 | —Ge(Me)₂— |
| 724 | Zr | Cl | 2-(2-(Py) | — | 1 | 2-(2-Py) | — | 1 | —Ge(Me)₂— |
| 725 | Zr | Cl | 2-(2-BzFu) | 4-Ph | 2 | 2-(2-BzFu) | 4-Ph | 2 | —Ge(Me)₂— |
| 726 | Zr | Cl | 2-(2-BzFu) | — | 1 | 2-(2-(BzFu) | — | 1 | —Ge(Me)₂— |
| 727 | Zr | Cl | 2-[2-(N-Me-Pyr)] | 4-Ph | 2 | 2-[2-(N-Me—Pyr)] | 4-Ph | 2 | —Ge(Me)₂— |
| 728 | Zr | Cl | 2-[2-(N-Me-Pyr)] | — | 1 | 2-[2-(N-Me—Pyr)] | — | 1 | —Ge(Me)₂— |

TABLE 18

| No. | M | X | CA¹: Cyclopentadiene Ra | R¹ | p + m | CA²: Cyclopentadiene Ra | R¹ | q + n | Y |
|---|---|---|---|---|---|---|---|---|---|
| 729 | Zr | Cl | 2-(2-Fu) | — | 1 | 3-(2-Fu) | — | 1 | —SiH₂— |
| 730 | Zr | Cl | 2-(2-Fu) | — | 1 | 2-(2-Fu) | — | 1 | —Si(Me)₂— |
| 731 | Zr | Cl | 2-(2-Fu) | 9-Me | 2 | 2-(2-Fu) | 9-Me | 2 | —Si(Me)₂— |
| 732 | Zr | Cl | 2-(2-Fu) | 5-Me | 2 | 2-(2-Fu) | 5-Me | 2 | —Si(Me)₂— |
| 733 | Zr | Cl | 2-(2-Fu) | 3-Me | 2 | 2-(2-Fu) | 3-Me | 2 | —Si(Me)₂— |
| 734 | Zr | Cl | 2-(2-Fu) | 3-Me, 9-Me | 3 | 2-(2-Fu) | 3-Me, 9-Me | 3 | —Si(Me)₂— |
| 735 | Zr | Cl | 2-(2-Fu) | 5-Me, 9-Me | 3 | 2-(2-Fu) | 5-Me, 9-Me | 3 | —Si(Me)₂— |
| 736 | Zr | Cl | 2-(2-Fu) | 5-Cl | 2 | 2-(2-Fu) | 5-Cl | 2 | —Si(Me)₂— |
| 737 | Zr | Cl | 2-(2-Fu) | 5-Et | 2 | 2-(2-Fu) | 5-Et | 2 | —Si(Me)₂— |
| 738 | Zr | Cl | 2-(2-Fu) | 5-i-Pr | 2 | 2-(2-Fu) | 5-i-Pr | 2 | —Si(Me)₂— |
| 739 | Zr | Cl | 2-(2-Fu) | 5-t-Bu | 2 | 2-(2-Fu) | 5-t-Bu | 2 | —Si(Me)₂— |
| 740 | Zr | Cl | 2-(2-Fu) | 5-Ph | 2 | 2-(2-Fu) | 5-Ph | 2 | —Si(Me)₂— |
| 741 | Zr | Cl | 2-(2-Fu) | 5-Np | 2 | 2-(2-Fu) | 5-Np | 2 | —Si(Me)₂— |
| 742 | Zr | Cl | 2-(2-Fu) | 5-OMe | 2 | 2-(2-Fu) | 5-OMe | 2 | —Si(Me)₂— |
| 743 | Zr | Cl | 2-(2-Fu) | 5-OPh | 2 | 2-(2-Fu) | 5-OPh | 2 | —Si(Me)₂— |
| 744 | Zr | Cl | 2-(2-Fu) | 5-Bzl | 2 | 2-(2-Fu) | 5-Bzl | 2 | —Si(Me)₂— |
| 745 | Zr | Cl | 2-(2-Fu) | 5-Tol | 2 | 2-(2-Fu) | 5-Tol | 2 | —Si(Me)₂— |
| 746 | Zr | Cl | 2-(2-Fu) | 5-(OBzl) | 2 | 2-(2-Fu) | 5-(OBzl) | 2 | —Si(Me)₂— |
| 747 | Zr | Cl | 2-(2-Fu) | 5-TMS | 2 | 2-(2-Fu) | 5-TMS | 2 | —Si(Me)₂— |
| 748 | Zr | Cl | 2-(2-Fu) | 5-(1-Pyr) | 2 | 2-(2-Fu) | 5-(1-Pyr) | 2 | —Si(Me)₂— |
| 749 | Zr | Cl | 2-(2-Fu) | 5-(1-Indo) | 2 | 2-(2-Fu) | 5-(1-Indo) | 2 | —Si(Me)₂— |
| 750 | Zr | Cl | 2-(2-Fu), 5-(2-Fu) | — | 2 | 2-(2-Fu), 5-(2-Fu) | — | 2 | —Si(Me)₂— |
| 751 | Zr | Me | 2-(2-Fu), 5-(2-Thie) | — | 2 | 2-(2-Fu), 5-(2-Thie) | — | 2 | —Si(Me)₂— |
| 752 | Zr | Bzl | 2-(2-Fu), 5-(2-BzFu) | — | 2 | 2-(2-Fu), 5-(2-BzFu) | — | 2 | —Si(Me)₂— |
| 753 | Hf | Cl | 2-(2-Fu), 5-(2-Py) | — | 2 | 2-(2-Fu), 5-(2-Py) | — | 2 | —Si(Me)₂— |
| 754 | Ti | Cl | 2-(2-Fu), 5-[2-(1-MePyr)] | — | 2 | 2-(2-Fu), 5-(1-MePyr) | — | 2 | —Si(Me)₂— |
| 755 | Hf | Cl | 2-(2-Fu) | 5-Et, 9-Et | 3 | 2-(2-Fu) | 4-Et, 7-Et | 3 | —Si(Me)₂— |
| 756 | Ti | Cl | 2-(2-Fu) | 5-i-Pr, 9-i-Pr | 3 | 2-(2-Fu) | 4-I-Pr, 7-I-Pr | 3 | —Si(Me)₂— |
| 757 | Zr | Cl | 2-(2-Fu) | 5-t-Bu, 9-t-Bu | 3 | 2-(2-Fu) | 4-t-Bu, 7-t-Bu | 3 | —Si(Me)₂— |
| 758 | Zr | Cl | 2-(2-Fu) | 5-Ph, 9-Ph | 3 | 2-(2-Fu) | 4-Ph, 7-Ph | 3 | —Si(Me)₂— |
| 759 | Zr | Cl | 2-(2-Fu) | 5-Ph, 9-Me | 3 | 2-(2-Fu) | 3-Ph, 7-Me | 3 | —Si(Me)₂— |
| 760 | Zr | Cl | 2-(2-Fu) | 5-Me, 9-Me | 3 | 2-(2-Fu) | 4-Me, 7-Me | 3 | —Si(Me)₂— |
| 761 | Zr | Cl | 2-(2-Fu) | 5-Me, 9-Me | 3 | 2-(2-Fu) | 4-Me, 7-Me | 2 | —Si(Me)₂— |
| 762 | Zr | Me | 2-(2-Fu) | 5-Ph | 2 | 2-(2-Fu) | 4-Ph | 2 | —Si(Me)₂— |
| 763 | Zr | Bzl | 2-(2-Fu) | 5-Ph | 2 | 2-(2-Fu) | 4-Ph | 2 | —Si(Me)₂— |
| 764 | Hf | Cl | 2-(2-Fu) | 5-Ph | 2 | 2-(2-Fu) | 4-Ph | 2 | —Si(Me)₂— |
| 765 | Ti | Cl | 2-(2-Fu) | 5-Ph | 2 | 2-(2-Fu) | 4-Ph | 2 | —Si(Me)₂— |
| 766 | Hf | Cl | 2-(2-Fu) | 3-Me, 9-Me | 3 | 2-(2-Fu) | 3-Me, 7-Me | 3 | —Si(Me)₂— |
| 767 | Ti | Cl | 2-(2-Fu) | 3-Me, 9-Me | 3 | 2-(2-Fu) | 3-Me, 7-Me | 3 | —Si(Me)₂— |
| 768 | Zr | Cl | 2-(3-Fu) | 5-Ph | 2 | 2-(3-Fu) | 4-Ph | 2 | —Si(Me)₂— |
| 769 | Zr | Cl | 2-(3-Fu) | 5-Ph | 2 | 2-(3-Fu) | 4-Ph | 2 | —Si(Me)₂— |
| 770 | Zr | Cl | 2-[2-(3-Me-Fu)] | 5-Ph | 2 | 2-[2-(3-Me—Fu)] | 4-Ph | 2 | —Si(Me)₂— |
| 771 | Zr | Cl | 2-[2-(3-Me-Fu)] | — | 1 | 2-[2-(3-Me—Fu)] | — | 1 | —Si(Me)₂— |
| 772 | Zr | Cl | 2-(2-Thie) | 5-Ph | 2 | 2-(2-Thie) | 4-Ph | 2 | —Si(Me)₂— |
| 773 | Zr | Cl | 2-(2-Thie) | — | 1 | 2-(2-Thie) | — | 1 | —Si(Me)₂— |
| 774 | Zr | Cl | 2-(2-Py) | 5-Ph | 2 | 2-(2-Py) | 4-Ph | 2 | —Si(Me)₂— |
| 775 | Zr | Cl | 2-(2-(Py) | — | 1 | 2-(2-Py) | — | 1 | —Si(Me)₂— |

TABLE 18-continued

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 776 | Zr | Cl | 2-(2-BzFu) | 5-Ph | 2 | 2-(2-(BzFu) | 4-Ph | 2 | —Si(Me)₂— |
| 777 | Zr | Cl | 2-(2-BzFu) | — | 1 | 2-(2-(BzFu) | — | 1 | —Si(Me)₂— |
| 778 | Zr | Cl | 2-[2-(N-Me-Pyr)] | 5-Ph | 2 | 2-[2-(N-Me—Pyr)] | 4-Ph | 2 | —Si(Me)₂— |
| 779 | Zr | Cl | 2-[2-(N-Me-Pyr)] | — | 1 | 2-[2-(N-Me—Pyr)] | — | 1 | —Si(Me)₂— |

TABLE 19

| | | | CA¹: Cyclopentadiene | | | CA²: Cyclopentadiene | | | |
|---|---|---|---|---|---|---|---|---|---|
| No. | M | X | Ra | R¹ | p + m | Ra | R¹ | q + n | Y |
| 780 | Zr | Cl | 2-(2-Fu) | — | 1 | 3-(2-Fu) | — | 1 | —GeH₂— |
| 781 | Zr | Cl | 2-(2-Fu) | — | 1 | 2-(2-Fu) | — | 1 | —Ge(Me)₂— |
| 782 | Zr | Cl | 2-(2-Fu) | 9-Me | 2 | 2-(2-Fu) | 9-Me | 2 | —Ge(Me)₂— |
| 783 | Zr | Cl | 2-(2-Fu) | 5-Me | 2 | 2-(2-Fu) | 5-Me | 2 | —Ge(Me)₂— |
| 784 | Zr | Cl | 2-(2-Fu) | 3-Me | 2 | 2-(2-Fu) | 3-Me | 2 | —Ge(Me)₂— |
| 785 | Zr | Cl | 2-(2-Fu) | 3-Me, 9-Me | 3 | 2-(2-Fu) | 3-Me, 9-Me | 3 | —Ge(Me)₂— |
| 786 | Zr | Cl | 2-(2-Fu) | 5-Me, 9-Me | 3 | 2-(2-Fu) | 5-Me, 9-Me | 3 | —Ge(Me)₂— |
| 787 | Zr | Cl | 2-(2-Fu) | 5-Cl | 2 | 2-(2-Fu) | 5-Cl | 2 | —Ge(Me)₂— |
| 788 | Zr | Cl | 2-(2-Fu) | 5-Et | 2 | 2-(2-Fu) | 5-Et | 2 | —Ge(Me)₂— |
| 789 | Zr | Cl | 2-(2-Fu) | 5-i-Pr | 2 | 2-(2-Fu) | 5-i-Pr | 2 | —Ge(Me)₂— |
| 790 | Zr | Cl | 2-(2-Fu) | 5-t-Bu | 2 | 2-(2-Fu) | 5-t-Bu | 2 | —Ge(Me)₂— |
| 791 | Zr | Cl | 2-(2-Fu) | 5-Ph | 2 | 2-(2-Fu) | 5-Ph | 2 | —Ge(Me)₂— |
| 792 | Zr | Cl | 2-(2-Fu) | 5-Np | 2 | 2-(2-Fu) | 5-Np | 2 | —Ge(Me)₂— |
| 793 | Zr | Cl | 2-(2-Fu) | 5-OMe | 2 | 2-(2-Fu) | 5-OMe | 2 | —Ge(Me)₂— |
| 794 | Zr | Cl | 2-(2-Fu) | 5-OPh | 2 | 2-(2-Fu) | 5-OPh | 2 | —Ge(Me)₂— |
| 795 | Zr | Cl | 2-(2-Fu) | 5-Bzl | 2 | 2-(2-Fu) | 5-Bzl | 2 | —Ge(Me)₂— |
| 796 | Zr | Cl | 2-(2-Fu) | 5-Tol | 2 | 2-(2-Fu) | 5-Tol | 2 | —Ge(Me)₂— |
| 797 | Zr | Cl | 2-(2-Fu) | 5-(OBzl) | 2 | 2-(2-Fu) | 5-(OBzl) | 2 | —Ge(Me)₂— |
| 798 | Zr | Cl | 2-(2-Fu) | 5-TMS | 2 | 2-(2-Fu) | 5-TMS | 2 | —Ge(Me)₂— |
| 799 | Zr | Cl | 2-(2-Fu) | 5-(1-Pyr) | 2 | 2-(2-Fu) | 5-(1-Pyr) | 2 | —Ge(Me)₂— |
| 800 | Zr | Cl | 2-(2-Fu) | 5-(1-Indo) | 2 | 2-(2-Fu) | 5-(1-Indo) | 2 | —Ge(Me)₂— |
| 801 | Zr | Cl | 2-(2-Fu), 5-(2-Fu) | — | 2 | 2-(2-Fu), 5-(2-Fu) | — | 2 | —Ge(Me)₂— |
| 802 | Zr | Me | 2-(2-Fu), 5-(2-Thie) | — | 2 | 2-(2-Fu), 5-(2-Thie) | — | 2 | —Ge(Me)₂— |
| 803 | Zr | Bzl | 2-(2-Fu), 5-(2-BzFu) | — | 2 | 2-(2-Fu), 5-(2-BzFu) | — | 2 | —Ge(Me)₂— |
| 804 | Hf | Cl | 2-(2-Fu), 5-(2-Py) | — | 2 | 2-(2-Fu), 5-(2-Py) | — | 2 | —Ge(Me)₂— |
| 805 | Ti | Cl | 2-(2-Fu), 5-[2-(1-MePyr) | — | 2 | 2-(2-Fu), 5-[2-(1-MePyr) | — | 2 | —Ge(Me)₂— |
| 806 | Hf | Cl | 2-(2-Fu) | 5-Et, 9-Et | 3 | 2-(2-Fu) | 5-Et, 9-Et | 3 | —Ge(Me)₂— |
| 807 | Ti | Cl | 2-(2-Fu) | 5-i-Pr, 9-i-Pr | 3 | 2-(2-Fu) | 5-i-Pr, 9-i-Pr | 3 | —Ge(Me)₂— |
| 808 | Zr | Cl | 2-(2-Fu) | 5-t-Bu, 9-t-Bu | 3 | 2-(2-Fu) | 5-t-Bu, 9-t-Bu | 3 | —Ge(Me)₂— |
| 809 | Zr | Cl | 2-(2-Fu) | 5-Ph, 9-Ph | 3 | 2-(2-Fu) | 5-Ph, 9-Ph | 3 | —Ge(Me)₂— |
| 810 | Zr | Cl | 2-(2-Fu) | 5-Ph, 9-Me | 3 | 2-(2-Fu) | 3-Ph, 9-Me | 3 | —Ge(Me)₂— |
| 811 | Zr | Cl | 2-(2-Fu) | 5-Me, 9-Me | 3 | 2-(2-Fu) | 5-Me, 9-Me | 3 | —Ge(Me)₂— |
| 812 | Zr | Cl | 2-(2-Fu) | 5-Me, 9-Me | 3 | 2-(2-Fu) | 5-Me, 9-Me | 2 | —Ge(Me)₂— |
| 813 | Zr | Me | 2-(2-Fu) | 5-Ph | 2 | 2-(2-Fu) | 5-Ph | 2 | —Ge(Me)₂— |
| 814 | Zr | Bzl | 2-(2-Fu) | 5-Ph | 2 | 2-(2-Fu) | 5-Ph | 2 | —Ge(Me)₂— |
| 815 | Hf | Cl | 2-(2-Fu) | 5-Ph | 2 | 2-(2-Fu) | 5-Ph | 2 | —Ge(Me)₂— |
| 816 | Ti | Cl | 2-(2-Fu) | 5-Ph | 2 | 2-(2-Fu) | 5-Ph | 2 | —Ge(Me)₂— |
| 817 | Hf | Cl | 2-(2-Fu) | 3-Me, 9-Me | 3 | 2-(2-Fu) | 3-Me, 9-Me | 3 | —Ge(Me)₂— |
| 818 | Ti | Cl | 2-(2-Fu) | 3-Me, 9-Me | 3 | 2-(2-Fu) | 3-Me, 9-Me | 3 | —Ge(Me)₂— |
| 819 | Zr | Cl | 2-(3-Fu) | 5-Ph | 2 | 2-(3-Fu) | 5-Ph | 2 | —Ge(Me)₂— |
| 820 | Zr | Cl | 2-(3-Fu) | 5-Ph | 2 | 2-(3-Fu) | 5-Ph | 2 | —Ge(Me)₂— |
| 821 | Zr | Cl | 2-[2-(3-Me-Fu)] | 5-Ph | 2 | 2-[2-(3-Me—Fu)] | 5-Ph | 2 | —Ge(Me)₂— |
| 822 | Zr | Cl | 2-[2-(3-Me-Fu)] | — | 1 | 2-[2-(3-Me—Fu)] | — | 1 | —Ge(Me)₂— |
| 823 | Zr | Cl | 2-(2-Thie) | 5-Ph | 2 | 2-(2-Thie) | 5-Ph | 2 | —Ge(Me)₂— |
| 824 | Zr | Cl | 2-(2-Thie) | — | 1 | 2-(2-Thie) | — | 1 | —Ge(Me)₂— |
| 825 | Zr | Cl | 2-(2-Py) | 5-Ph | 2 | 2-(2-Py) | 5-Ph | 2 | —Ge(Me)₂— |
| 826 | Zr | Cl | 2-(2-Py) | — | 1 | 2-(2-Py) | — | 1 | —Ge(Me)₂— |
| 827 | Zr | Cl | 2-(2-BzFu) | 5-Ph | 2 | 2-(2-BzFu) | 5-Ph | 2 | —Ge(Me)₂— |
| 828 | Zr | Cl | 2-(2-BzFu) | — | 1 | 2-(2-BzFu) | — | 1 | —Ge(Me)₂— |
| 829 | Zr | Cl | 2-[2-(N-Me-Pyr)] | 5-Ph | 2 | 2-[2-(N-Me—Pyr)] | 5-Ph | 2 | —Ge(Me)₂— |
| 830 | Zr | Cl | 2-[2-(N-Me-Pyr)] | — | 1 | 2-[2-(N-Me—Pyr)] | — | 1 | —Ge(Me)₂— |

TABLE 20

| | | | CA¹: Cyclopentadiene | | | Z: —(R¹)N— | |
|---|---|---|---|---|---|---|---|
| No. | M | X | Ra | R¹ | p + m | R¹ | Y |
| 831 | Ti | Cl | 2-(2-Fu) | — | 1 | t-Bu | —SiH$_2$— |
| 832 | Ti | Cl | 2-(2-Fu) | — | 1 | t-Bu | —Si(Me)$_2$— |
| 833 | Ti | Cl | 2-(2-Fu) | 5-Me | 2 | t-Bu | —Si(Me)$_2$— |
| 834 | Ti | Cl | 2-(2-Fu) | 4-Me | 2 | t-Bu | —Si(Me)$_2$— |
| 835 | Ti | Cl | 2-(2-Fu) | 4-OMe | 2 | t-Bu | —Si(Me)$_2$— |
| 836 | Ti | Cl | 2-(2-Fu) | 4-OPh | 2 | t-Bu | —Si(Me)$_2$— |
| 837 | Ti | Cl | 2-(2-Fu) | 4-Bzl | 2 | t-Bu | —Si(Me)$_2$— |
| 838 | Ti | Cl | 2-(2-Fu) | 4-Tol | 2 | t-Bu | —Si(Me)$_2$— |
| 839 | Ti | Cl | 2-(2-Fu) | 4-OBzl | 2 | t-Bu | —Si(Me)$_2$— |
| 840 | Ti | Cl | 2-(2-Fu) | 4-TMS | 2 | t-Bu | —Si(Me)$_2$— |
| 841 | Ti | Cl | 2-(2-Fu) | 4-(1-Pyr) | 2 | t-Bu | —Si(Me)$_2$— |
| 842 | Ti | Cl | 2-(2-Fu) | 4-(1-Indo) | 2 | t-Bu | —Si(Me)$_2$— |
| 843 | Ti | Cl | 2-(2-Fu) | 3-Me | 2 | t-Bu | —Si(Me)$_2$— |
| 844 | Ti | Cl | 2-(2-Fu) | 3-Me, 5-Me | 3 | t-Bu | —Si(Me)$_2$— |
| 845 | Ti | Cl | 2-(2-Fu) | 4-Me, 5-Me | 3 | t-Bu | —Si(Me)$_2$— |
| 846 | Ti | Cl | 2-(2-Fu) | 4-Et, 5-Me | 3 | t-Bu | —Si(Me)$_2$— |
| 847 | Ti | Cl | 2-(2-Fu) | 4-(i-Pr), 5-Me | 3 | t-Bu | —Si(Me)$_2$— |
| 848 | Ti | Cl | 2-(2-Fu) | 4-(t-Bu), 5-Me | 3 | t-Bu | —Si(Me)$_2$— |
| 849 | Ti | Cl | 2-(2-Fu) | 4-Ph, 5-Me | 3 | t-Bu | —Si(Me)$_2$— |
| 850 | Ti | Cl | 2-(2-Fu) | 3-Ph, 5-Me | 3 | t-Bu | —Si(Me)$_2$— |
| 851 | Ti | Cl | 2-(2-Fu) | 4-Me, 5-Me | 3 | Ph | —Si(Me)$_2$— |
| 852 | Ti | Cl | 2-(2-Fu) | 4-Me, 5-Me | 3 | Me | —Si(Me)$_2$— |
| 853 | Ti | Cl | 2-(2-Fu) | 4-Me, 5-Me | 3 | Me | —Si(Me)$_2$— |
| 854 | Ti | Me | 2-(2-Fu) | 4-Me, 5-Me | 3 | Me | —Si(Me)$_2$— |
| 855 | Ti | Bzl | 2-(2-Fu) | 4-Me, 5-Me | 3 | Me | —Si(Me)$_2$— |
| 856 | Hf | Cl | 2-(2-Fu) | 4-Me, 5-Me | 3 | Me | —Si(Me)$_2$— |
| 857 | Zr | Cl | 2-(2-Fu) | 4-Me, 5-Me | 3 | Me | —Si(Me)$_2$— |
| 858 | Hf | Cl | 2-(2-Fu) | 3-Me, 5-Me | 3 | Me | —Si(Me)$_2$— |
| 859 | Zr | Cl | 2-(2-Fu) | 3-Me, 5-Me | 3 | Me | —Si(Me)$_2$— |
| 860 | Hf | Cl | 2-(2-Fu) | 4-Me, 5-Me | 3 | t-Bu | —Si(Me)$_2$— |
| 861 | Zr | Cl | 2-(2-Fu) | 4-Me, 5-Me | 3 | t-Bu | —Si(Me)$_2$— |
| 862 | Hf | Me | 2-(2-Fu) | 3-Me, 5-Me | 3 | t-Bu | —Si(Me)$_2$— |
| 863 | Zr | Bzl | 2-(2-Fu) | 3-Me, 5-Me | 3 | t-Bu | —Si(Me)$_2$— |
| 864 | Ti | Cl | 2-(3-Fu) | 4-Me, 5-Me | 3 | t-Bu | —Si(Me)$_2$— |
| 865 | Ti | Cl | 2-(3-Fu) | 3-Me, 5-Me | 3 | Me | —Si(Me)$_2$— |
| 866 | Ti | Cl | 2-[2-(3-Me—Fu)] | 4-Me, 5-Me | 3 | t-Bu | —Si(Me)$_2$— |
| 867 | Ti | Cl | 2-[2-(3-Me—Fu)] | 3-Me, 5-Me | 3 | Me | —Si(Me)$_2$— |
| 868 | Ti | Cl | 2-(2-Thie) | 4-Me, 5-Me | 3 | t-Bu | —Si(Me)$_2$— |
| 869 | Ti | Cl | 2-(2-Thie) | 3-Me, 5-Me | 3 | Me | —Si(Me)$_2$— |
| 870 | Ti | Cl | 2-(2-Py) | 4-Me, 5-Me | 3 | t-Bu | —Si(Me)$_2$— |
| 871 | Ti | Cl | 2-(2-Py) | 3-Me, 5-Me | 3 | Me | —Si(Me)$_2$— |
| 872 | Ti | Cl | 2-(2-BzFu) | 4-Me, 5-Me | 3 | t-Bu | —Si(Me)$_2$— |
| 873 | Ti | Me | 2-(2-BzFu) | 3-Me, 5-Me | 3 | Me | —Si(Me)$_2$— |
| 874 | Ti | Bzl | 2-[2-(1-Me—Pyr)] | 4-Me, 5-Me | 3 | t-Bu | —Si(Me)$_2$— |
| 875 | Ti | Cl | 2-[2-(1-Me—Fu)] | 3-Me, 5-Me | 3 | Me | —Si(Me)$_2$— |

TABLE 21

| | | | CA¹: Cyclopentadiene | | | Z: —(R¹)N— | |
|---|---|---|---|---|---|---|---|
| No. | M | X | Ra | R¹ | p + m | R¹ | Y |
| 876 | Ti | Cl | 2-(2-Fu) | — | 1 | t-Bu | —GeH$_2$— |
| 877 | Ti | Cl | 2-(2-Fti) | — | 1 | t-Bu | —Ge(Me)$_2$— |
| 878 | Ti | Cl | 2-(2-Fu) | 5-Me | 2 | t-Bu | —Ge(Me)$_2$— |
| 879 | Ti | Cl | 2-(2-Fu) | 4-Me | 2 | t-Bu | —Ge(Me)$_2$— |
| 880 | Ti | Cl | 2-(2-Fu) | 4-OMe | 2 | t-Bu | —Ge(Me)$_2$— |
| 881 | Ti | Cl | 2-(2-Fu) | 4-OPh | 2 | t-Bu | —Ge(Me)$_2$— |
| 882 | Ti | Cl | 2-(2-Fu) | 4-Bzl | 2 | t-Bu | —Ge(Me)$_2$— |
| 883 | Ti | Cl | 2-(2-Fu) | 4-Tol | 2 | t-Bu | —Ge(Me)$_2$— |
| 884 | Ti | Cl | 2-(2-Fu) | 4-OBzl | 2 | t-Bu | —Ge(Me)$_2$— |
| 885 | Ti | Cl | 2-(2-Fu) | 4-TMS | 2 | t-Bu | —Ge(Me)$_2$— |
| 886 | Ti | Cl | 2-(2-Fu) | 4-(1-Pyr) | 2 | t-Bu | —Ge(Me)$_2$— |
| 887 | Ti | Cl | 2-(2-Fu) | 4-(1-Indo) | 2 | t-Bu | —Ge(Me)$_2$— |
| 888 | Ti | Cl | 2-(2-Fu) | 3-Me | 2 | t-Bu | —Ge(Me)$_2$— |
| 889 | Ti | Cl | 2-(2-Fu) | 3-Me, 5-Me | 3 | t-Bu | —Ge(Me)$_2$— |
| 890 | Ti | Cl | 2-(2-Fu) | 4-Me, 5-Me | 3 | t-Bu | —Ge(Me)$_2$— |
| 891 | Ti | Cl | 2-(2-Fu) | 4-Et, 5-Me | 3 | t-Bu | —Ge(Me)$_2$— |
| 892 | Ti | Cl | 2-(2-Fu) | 4-(i-Pr), 5-Me | 3 | t-Bu | —Ge(Me)$_2$— |
| 893 | Ti | Cl | 2-(2-Fu) | 4-(t-Bu), 5-Me | 3 | t-Bu | —Ge(Me)$_2$— |
| 894 | Ti | Cl | 2-(2-Fu) | 4-Ph, 5-Me | 3 | t-Bu | —Ge(Me)$_2$— |
| 895 | Ti | Cl | 2-(2-Fu) | 3-Ph, 5-Me | 3 | t-Bu | —Ge(Me)$_2$— |
| 896 | Ti | Cl | 2-(2-Fu) | 4-Me, 5-Me | 3 | Ph | —Ge(Me)$_2$— |
| 897 | Ti | Cl | 2-(2-Fu) | 4-Me, 5-Me | 3 | Me | —Ge(Et)$_2$— |

TABLE 21-continued

| | | | CA¹: Cyclopentadiene | | Z: —(R¹)N— | |
|---|---|---|---|---|---|---|
| No. | M | X | Ra | R¹ | p + m | R¹ | Y |
| 898 | Ti | Cl | 2-(2-Fu) | 4-Me, 5-Me | 3 | Me | —Ge(Ph)₂— |
| 899 | Ti | Me | 2-(2-Fu) | 4-Me, 5-Me | 3 | Me | —Ge(Me)₂— |
| 900 | Ti | Bzl | 2-(2-Fu) | 4-Me, 5-Me | 3 | Me | —Ge(Me)₂— |
| 901 | Hf | Cl | 2-(2-Fu) | 4-Me, 5-Me | 3 | Me | —Ge(Me)₂— |
| 902 | Zr | Cl | 2-(2-Fu) | 4-Me, 5-Me | 3 | Me | —Ge(Me)₂— |
| 903 | Hf | Cl | 2-(2-Fu) | 3-Me, 5-Me | 3 | Me | —Ge(Me)₂— |
| 904 | Zr | Cl | 2-(2-Fti) | 3-Me, 5-Me | 3 | Me | —Ge(Me)₂— |
| 905 | Hf | Cl | 2-(2-Fu) | 4-Me, 5-Me | 3 | t-Bu | —Ge(Me)₂— |
| 906 | Zr | Cl | 2-(2-Fu) | 4-Me, 5-Me | 3 | t-Bu | —Ge(Me)₂— |
| 907 | Hf | Cl | 2-(2-Fu) | 3-Me, 5-Me | 3 | t-Bu | —Ge(Me)₂— |
| 908 | Zr | Cl | 2-(2-Fu) | 3-Me, 5-Me | 3 | t-Bu | —Ge(Me)₂— |
| 909 | Ti | Cl | 2-(3-Fu) | 4 Me, 5 Me | 3 | t-Bu | —Ge(Me)₂— |
| 910 | Ti | Cl | 2-(3-Fu) | 3 Me, 5 Me | 3 | Me | —Ge(Me)₂— |
| 911 | Ti | Cl | 2-[2-(3-Me—Fu)] | 4 Me, 5 Me | 3 | t-Bu | —Ge(Me)₂— |
| 912 | Ti | Cl | 2-[2-(3-Me—Fu)] | 3 Me, 5 Me | 3 | Me | —Ge(Me)₂— |
| 913 | Ti | Cl | 2-(2-Thie) | 4 Me, 5 Me | 3 | t-Bu | —Ge(Me)₂— |
| 914 | Ti | Cl | 2-(2-Thie) | 3 Me, 5 Me | 3 | Me | —Ge(Me)₂— |
| 915 | Ti | Cl | 2-(2-Py) | 4-Me, 5-Me | 3 | t-Bu | —Ge(Me)₂— |
| 916 | Ti | Cl | 2-(2-Py) | 3-Me, 5-Me | 3 | Me | —Ge(Me)₂— |
| 917 | Ti | Cl | 2-(2-BzFu) | 4-Me, 5-Me | 3 | t-Bu | —Ge(Me)₂— |
| 918 | Ti | Cl | 2-(2-BzFu) | 3-Me, 5-Me | 3 | Me | —Ge(Me)₂— |
| 919 | Ti | Cl | 2-[2-(1-Me—Pyr)] | 4-Me, 5-Me | 3 | t-Bu | —Ge(Me)₂— |
| 920 | Ti | Cl | 2-[2-(1-Me—Pyr)] | 3-Me, 5-Me | 3 | Me | —Ge(Me)₂— |

What is claimed is:

1. A metallocene compound represented by the following formula (1)

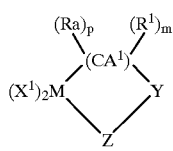

(1)

wherein CA¹ represents a substituted cycloalkadienyl group selected from the group consisting of a substituted cyclopentadienyl group, a substituted indenyl group, a substituted tetrahydroindenyl group, a substituted benzoindenyl group and a substituted fluorenyl group;

each Ra represents independently a heteroaromatic group selected from the group consisting of furyl, thienyl, pyridyl, benzofuryl, benzothienyl, quinolyl, pyrrolyl having a bond at positions other than the 1-position and indolyl having a bond at positions other than the 1-position;

each R¹ represents independently a halogen atom, a hydrocarbon group of 1–20 carbons, a halogenated hydrocarbon group wherein a part or all of the hydrogen atoms in the hydrocarbon group are substituted by a halogen atom, a silyl group substituted by said hydrocarbon group or said halogenated hydrocarbon group, an amino group substituted by said hydrocarbon group or a monocyclic or polycyclic amino group;

p is an integer of 1–8;

m is 0 or an integer of 1–8;

Z represents a linking group selected from the group consisting of (CA²) (Ra)$_q$(R¹)$_n$, —O—, —S—, —NR¹— and —PR¹— wherein CA² represents an unsubstituted or substituted cycloalkadienyl group; Ra and R¹ have the same meanings as defined above, Ra may be identical with or different from said Ra on CA¹ and R¹ may be identical with or different from said R¹ on CA¹; and q and n are each independently 0 or an integer of 1–8;

Y represents a divalent linking group selected from the group consisting of —C(R²)₂—, —C₂(R²)₄—, —C₆(R²)₁₀—, —C₆(R²)₄—, —Si(R²)₂—, —Ge(R²)₂— and —Sn(R²)₂— wherein each R² represents independently a hydrogen atom, a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group;

M represents a transition metal atom selected from the group consisting of Ti, Zr and Hf; and each X¹ represents independently a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group provided that Ra is not pyridyl, quinolyl or furyl when present on the 6-member ring of the substituted indenyl group and that Ra is not pyridyl when CA¹ is a substituted cyclopentadienyl group.

2. The metallocene compound set froth in claim 1 represented by the following formula (2)

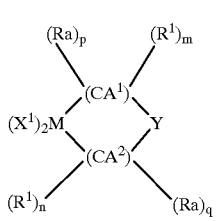

(2)

wherein CA¹, CA², Ra, R¹, p, q, m, n, (q+n), Y, M and X¹ have each the meanings as defined above, in which Z in formula (1) is (CA²) (Ra)$_q$(R¹)$_n$.

3. The metallocene compound set forth in claim 1 represented by the following formula (2A)

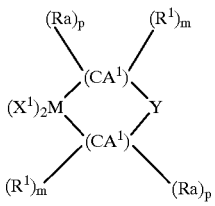
(2A)

wherein $CA^1$, Ra, $R^1$, p, m, Y, M and $X^1$ have each the meanings as defined above, in which $CA^2$, q and n in formula (2) are each identical with $CA^1$, p and m, which is a racemic form consisting of a stereostructurally unsymmetrical compound with respect to M and its enantiomer, a stereostructurally symmetrical meso form or the mixture thereof.

4. A metallocene compound represented by the following formula (1)

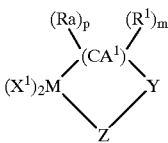
(1)

wherein $CA^1$ represents a substituted cycloalkadienyl group selected from the group consisting of a substituted cyclopentadienyl group, a substituted indenyl group, a substituted tetrahydroindenyl group, a substituted benzoindenyl group and a substituted fluorenyl group;

each Ra represents independently a monocyclic or polycyclic heteroaromatic group containing a heteroatom selected from the group consisting of an oxygen atom, a sulfur atom and a nitrogen atom in a 5- or 6-membered ring;

each $R^1$ represents independently a halogen atom, a hydrocarbon group of 1–20 carbons, a halogenated hydrocarbon group wherein a part or all of the hydrogen atoms in the hydrocarbon group are substituted by a halogen atom, a silyl group substituted by said hydrocarbon group or said halogenated hydrocarbon group, an amino group substituted by said hydrocarbon group or a monocyclic or polycyclic amino group;

p is an integer of 1–8;

m is 0 or an integer of 1–8;

Z represents a linking group selected from the group consisting of $(CA^2)$ $(Ra)_q(R^1)_n$, —O—, —S—, —$NR^1$— and —$PR^1$— wherein $CA^2$ represents an unsubstituted or substituted cycloalkadienyl group; Ra and $R^1$ have the same meanings as defined above, Ra may be identical with or different from said Ra on $CA^1$ and $R^1$ may be identical with or different from said $R^1$ on $CA^1$; and q and n are each independently 0 or an integer of 1–8;

Y represents a divalent linking group selected from the group consisting of —$C(R^2)_2$—, —$C_2(R^2)_4$—, —$C_6(R^2)_{10}$—, —$C_6(R^2)_4$—, —$Si(R^2)_2$—, —$Ge(R^2)_2$— and —$Sn(R^2)_2$— wherein each $R^2$ represents independently a hydrogen atom, a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group;

M represents a transition metal atom selected from the group consisting of Ti, Zr and Hf; and each $X^1$ represents independently a halogen atom, a hydrocarbon group of 1–20 carbons, a halogenated hydrocarbon group wherein a part or all of the hydrogen atoms in the hydrocarbon group are substituted by a halogen atom or a silyl group substituted by said hydrocarbon group or said halogenated hydrocarbon group;

provided that at least one of Ra is present on the 5-membered ring in the substituted cycloalkadienyl group.

5. The metallocene compound set forth in claim 1 or 4 wherein at least one of Ra is present at the 2- or 3-position of a substituted cyclopentadienyl group, a substituted indenyl group, a substituted tetrahydroindenyl group or a substituted benzoindenyl group.

6. The metallocene compound set forth in claim 1 or 4 wherein the hydrocarbon group of 1–20 carbons as defined in $R^1$, $R^2$ and $X^1$ is an alkyl group of 1–20 carbons, an aryl group of 6–20 carbons, an aralkyl group of 7–20 carbons, an alkoxy group of 1–20 carbons, an aryloxy group of 6–20 carbons or an aralkyloxy group of 7–20 carbons.

7. The metallocene compound of claims 1 or 4 wherein each of $CA^1$ and $CA^2$ is a substituted cyclopentadienyl group or a substituted indenyl group; Ra is furyl or thienyl present at 2-position of $CA^1$ and $CA^2$ or furyl or thienyl present at 3-position of $CA^1$ and $CA^2$;

M is Ti, Zr or Hf;

$X^1$ is a chlorine atom; and

Y is a dimethylsilylene group.

8. The metallocene compound set forth in claim 1 or 4 represented by the following formula (3a)

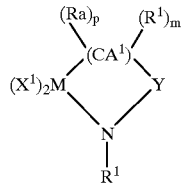
(3a)

wherein $CA^1$, Ra, $R^1$, p, m, Y, M and $X^1$ have respectively the meanings as defined above, in which Z in formula (1) is —($R^1$)N—.

9. A process for the preparation of the metallocene compound of claims 1 or 4, which comprises:

(a) reacting a substituted cycloalkadiene anion represented by the following formula (4Aa)

$(Ra)_p(R^1)_m(CA^1)^-$— (4Aa)

with a binding agent represented by the following formula (5A) at a molar ratio of 2:1,

$X^2$—Y—$X^2$m (5A)

wherein Y has the meaning as defined in claims 1 or 27 and $X^2$ represents a hydrogen atom or a halogen atom, said substituted cycloalkadiene anion being prepared by reacting a substituted cycloalkadiene represented by the following formula (4A)

$$(Ra)_p(R^1)_m(CA^1)H \qquad (4A)$$

wherein $CA^1$, Ra, $R^1$, p and m have respectively the meanings as defined above, with a metal salt type base to effect an anionization or by reacting a substituted cycloalkadiene anion represented by following formula (4Aa) with any one of the compounds represented by the following formulas (5B) to (5F) at a molar ratio of 1:1, $$X^2\text{—}Y\text{—}(CA^2)(R^1)_n(Ra)_q \qquad (5B)$$

$$X^2\text{—}Y\text{—}(R^1)NH \qquad (5C)$$

$$X^2\text{—}Y\text{—}OH \qquad (5D)$$

$$X^2\text{—}Y\text{—}SH \qquad (5E)$$

$$X^1\text{—}Y\text{—}(R^1)PH \qquad (5F)$$

in which Y, $CA^2$, Ra, $R^1$ and $X^2$ have respectively the meanings as defined in claims 1 or 27 to form a compound represented by the following formula (6)

$$(Ra)_p(R^1)_m(CA^1)\text{—}Y\text{—}Z^1 \qquad (6)$$

wherein $Z^1$ represents $(CA^1)(R^1)_m(Ra)_p$, $(CA^2)(R^1)_n(Ra)_q$, $(R^1)NH$, —OH, —SH or $(R^1)PH$, and then (b) reacting a dianion represented by the following formula (6A)

$$(Ra)_p(R^1)_m(CA^1)^-\text{—}Y\text{—}Z^-\text{—} \qquad (6A)$$

wherein each symbol has the meaning as defined above, with a transition metal compound represented by the following formula (7)

$$(X^1)_2\text{—}M\text{—}(X^3)_2 \qquad (7)$$

wherein M and $X^1$ have the meaning as defined above and $X^1$ represents hydrogen or a halogen atom, said dianion being prepared by reacting the compound represented by said formula (6) with a metal salt type base to anionize each of the cycloalkadienyl ring and $Z^1$.

10. The process for the preparation of the metallocene compound set forth in claim 8 wherein the substituted cycloalkadiene anion and the binding agent represented by said formula (5A) are allowed to react at a molar ratio of 2:1 in said (a) step to produce the metallocene compound set forth in claim 3 represented by formula (2A).

11. The process for the preparation of the metallocene compound set forth in claim 9 wherein the substituted cycloalkadiene anion and the compound represented by said formula (5B) are allowed to react at a molar ratio of 1:1 in said step (a) to produce the metallocene compound set forth in claim 2 represented by formula (2).

12. The process of claim 9 wherein each of Ra in formulas, (4A) and (5B) is independently furyl, thienyl, pyridyl, benzofiryl, benzothienyl, quinolyl, pyrrolyl having a bond at positions other than the 1-position, or indolyl having a bond at positions other than the 1-position.

13. The process for the preparation of the metallocene compound set forth in claim 9 wherein the compound represented by formula (5A) is dialkylmethylenedichloride, tetraalkylethylenedichloride, dialkylsilylenedichloride, dialkylgermaniumdichloride or dialkylstannyldichloride.

14. The process for the preparation of the metallocene compound set forth in claim 9 wherein the transition metal compound represented by formula (7) is titanium tetrachloride, dialkyl titanium dichloride, zirconium tetrachloride, dialkyl zirconium dichloride, hafnium tetrachloride or dialkyl hafnium dichloride.

15. The process for the preparation of the metallocene compound set forth in claim 9 wherein the metal salt type base is methyllithium, n-butyllithium, t-butyllithium, lithium hydride, sodium hydride or potassium hydride.

16. The process of claim 9 wherein the compound represented by said formula (5B) is prepared by reacting a substituted cycloalkadiene anion represented by the following formula (4Ba)

$$\text{—}^-(CA^2)(R^1)_n(Ra)_q \qquad (4Ba)$$

wherein each symbol has the meaning as defined in claim 28, with a binding agent represented by said formula (5A) at a molar ratio of 1:1, said cycloalkadiene anion being prepared by reacting a substituted cycloalkadiene represented by the following formula (4B)

$$H(CA^2)(R^1)_n(Ra)_q \qquad (4B)$$

wherein each symbol has the meaning as defined in claim 9, with a metal salt type base to effect an anionization.

17. The process of claim 11 wherein the compound represented by formula (5B) is prepared by reacting a substituted cycloalkadiene anion represented by the following formula (4Ba)

$$\text{—}^-(CA^2)(R^1)_n(Ra)_q \qquad (4Ba)$$

wherein each symbol has the meaning defined in claim 9, with a binding agent represented by said formula (5A) at a molar ratio of 1:1, said cycloalkadiene anion being prepared by reacting a substituted cycloalkadiene represented by the following formula (4B)

$$H(CA^2)(R^1)_n(Ra)_q \qquad (4B)$$

wherein each symbol has the meaning as defined in claim 9, with a metal salt type base to effect an anionization.

18. A catalyst for olefin polymerization comprising the metallocene compound set forth in claim 1 or 4 and an aluminoxane.

19. A catalyst for olefin polymerization formed from the metallocene compound set forth in claim 1 or 4, an aluminoxane and a finely divided support.

20. The catalyst for olefin polymerization set forth in claim 19 wherein a reaction product of the metallocene compound and the aluminoxane is carried on the finely divided support.

21. The catalyst for olefin polymerization set forth in claim 19 wherein the finely divided support is an inorganic fine particles.

22. The catalyst according to claim 20 wherein the support is finely divided inorganic particles.

23. A process for the production of an olefin polymer characterized by polymerizing an olefin in the presence of the catalyst for olefin polymerization set forth in claim 18.

24. The process for the production of an olefin polymer set forth in claim 23 wherein the olefin is propylene or a mixed olefin of propylene and other olefins than propylene.

25. A process for the production of an olefin polymer characterized by polymerizing an olefin in the presence of the catalyst for olefin polymerization set forth in claim 19 and an organic aluminum compound.

26. The process for the production of an olefin polymer set forth in claim 25 wherein the olefin is propylene or a mixed olefin of propylene and olefins other than propylene.

27. The process for the production of an olefin polymer set forth in claim 25 wherein the organic aluminum compound is triethylaluminum or tri-iso-butylaluminum.

28. A process for the production of an olefin polymer which comprises polymerizing an olefin in the presence of the catalyst as defined in claim 20 and an organic aluminum compound.

29. A process for the production of an olefin polymer which comprises polymerizing an olefin in the presence of the catalyst as defined in claim 21 and an organic aluminum compound.

30. The process of claim 28 wherein the olefin is propylene or a mixed olefin of propylene and olefins other than propylene.

31. The process of claim 29 wherein the olefin is propylene or a mixed olefin of propylene and olefins other than propylene.

32. The process of claim 28 wherein the organic aluminum compound is triethylaluminum or tri-isobutylaluminum.

33. The process of claim 29 wherein the organic aluminum compound is triethylaluminum or tri-isobutylaluminum.

34. The metallocene compound of claim 27 represented by the following formula (2)

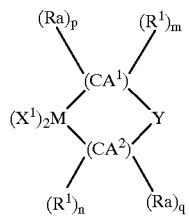

(2)

wherein $CA^1$, $CA^2$, Ra, $R^1$, p, q, m, n, Y, M and $X^1$ have each the meanings as defined in claim 27, in which Z in formula (1) is $(CA^2)(Ra)_q(R^1)_n$.

35. The metallocene compound of claim 27 represented by the following formula (2A)

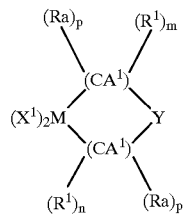

(2a)

wherein $CA^1$, Ra, $R^1$, p, m, Y, M and $X^1$ have each the meanings as defined in claim 27, in which $CA^2$, q and n in formula (2) are each identical with $CA^1$, p and m, which is a racemic form, consisting of a stereostructurally unsymmetrical compound with respect to M and its enantiomer, a stereostructurally symmetrical meso form or the mixture thereof.

* * * * *

UNITED STATES PATENT AND TRADEMARK OFFICE
CERTIFICATE OF CORRECTION

PATENT NO.   : 6,169,051 B1
DATED        : January 2, 2001
INVENTOR(S)  : Seiki Mitani et al.

It is certified that error appears in the above-identified patent and that said Letters Patent is hereby corrected as shown below:

Column 3,
Line 41, change "the substituted cycloalka-" to -- the cycloalka- --;

Column 4,
Line 5, change "benzofliryl" to -- benzofuryl --;
Line 41, change "(dimethylphenyl) methyl, (trimethylphenyl) methyl"
to -- (dimethylphenyl)methyl, (trimethylphenyl)methyl --.

Column 6,
Line 45, delete right top of "$(R^1)_m$"

Column 9,
Line 47, change "$(Ra)_P(R^1)_m(CA^1)$-Y-Z-" to -- $(Ra)_p(R^1)m(CA^1)^-$—Y—$Z^-$– --;

Column 10,
Line 32, change "(Sf)" to -- (5f) --.

Column 14,
Line 10, change "a-olefins" to -- α-olefins --.
Line 51, change "5-propylidene- 5-norbornene" to -- 5-propylidene-5-norbornene --;

Column 16,
Line 13, change "1-(2-furyl)-2, 4-dimethylcyclopenta-diene" to -- 1-(2-furyl)-2, 4-dimethylcyclopentadiene --;

Column 17,
Line 16, change "dimethylsilylenebis" to -- dimethylbis --;
Line 57, change "A 1 l" to -- A 100 ml --;

Column 18,
Line 12, change "dimethlbis" to -- dimethylbis --;
Line 14, change "A 1 l" to -- A 100 ml --;
Line 21, delete "of";
Line 33, change "dimethyl bis[2-(2-furyl)-4,5-dimethyl-" to -- dimethylbis[2-(2-furyl)-4,5-dimethyl- --;
Line 39, change "[2-(2-furyl-)-4,5" to -- [2-(2-furyl)-4,5 --; and Column 21,
Line 43, change "101000" to -- 10,000 --.

UNITED STATES PATENT AND TRADEMARK OFFICE
CERTIFICATE OF CORRECTION

PATENT NO. : 6,169,051 B1
DATED : January 2, 2001
INVENTOR(S) : Seiki Mitani et al.

It is certified that error appears in the above-identified patent and that said Letters Patent is hereby corrected as shown below:

Column 22,
Line 33, change "Me$_2$Si" to -- Me$_2$Si[3-(2-Furyl)-2,5-Me$_2$-Cp]$_2$ZrCl$_2$ --;
Line 35, change "Me$_2$Si(2-Furyl-3,5-Me$_2$-CP)$_2$ZrCl$_2$" to -- Me$_2$Si[2-(2-Furyl)-3,5-Me$_2$-CP]$_2$ZrCl$_2$ --;
Line 39, change "Me$_2$Si(2-Furyl-4,5-Me$_2$-Cp)$_2$ZrCl$_2$" to -- Me$_2$Si[2-(2-Furyl)-4,5-Me$_2$-Cp]$_2$ZrCl$_2$ --;
Line 43, change "Me$_2$Si(3-Thienyl-3,5-Me$_2$-Cp)$_2$ZrCl$_2$" to -- Me$_2$Si[3-(2-Thienyl)-2,5-Me$_2$-Cp]$_2$ZrCl$_2$ --;
Line 47, change "Me$_2$Si(3-Furyl-3,5-Me$_2$Cp)$_2$ZrCl$_2$" to -- Me$_2$Si[2-(2-Furyl)-indenyl]ZrCl$_2$ --;

Columns 21 and 22,
Table 2, in the column headings, change "q+n Y" to -- q+n    Y --;

Columns 23 and 24,
Table 2, in the column headings, change "q+n Y" to -- q+n    Y --;
Table 2, last column for compound No. 21, change "-C(Me)$_2$-" to -- -C(Et)$_2$- --;
Table 2, last column for compound No. 22, change "-C(Me)$_2$-" to -- -C(Ph)$_2$- --;
Table 3, in the column headings, change "q+n Y" to -- q+n    Y --;
Table 3, last column for compound No. 61, change "—C$_2$(Me)$_4$—" to -- —C$_2$(Et)$_4$— --;
Table 3, last column for compound No. 62, change "—C$_2$(Me)$_4$—" to -- —C$_2$(Ph)$_4$— --;

Columns 25 and 26,
Table 3, in the column headings, change "q+n Y" to -- q+n    Y --;
Table 4, in the column headings, change "q+n Y" to -- q+n    Y --;
Table 4, last column for compound No. 101, change "—Si(Me)$_2$—" to -- —Si(Et)$_2$— --;
Table 4, last column for compound No. 102, change "—Si(Me)$_2$—" to -- —Si(Ph)$_2$— --;
Table 5, in the column headings, change "q+n Y" to -- q+n    Y --;

Columns 27 and 28,
Table 5, in the column headings, change "q+n Y" to -- q+n    Y --;
Table 5, last column for compound No. 141, change "—Ge(Me)$_2$—" to -- —Ge(Et)$_2$— --;
Table 5, last column for compound No. 142, change "—Ge(Me)$_2$—" to -- —Ge(Ph)$_2$— --;
Table 6, last column for compound No. 161, change "-GeH$_2$-" to -- -CH$_2$- --;
Table 6, last column for compound No. 162 to No. 180, change "-Ge(Me)$_2$-" to -- -C(Me)$_2$- --;
Table 6, in the second column heading "R$^1$" for compound No. 173, change "3-Me" to -- 2-Me --;

UNITED STATES PATENT AND TRADEMARK OFFICE
CERTIFICATE OF CORRECTION

PATENT NO. : 6,169,051 B1
DATED : January 2, 2001
INVENTOR(S) : Seiki Mitani et al.

It is certified that error appears in the above-identified patent and that said Letters Patent is hereby corrected as shown below:

Columns 27 and 28 (cont'd),
Table 6, in the second column heading "$R^1$" for compound No. 174, change "3-Me, 5-Me" to -- 2-Me, 5-Me --;
Table 6, in the second column heading "$R^1$" for compound No. 180, change "3-Ph, 5-Me" to -- 2-Ph, 5-Me --;
Table 6, last column for compound No. 181, change "-Ge(Me)$_2$-" to -- -C(Et)$_2$- --;
Table 6, last column for compound No. 182, change "—Ge(Me)$_2$—" to -- —Ge(Ph)$_2$— --;
Table 6, last column for compound No. 183 to No. 200, change "-Ge(Me)$_2$-" to
-- -C(Me)$_2$- --;
Table 6, in the second column heading "$R^1$" for compound No. 187, change "3-Me, 5-Me" to -- 2-Me, 5-Me --;
Table 6, in the second column heading "$R^1$" for compound No. 188, change "3-Me, 5-Me" to -- 2-Me, 5-Me --;
Table 6, in the second column heading "$R^1$" for compound No. 190, change "3-Me, 5-Me" to -- 2-Me, 5-Me --;
Table 6, in the second column heading "$R^1$" for compound No. 192, change "3-Me, 5-Me" to -- 2-Me, 5-Me --;
Table 6, in the second column heading "$R^1$" for compound No. 194, change " 3-Me, 5-Me" to -- 2-Me, 5-Me --;
Table 6, in the second column heading "$R^1$" for compound No. 196, change "3-Me, 5-Me" to -- 2-Me, 5-Me --;
Table 6, in the second column heading "$R^1$" for compound No. 198, change "3-Me, 5-Me" to -- 2-Me, 5-Me --;
Table 6, in the second column heading "$R^1$" for compound No. 200, change " 3-Me, 5-Me" to -- 2-Me, 5-Me --;

Columns 29 and 30,
Table 7, in the column headings, change "q+n Y" to -- q+n     Y --;
Table 7, last column for compound No. 221, change "—C$_2$(Me)$_4$—" to -- —C$_2$(Et)$_4$— --;
Table 7, last column for compound No. 222, change "—C$_2$(Me)$_4$—" to -- —C$_2$(Ph)$_4$— --;
Table 8, in the column headings, change "q+n Y" to -- q+n     Y --;
Table 8, last column for compound No. 261, change "—Si(Me)$_2$—" to -- —Si(Et)$_2$— --;
Table 8, last column for compound No. 262, change "—Si(Me)$_2$—" to -- —Si(Ph)$_2$— --;

Columns 31 and 32,
Table 8 in the headings, change "q+n Y" to --q+n         Y--;
Table 9, in the headings, change "q+n Y" to --q+n         Y--;
Table 9, first "$R^1$" column for compound No. 294, change "4-Me, 5-Me" to -- 2-Me, 5-Me --;
Table 9, last column for compound No. 301, change "—Ge(Me)$_2$—" to -- —Ge(Et)$_2$— --;
Table 9, last column for compound No. 302, change "—Ge(Me)$_2$—" to -- —Ge(Ph)$_2$— --;

UNITED STATES PATENT AND TRADEMARK OFFICE
CERTIFICATE OF CORRECTION

PATENT NO.     : 6,169,051 B1
DATED          : January 2, 2001
INVENTOR(S)    : Seiki Mitani et al.

It is certified that error appears in the above-identified patent and that said Letters Patent is hereby corrected as shown below:

<u>Columns 31 and 32 (cont'd),</u>
Table 10, in the headings, change "$CA^1$: Cyclopendadiene" to -- $CA^1$: Indene --;
Table 10, in the headings, change "$CA^2$: Cyclopendadiene" to -- $CA^2$: Indene --;
Table 10, in the headings, change "q+n Y" to -- q+n    Y --;
Table 10, last column for compound No. 321, change "-C(Me)$_2$-" to -- -CH$_2$- --;

<u>Columns 33 and 34,</u>
Table 10, in the headings, change "$CA^1$: Cyclopendadiene" to -- $CA^1$: Indene --;
Table 10, in the headings, change "$CA^2$: Cyclopendadiene" to -- $CA^2$: Indene --;
Table 10, in the headings, change "q+n Y" to -- q+n    Y --;
Table 10, in the second column heading "$R^1$" for compound No. 323, change "5-Me" to -- 7-Me --;
Table 10, in the second column heading "$R^1$" for compound No. 325, change "4-OMe" to -- 3-Me --;
Table 10, in the second column heading "$R^1$" for compound No. 326, change "4-OPh" to -- 3-Me, 7-Me --;
Table 10, in the second column heading "$R^1$" for compound No. 327, change "4-Bzl" to -- 4-Me, 7-Me --;
Table 10, in the second column heading "$R^1$" for compound No. 328, change "4-Tol" to -- 4-Cl --;
Table 10, in the second column heading "$R^1$" for compound No. 329, change "4-OBzl" to -- 4-Et --;
Table 10, in the second column heading "$R^1$" for compound No. 330, change "4-TMS" to -- 4-i-Pr --;
Table 10, in the second column heading "$R^1$" for compound No. 331, change "4-(1-Pyr)" to -- 4-t-Bu --;
Table 10, in the second column heading "$R^1$" for compound No. 332, change "4-(1-Indo)" to -- 4-Ph --;
Table 10, in the second column heading "$R^1$" for compound No. 333, change "2-Me" to -- 4-Np --;
Table 10, in the second column heading "$R^1$" for compound No. 334, change "2-Me, 5-Me" to -- 4-OMe --;
Table 10, in the second column heading "$R^1$" for compound No. 335, change "4-Me, 5-Me" to -- 4-OPh --;
Table 10, in the second column heading "$R^1$" for compound No. 336, change "4-Et, 5-Me" to -- 4-Bzl --;

UNITED STATES PATENT AND TRADEMARK OFFICE
CERTIFICATE OF CORRECTION

| | |
|---|---|
| PATENT NO. : 6,169,051 B1 | |
| DATED : January 2, 2001 | |
| INVENTOR(S) : Seiki Mitani et al. | |

It is certified that error appears in the above-identified patent and that said Letters Patent is hereby corrected as shown below:

<u>Columns 33 and 34 (cont'd),</u>
Table 10, in the second column heading "$R^1$" for compound No. 337, change "4-(i-Pr), 5-Me" to -- 4-Tol --;
Table 10, in the first column heading "$R^1$" for compound No. 338, change "4-Obzl" to -- 4-OBzl --;
Table 10, in the second column heading "$R^1$" for compound No. 338, change "4-(t-Bu), 5-Me" to -- 4-OBzl --;
Table 10, in the second column heading "$R^1$" for compound No. 339, change "4-Ph, 5-Me" to -- 4-TMS --;
Table 10, in the second column heading "$R^1$" for compound No. 340, change "2-Ph, 5-Me" to -- 4-(1-Pyr) --;
Table 10, in the second column heading "$R^1$" for compound No. 341, change "4-Me, 5-Me" to -- 4-(1-Indo) --;
Table 10, last column for compound No. 341, change "-C(Me)$_2$-" to -- -C(Et)$_2$- --;
Table 10, in the second column heading "Ra" for compound No. 342, change "2-(2-Fu)" to -- 2-(2-Fu), 4-(2-Fu) --;
Table 10, in the second column heading "$R^1$" for compound No. 342, delete "4-Me, 5-Me";
Table 10, last column for compound No. 342, change "-C(Me)$_2$-" to -- -C(Ph)$_2$- --;
Table 10, in column "X" for compound No. 343, change "Me" to -- Cl --;
Table 10, in the second column heading "Ra" for compound No. 343, change "2-(2-Fu)" to -- 2-(2-Fu), 4-(2-Thie) --;
Table 10, in the second column heading "$R^1$" for compound No. 343, delete "4-Me, 5- Me";
Table 10, in column "X" for compound No. 344, change "Bzl" to -- Cl --;
Table 10, in the second column heading "Ra" for compound No. 344, change "2-(2-Fu)" to -- 2-(2-Fu), 4-(2-BzFu) --;
Table 10, in the second column heading "$R^1$" for compound No. 344, delete "4-Me, 5-Me";
Table 10, in column "M" for compound 345, change "Hf" to -- Zr --;
Table 10, in the second column heading "Ra" for compound No. 345, change "2-(2-Fu)" to -- 2-(2-Fu), 4-(2-Py) --;
Table 10, in the second column heading "$R^1$" for compound No. 345, delete "4-Me, 5-Me";
Table 10, in column "M" for compound 346, change "Ti" to -- Zr --;
Table 10, in the second column heading "Ra" for compound No. 346, change "2-(2-Fu)" to -- 2-(2-Fu), 4-(1-MePyr) --;

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

<u>Columns 33 and 34 (cont'd),</u>
Table 10, in the second column heading "$R^1$" for compound No. 346, delete "4-Me, 5-Me";
Table 10, in column "M" for compound 347, change "Hf" to -- Zr --;
Table 10, in the second column heading "$R^1$" for compound No. 347, change "2-Me, 5-Me" to -- 4-Et, 7-Et --;
Table 10, in column "M" for compound 348, change "Ti" to -- Zr --;
Table 10, in the second column heading "$R^1$" for compound No. 348, change "2-Me, 5-Me" to -- 4-i-Pr, 7-i-Pr --;
Table 10, in the second column heading "$R^1$" for compound No. 349, change "4-Me, 5-Me" to -- 4-t-Bu, 7-t-Bu --;
Table 10, in the first column heading "$R^1$" for compound No. 350, change "4-Ph, 7-Me" to -- 4-Ph, 7-Ph --;
Table 10, in the second column heading "$R^1$" for compound No. 350, change "2-Me, 5-Me" to -- 4-Ph, 7-Ph --;
Table 10, in the second column heading "$R^1$" for compound No. 351, change "4-Me, 5-Me" to -- 3-Ph, 7-Me --;
Table 10, in the second column heading "$R^1$" for compound No. 352, change "2-Me, 5-Me" to -- 4-Me, 7-Me --;
Table 10, last column for compound No. 352, change "—C(Me)$_2$—" to -- —C(Et)$_2$— --;
Table 10, in the second column heading "$R^1$" for compound No. 353, change "4-Me, 5-Me" to -- 4-Me, 7-Me --;
Table 10, last column for compound No. 353, change "—C(Me)$_2$—" to -- —C(Ph)$_2$— --;
Table 10, in column "X" for compound No. 354, change "Cl" to -- Me --;
Table 10, in the second column heading "$R^1$" for compound No. 354, change "2-Me, 5-Me" to -- 4-Ph --;
Table 10, in column "X" for compound No. 355, change "Cl" to -- Bzl --;
Table 10, in the second column heading "$R^1$" for compound No. 355, change "4-Me, 5-Me" to -- 4-Ph --;
Table 10, in column "M" for compound No. 356, change "Zr" to -- Hf --;
Table 10, in the second column heading "$R^1$" for compound No. 356, change "2-Me, 5-Me" to -- 4-Ph --;
Table 10, in column "M" for compound No. 357, change "Zr" to -- Ti --;
Table 10, in the second column heading "$R^1$" for compound No. 357, change "4-Me, 5-Me" to -- 4-Ph --;
Table 10, in column "M" for compound No. 358, change "Zr" to -- Hf --;
Table 10, in the second column heading "$R^1$" for compound No. 358, change "2-Me, 5-Me" to -- 3-Me, 7-Me --;
Table 10, in column "M" for compound No. 359, change "Zr" to -- Ti --;

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

Columns 33 and 34 (cont'd),
Table 10, in the second column heading "$R^1$" for compound No. 359, change "4-Me, 5-Me" to -- 3-Me, 7-Me --;
Table 10, in the second column heading "$R^1$" for compound No. 360, change "2-Me, 5-Me" to -- 4-Ph --;
Table 11, in the headings, change "$CA^1$: Cyclopendadiene" to -- $CA^1$: Indene --;
Table 11, in the headings, change "$CA^2$: Cyclopendadiene" to -- $CA^2$: Indene --;
Table 11, in the headings, change "q+n Y" to -- q+n   Y --;
Table 11, in the column heading "p+m" for compound No. 377, change "2" to -- 3 --;
Table 11, in the column heading "p+m" for compound No. 378, change "2" to -- 3 --;
Table 11, in the second heading "Ra" for compound 379, change "2-2-Fu)" to -- 2-(2-Fu) --;
Table 11, in both headings "$R^1$" for compound No. 384, change "2-Np" to -- 4-Np --;
Table 11, in both headings "$R^1$" for compound No. 385, change "2-OMe" to -- 4-OMe --;
Table 11, in both headings "$R^1$" for compound No. 386, change "2-Oph" to -- 4-OPh --;
Table 11, in the second column heading "$R^1$" for compound No. 389, change "4-Obzl" to -- 4-OBzl --;

Columns 35 and 36,
Table 11, in the headings, change "$CA^1$: Cyclopendadiene" to -- $CA^1$: Indene --;
Table 11, in the headings, change "$CA^2$: Cyclopendadiene" to -- $CA^2$: Indene --;
Table 11, in the headings, change "q+n Y" to -- q+n   Y --;
Table 11, in the first column heading "Ra" for compound No. 393, change "2-(2-Fu), (4-(2-Fu)" to -- 2-(2-Fu), 4-(2-Fu) --;
Table 11, in column heading "X" for compound No. 394, change "Me" to -- Cl --;
Table 11, in column heading "X" for compound No. 395, change "Bzl" to -- Cl --;
Table 11, in column heading "M" for compound No. 396, change "Hf" to -- Zr --;
Table 11, in column heading "M" for compound No. 397, change "Ti" to -- Zr --;
Table 11, in column heading "M" for compound No. 398, change "Hf" to -- Zr --;
Table 11, in column heading "M" for compound No. 399, change "Ti" to -- Zr --;
Table 11, in the second column heading "Ra" for compound No. 403, change "2-2-(2-Fu)" to -- 2-(2-Fu) --;
Table 11, last column for compound No. 403, change "—$C_2(Me)_4$—" to -- —$C_2(Et)_4$— --;
Table 11, last column for compound No. 404, change "—$C_2(Me)_4$—" to -- —$C_2(Ph)_4$— --;
Table 12, in the headings, change "$CA^1$: Cyclopendadiene" to -- $CA^1$: Indene --;
Table 12, in the headings, change "$CA^2$: Cyclopendadiene" to -- $CA^2$: Indene --;
Table 12, in the headings, change "q+n Y" to -- q+n   Y --;
Table 11, in the first column heading "Ra" for compound No. 413, change "2-[(3-Me-Fu)]" to "2-[2-(3-Me-Fu)]";

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

Columns 35 and 36 (cont'd),
Table 11, in the first column heading "Ra" for compound No. 414, change "2-[(3-Me-Fu)]" to -- 2-[2-(3-Me-Fu)] --;
Table 11, in the second column heading "Ra" for compound No. 419, change "2-(2-BsFu)" to -- 2-(2-BzFu) --;
Table 11, in the second column heading "Ra" for compound No. 420, change "2-(2-BsFu)" to -- 2-(2-BzFu) --;
Table 12, in the both column heading "$R^1$" for compound No. 420, change "4-(OBzl)" to -- 4-OBzl --;
Table 12, in the second heading "Ra" for compound No. 423, change "3-(2-Fu)" to -- 2-(2-Fu) --;
Table 12, in the second column heading "q+n" for compound No. 428, change "2" to -- 3 --;
Table 12, in the second column heading "$R^1$" for compound No. 429, change "3-Me, 7-Me" to -- 4-Me, 7-Me --;
Table 12, in the second column heading "q+n" for compound No. 429, change "2" to -- 3 --;
Table 12, in the second column heading "$R^1$" for compound No. 430, change "4-Me, 7-Me" to -- 4-Cl --;
Table 12, in the second column heading "$R^1$" for compound No. 431, change "4-Cl" to -- 4-Et --;
Table 12, in column heading "X" for compound No. 445, change "Me" to -- Cl --;
Table 12, in column heading "X" for compound No. 446, change "Bzl" to -- Cl --;
Table 12, in column heading "M" for compound No. 447, change "Hf" to --Zr--;
Table 12, in column heading "M" for compound No. 448, change "Ti" to -- Zr --;
Table 12, in column heading "M" for compound No. 449, change "Hf" to -- Zr --;
Table 12, in column heading "M" for compound No. 450, change "Ti" to -- Zr --;
Table 12, last column for compound No. 454, change "—Si(Me)$_2$—" to -- —Si(Et)$_2$— --;
Table 12, in the second column heading "q+n" for compound No. 455, change "2" to -- 3 --;
Table 12, last column for compound No. 455, change "—Si(Me)$_2$—" to -- —Si(Ph)$_2$— --;

Columns 37 and 38,
Table 12, in the headings, change "$CA^1$: Cyclopendadiene" to -- $CA^1$: Indene --;
Table 12, in the headings, change "$CA^2$: Cyclopendadiene" to -- $CA^2$: Indene --;
Table 12, in the headings, change "q+n Y" to -- q+n    Y --;
Table 13, in the headings, change "$CA^1$: Cyclopendadiene" to -- $CA^1$: Indene --;

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

Columns 37 and 38 (cont'd),
Table 13, in the headings, change "$CA^2$: Cyclopendadiene" to -- $CA^2$: Indene --;
Table 13, in the headings, change "q+n Y" to -- q+n     Y --;
Table 13, in the second heading "Ra" for compound No. 474, change "3-(2-Fu)" to
-- 2-(2-Fu) --;
Table 13, in the second column heading "q+n" for compound No. 479, change "2" to -- 3 --;
Table 13, in the second column heading "$R^1$" for compound No. 480, change "3-Me, 7-Me" to -- 4-Me, 7-Me --;
Table 13, in the second column heading "q+n" for compound No. 480, change "2" to -- 3 --;
Table 13, in the second column heading "$R^1$" for compound No. 481, change "4-Me, 7-Me" to -- 4-Cl --;
Table 13, in the second column heading "$R^1$" for compound No. 482, change "4-Cl" to
-- 4-Et --;
Table 13, in the both column heading "$R^1$" for compound No. 491, change "4-(OBzl)" to
-- 4-OBzl --;
Table 13, in column heading "X" for compound No. 496, change "Me" to -- Cl --;
Table 13, in column heading "X" for compound No. 497, change "Bzl" to -- Cl --;
Table 13, in column heading "M" for compound No. 498, change "Hf" to -- Zr --;
Table 13, in column heading "M" for compound No. 499, change "Ti" to -- Zr --;
Table 13, in column heading "M" for compound No. 500, change "Hf" to -- Zr --;
Table 13, in column heading "M" for compound No. 501, change "Ti" to -- Zr --;
Table 13, last column for compound No. 505, change "—Ge(Me)$_2$—" to -- —Ge(Et)$_2$— --;
Table 13, in the second column heading "q+n" for compound No. 506, change "2" to -- 3 --;
Table 13, last column for compound No. 506, change "—Ge(Me)$_2$—" to -- —Ge(Ph)$_2$— --;
Table 13, in the first column heading "Ra" for compound No. 520, change "2-(2-(Py)" to
-- 2-(2-Py) --;

Columns 39 and 40,
Table 13, in the headings, change "$CA^1$: Cyclopendadiene" to -- $CA^1$: Indene --;
Table 13, in the headings, change "$CA^2$: Cyclopendadiene" to -- $CA^2$: Indene --;
Table 13, in the heading, change "q+n Y" to -- q+n     Y --;
Table 14, in the headings, change "$CA^1$: Cyclopendadiene" to
-- $CA^1$: Tetrahydroindene --;
Table 14, in the headings, change "$CA^2$: Cyclopendadiene" to
-- $CA^2$: Tetrahydroindene --;
Table 14, in the heading, change "q+n Y" to -- q+n     Y --;
Table 14, in the second heading "Ra" for compound No. 525, change "3-(2-Fu)" to
-- 2-(2-Fu) --;
Table 14, in the second column heading "q+n" for compound No. 530, change "2" to -- 3 --;

UNITED STATES PATENT AND TRADEMARK OFFICE
CERTIFICATE OF CORRECTION

PATENT NO.  : 6,169,051 B1
DATED       : January 2, 2001
INVENTOR(S) : Seiki Mitani et al.

It is certified that error appears in the above-identified patent and that said Letters Patent is hereby corrected as shown below:

Columns 39 and 40 (cont'd),
Table 14, in the second column heading "$R^1$" for compound No. 531, change "3-Me, 7-Me" to -- 4-Me, 7-Me --;
Table 14, in the second column heading "q+n" for compound No. 531, change "2" to -- 3 --;
-Table 14, in the second column heading "$R^1$" for compound No. 532, change "4-Me, 7-Me" to -- 4-Cl --;
Table 14, in the second column heading "$R^1$" for compound No. 533, change "4-Cl" to -- 4-Et --;
Table 14, in the both column heading "$R^1$" for compound No. 542, change "4-(OBzl)" to -- 4-OBzl --;
Table 14, in column heading "X" for compound No. 547, change "Me" to -- Cl --;
Table 14, in column heading "X" for compound No. 548, change "Bzl" to -- Cl --;
Table 14, in column heading "M" for compound No. 549, change "Hf" to -- Zr --;
Table 14, in column heading "M" for compound No. 550, change "Ti" to -- Zr --;
Table 14, in column heading "M" for compound No. 551, change "Hf" to -- Zr --;
Table 14, in column heading "M" for compound No. 552, change "Ti" to -- Zr --;
Table 14, last column for compound No. 556, change "—$C(Me)_2$—" to -- —$C(Et)_2$— --;
Table 14, in the second column heading "q+n" for compound No. 557, change "2" to -- 3 --;
Table 14, last column for compound No. 557, change "—$C(Me)_2$—" to -- —$C(Ph)_2$— --;
Table 15, in the headings, change "$CA^1$: Cyclopendadiene" to
-- $CA^1$: Tetrahydroindene --;
Table 15, in the headings, change "$CA^2$: Cyclopendadiene" to
-- $CA^2$: Tetrahydroindene--;
Table 15, in the heading, change "q+n Y" to -- q+n    Y --;
Table 14, in the first column heading "Ra" for compound No. 571, change "2-(2-(Py)" to
-- 2-(2-Py) --;
Table 14, in the second column heading "Ra" for compound No. 572, change "2-(2-(BzFu)" to -- 2-(2-BzFu) --;
Table 14, in the second column heading "Ra" for compound No. 573, change "2-(2-(BzFu)" to -- 2-(2-BzFu) --;
Table 15, in the second heading "Ra" for compound No. 576, change "3-(2-Fu)" to -- 2-(2-Fu) --;

UNITED STATES PATENT AND TRADEMARK OFFICE
CERTIFICATE OF CORRECTION

PATENT NO. : 6,169,051 B1
DATED : January 2, 2001
INVENTOR(S) : Seiki Mitani et al.

It is certified that error appears in the above-identified patent and that said Letters Patent is hereby corrected as shown below:

Columns 41 and 42,
Table 15, in the headings, change "$CA^1$: Cyclopendadiene" to
-- $CA^1$: Tetrahydroindene --;
Table 15, in the headings, change "$CA^2$: Cyclopendadiene" to
-- $CA^2$: Tetrahydroindene--;
Table 15, in the heading, change "q+n Y" to -- q+n    Y --;
Table 15, in the second column heading "q+n" for compound No. 581, change "2" to -- 3 --;
Table 15, in the second column heading "$R^1$" for compound No. 582, change "3-Me, 7-Me" to -- 4-Me, 7-Me --;
Table 15, in the second column heading "q+n" for compound No. 582, change "2" to -- 3 --;
Table 15, in the second column heading "$R^1$" for compound No. 583, change "4-Me, 7-Me" to -- 4-Cl --;
Table 15, in the second column heading "$R^1$" for compound No. 584, change "4-Cl" to -- 4-Et --;
Column 41 and 42, Table 15, in the both column heading "$R^1$" for compound No. 593, change "4-(OBzl)" to -- 4-OBzl --;
Table 15, in column heading "X" for compound No. 598, change "Me" to -- Cl --;
Table 15, in column heading "X" for compound No. 599, change "Bzl" to -- Cl --;
Table 15, in column heading "M" for compound No. 600, change "Hf" to -- Zr --;
Table 15, in column heading "M" for compound No. 601, change "Ti" to -- Zr --;
Table 15, in column heading "M" for compound No. 602, change "Hf" to -- Zr --;
Table 15, in column heading "M" for compound No. 603, change "Ti" to -- Zr --;
Table 15, last column for compound No. 607, change "—$C_2(Me)_4$" to -- —$C_2(Et)_4$— --;
Table 15, in the second column heading "q+n" for compound No. 608, change "2" to -- 3 --;
Table 15, last column for compound No. 608, change "—$C_2(Me)_4$—" to -- —$C_2(Ph)_4$— --;
Table 16, in the headings, change "$CA^1$: Cyclopendadiene" to
-- $CA^1$: Tetrahydroindene --;
Table 16, in the headings, change "$CA^2$: Cyclopendadiene" to
-- $CA^2$: Tetrahydroindene--;
Table 16, in the heading, change "q+n Y" to -- q+n    Y --;
Table 15, in the first column heading "Ra" for compound No. 622, change "2-(2-(Py)" to -- 2-(2-Py)--;
Table 15, in the second column heading "Ra" for compound No. 623, change "2-(2-(BzFu)" to -- 2-(2-BzFu) --;
Table 15, in the second column heading "Ra" for compound No. 624, change "2-(2-(BzFu)" to -- 2-(2-BzFu) --;
Table 16, in the second heading "Ra" for compound No. 625, change "3-(2-Fu)" to -- 2-(2-Fu) --;
Table 15, in the second column heading "Ra" for compound No. 626, change "2-[2-(l-Me-Pyr)]" to -- 2-[2-(N-Me-Pyr)] --;

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

Columns 41 and 42 (cont'd),
Table 16, in the second heading "Ra" for compound No. 627, change "3-(2-Fu)" to -- 2-(2-Fu) --;
Table 16, in the both column heading "$R^1$" for compound No. 644, change "4-(OBzl)" to -- 4-OBzl --;

Columns 43 and 44,
Table 16, in the headings, change "$CA^1$: Cyclopendadiene" to
-- $CA^1$: Tetrahydroindene --;
Table 16, in the headings, change "$CA^2$: Cyclopendadiene" to
-- $CA^2$: Tetrahydroindene--;
Table 16, in the heading, change "q+n Y" to -- q+n    Y --;
Table 16, in column heading "X" for compound No. 649, change "Me" to -- Cl --;
Table 16, in column heading "X" for compound No. 650, change "Bzl" to -- Cl --;
Table 16, in column heading "M" for compound No. 651, change "Hf" to -- Zr --;
Table 16, in column heading "M" for compound No. 652, change "Ti" to -- Zr --;
Table 16, in column heading "M" for compound No. 653, change "Hf" to -- Zr --;
Table 16, in column heading "M" for compound No. 654, change "Ti" to -- Zr --;
Table 16, last column for compound No. 658, change "—$Si(Me)_2$—" to -- —$Si(Et)_2$— --;
Table 16, in the second column heading "q+n" for compound No. 659, change "2" to
-- 3 --;
Table 16, last column for compound No. 659, change "—$Si(Me)_2$—" to -- —$Si(Ph)_2$— --;
Table 17, in the headings, change "$CA^1$: Cyclopendadiene" to
-- $CA^1$: Tetrahydroindene --;
Table 17, in the headings, change "$CA^2$: Cyclopendadiene" to
-- $CA^2$: Tetrahydroindene--;
Table 17, in the heading, change "q+n Y" to -- q+n    Y --;
Table 16, in the first column heading "Ra" for compound No. 673, change "2-(2-(Py)" to
-- 2-(2-Py) --.
Table 16, in the second column heading "Ra" for compound No. 674, change "2-(2-(BzFu)" to -- 2-(2-BzFu) --;
Table 16, in the second column heading "Ra" for compound No. 675, change "2-(2-(BzFu)" to -- 2-(2-BzFu) --;
Table 17, in the second heading "Ra" for compound No. 678, change "3-(2-Fu)" to -- 2-(2-Fu) --;
Table 17, in the both column heading "$R^1$" for compound No. 695, change "4-(OBzl)" to -- 4-OBzl --;

UNITED STATES PATENT AND TRADEMARK OFFICE
CERTIFICATE OF CORRECTION

PATENT NO. : 6,169,051 B1
DATED : January 2, 2001
INVENTOR(S) : Seiki Mitani et al.

It is certified that error appears in the above-identified patent and that said Letters Patent is hereby corrected as shown below:

Columns 43 and 44 (cont'd),
Table 17, in column heading "X" for compound No. 700, change "Me" to -- Cl --;
Table 17, in column heading "X" for compound No. 701, change "Bzl" to -- Cl --;
Table 17, in column heading "M" for compound No. 702, change "Hf" to -- Zr --;
Table 17, in column heading "M" for compound No. 703, change "Ti" to -- Zr --;
Table 17, in column heading "M" for compound No. 704, change "Hf" to -- Zr --;
Table 17, in column heading "M" for compound No. 705, change "Ti" to -- Zr --;
Table 17, last column for compound No. 709, change "—Ge(Me)$_2$—" to -- —Ge(Et)$_2$— --;
Table 17, in the second column heading "q+n" for compound No. 710, change "2" to -- 3 --;
Table 17, last column for compound No. 710, change "—Ge(Me)$_2$—" to -- —Ge(Ph)$_2$— --;

Columns 45 and 46,
Table 17, in the headings, change "CA$^1$: Cyclopendadiene" to -- CA$^1$: Tetrahydroindene --;
Table 17, in the headings, change "CA$^2$: Cyclopendadiene" to -- CA$^2$: Tetrahydroindene--;
Table 17, in the heading, change "q+n Y" to -- q+n    Y --;
Table 18, in the headings, change "CA$^1$: Cyclopendadiene" to -- CA$^1$: Benzoindene--;
Table 18, in the headings, change "CA$^2$: Cyclopendadiene" to -- CA$^2$: Benzoindene--;
Table 18, in the heading, change "q+n Y" to -- q+n    Y --;
Table 17, in the first column heading "Ra" for compound No. 724, change "2-(2-(Py)" to -- 2-(2-Py) --;
Table 17, in the second column heading "Ra" for compound No. 725, change "2-(2-(BzFu)" to -- 2-(2-BzFu) --;
Table 17, in the second column heading "Ra" for compound No. 726, change "2-(2-(BzFu)" to -- 2-(2-BzFu) --;
Table 18, in the second heading "Ra" for compound No. 729, change "3-(2-Fu)" to -- 2-(2-Fu) --;
Table 18, in the both column heading "R$^1$" for compound No. 746, change "5-(OBzl)" to -- 5-OBzl --;
Table 18, in column heading "X" for compound No. 751, change "Me" to -- Cl --;
Table 18, in column heading "X" for compound No. 752, change "Bzl" to -- Cl --;
Table 18, in column heading "M" for compound No. 753, change "Hf" to -- Zr --;
Table 18, in the first column heading "Ra" for compound No. 754, change "2-(2-Fu), 5-[2-(I-MePyr)" to -- 2-(2-Fu), 5-[2-(I-MePyr)] --;
Table 18, in the second column heading "Ra" for compound No. 754, change "2-(2-Fu), 5-(I-MePyr)" to -- 2-(2-Fu), 5-[2-(I-MePyr)] --;
Table 18, in column heading "M" for compound No. 754, change "Ti" to -- Zr --;
Table 18, in column heading "M" for compound No. 755, change "Hf" to -- Zr --;

UNITED STATES PATENT AND TRADEMARK OFFICE
CERTIFICATE OF CORRECTION

PATENT NO. : 6,169,051 B1
DATED : January 2, 2001
INVENTOR(S) : Seiki Mitani et al.

It is certified that error appears in the above-identified patent and that said Letters Patent is hereby corrected as shown below:

<u>Columns 45 and 46 (cont'd),</u>
Table 18, in the second column heading "$R^1$" for compound No. 755, change "4-Et, 7-Et" to -- 5-Et, 9-Et --;
Table 18, in column heading "M" for compound No. 756, change "Ti" to -- Zr --;
Table 18, in the second column heading "$R^1$" for compound No. 756, change "4-l-Pr, 7-1-Pr" to, -- 5-i-Pr, 9-i-Pr --;
Table 18, in the second column heading "$R^1$" for compound No. 757, change "4-t-Bu, 7-t-Bu" to -- 5-t-Bu, 9-t-Bu --;
Table 18, in the second column heading "$R^1$" for compound No. 758, change "4-Ph, 7-Ph" to -- 5-Ph, 9-Ph --;
Table 18, in the first column heading "$R^1$" for compound No. 759, change "5-Ph, 9-Me" to -- 3-Ph, 9-Me --;
Table 18, in the second column heading "$R^1$" for compound No. 759, change "3-Ph, 7-Me" to -- 3-Ph, 9-Me --;
Table 18, in the second column heading "$R^1$" for compound No. 760, change "4-Me, 7-Me" to -- 5-Me, 9-Me --;
Table 18, last column for compound No. 760, change "—Si(Me)$_2$—" to -- —Si(Et)$_2$— --;
Table 18, in the second column heading "$R^1$" for compound No. 761, change "4-Me, 7-Me" to -- 5-Me, 9-Me --;
Table 18, in the second column heading "q+n" for compound No. 761, change "2" to -- 3 --;
Table 18, last column for compound No. 761, change "—Si(Me)$_2$—" to -- —Si(Ph)$_2$— --;
Table 18, in the second column heading "$R^1$" for compound No. 762, change "4-Ph" to -- 5-Ph --;
Table 18, in the second column heading "$R^1$" for compound No. 763, change "4-Ph" to -- 5-Ph --;
Table 18, in the second column heading "$R^1$" for compound No. 764, change "4-Ph" to -- 5-Ph --;
Table 18, in the second column heading "$R^1$" for compound No. 765, change "4-Ph" to -- 5-Ph --;
Table 18, in the second column heading "$R^1$" for compound No. 766, change "3-Me, 7-Me" to -- 3-Me, 9-Me --;
Table 18, in the second column heading "$R^1$" for compound No. 767, change "3-Me, 7--Me" to -- 3-Me, 9-Me --;
Table 18, in the second column heading "$R^1$" for compound No. 768, change "4-Ph" to -- 5-Ph --;
Table 18, in the second column heading "$R^1$" for compound No. 769, change "4-Ph" to -- 5-Ph --;
Table 18, in the second column heading "$R^1$" for compound No. 770, change "4-Ph" to -- 5-Ph --;

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

Columns 45 and 46 (cont'd),
Table 18, in the second column heading "$R^1$" for compound No. 772, change "4-Ph" to -- 5-Ph --;
Table 18, in the second column heading "$R^1$" for compound No. 774, change "4-Ph" to -- 5-Ph --;
Column 45 and 46, Table 18, in the first column heading "Ra" for compound No. 775, change "2-(2-(Py)" to -- 2-(2-Py) --;

Columns 47 and 48,
Table 18, in the headings, change "$CA^1$: Cyclopendadiene" to -- $CA^1$: Benzoindene--;
Table 18, in the headings, change "$CA^2$: Cyclopendadiene" to -- $CA^2$: Benzoindene--;
Table 18, in the heading, change "q+n Y" to -- q+n    Y --;
Table 18, in the second column heading "Ra" for compound No. 776, change "2-(2-(BzFu)" to -- 2-(2-BzFu) --;
Table 18, in the second column heading "$R^1$" for compound No. 776, change "4-Ph" to -- 5-Ph --;
Table 18, in the second column heading "Ra" for compound No. 777, change "2-(2-(BzFu)" to -- 2-(2-BzFu) --;
Table 18, in the second column heading "$R^1$" for compound No. 778, change "4-Ph" to -- 5-Ph --;
Table 19, in the headings, change "$CA^1$: Cyclopendadiene" to -- $CA^1$: Benzoindene--;
Table 19, in the headings, change "$CA^2$: Cyclopendadiene" to -- $CA^2$: Benzoindene--;
Table 19, in the heading, change "q+n Y" to -- q+n    Y --;
Table 19, in the second heading "Ra" for compound No. 780, change "3-(2-Fu)" to -- 2-(2-Fu) --;
Table 19, in both column headings "$R^1$" for compound No. 797, change "5-(OBzl)" to -- 5-OBzl --;
Table 19, in column heading "X" for compound No. 802, change "Me" to -- Cl --;
Table 19, in column heading "X" for compound No. 803, change "Bzl" to -- Cl --;
Table 19, in column heading "M" for compound No. 804, change "Hf" to -- Zr --;
Table 19, in the both column heading "Ra" for compound No. 805, change "2-(2-Fu), 5-[2-(I-MePyr)" to -- 2-(2-Fu), 5-[2-(I-MePyr)] --;
Table 19, in column heading "M" for compound No. 805, change "Ti" to -- Zr--;
Table 19, in column heading "M" for compound No. 806, change "Hf" to -- Zr --;
Table 19, in column heading "M" for compound No. 807, change "Ti" to -- Zr --;
Table 19, last column for compound No. 811, change "—Ge(Me)$_2$—" to -- —Ge(Et)$_2$— --;
Table 19, in the first column heading "R" for compound No. 810, change "5-Ph, 9-Me" to -- 3-Ph, 9-Me --;
Table 19, in the second column heading "q+n" for compound No. 812, change "2" to -- 3 --;

UNITED STATES PATENT AND TRADEMARK OFFICE
CERTIFICATE OF CORRECTION

PATENT NO. : 6,169,051 B1
DATED : January 2, 2001
INVENTOR(S) : Seiki Mitani et al.

It is certified that error appears in the above-identified patent and that said Letters Patent is hereby corrected as shown below:

<u>Columns 47 and 48 (cont'd),</u>
Table 19, last column for compound No. 812, change "—Ge(Me)$_2$—" to -- —Ge(Ph)$_2$— --;
Table 19, in the first column heading "Ra" for compound No. 826, change "2-(2-(Py)" to -- 2-(2-Py) --;
Table 19, in the second column heading "Ra" for compound No. 827, change "2-(2-(BzFu)" to -- 2-(2-BzFu) --;
Table 19, in the second column heading "Ra" for compound No. 828, change "2-(2-(BzFu)" to -- 2-(2-BzFu) --;

<u>Columns 49 and 50,</u>
Table 20, last column for compound No. 852, change "—Si(Me)$_2$—" to -- —Si(Et)$_2$— --;
Table 20, last column for compound No. 853, change "—Si(Me)$_2$—" to -- —Si(Ph)$_2$— --;
Table 20, in column heading "X" for compound No. 862, change "Me" to -- Cl --;
Table 20, in column heading "X" for compound No. 863, change "Bzl" to -- Cl --;
Table 20, in column heading "X" for compound No. 873, change "Me" to -- Cl --; and
Table 20, in column heading "X" for compound No. 874, change "Bzl" to -- Cl --; and
Table 20, in the first column heading "Ra" for compound No. 875, change "2-[2-(1-Me-Fu)]" to -- 2-[2-(1-Me-Pyr)] --.

<u>Column 52,</u>
Line 52, change "set froth in" to -- of --;
Line 52, after "claim 1" insert -- , --;
Line 65, delete "(q+n),";
Lines 66 and 67, delete ", in which Z in formula (1) is (CA$^2$)(Ra)$_q$(R$^1$)$_n$";

<u>Column 53,</u>
Line 1, change "set forth in" to -- of --;
Lines 15 and 16, delete "in which CA$^2$, q and n in formula (2) are each identical with CA$^1$, p and m,";
Line 16, change "is" to -- includes --;
Line 18, insert -- the plane containing -- before "M";
Line 19, insert -- meso form consisting of a -- before "stereostructurally";
Line 19, change "meso form or" to -- compound with respect to the plane containing M and --;

UNITED STATES PATENT AND TRADEMARK OFFICE
CERTIFICATE OF CORRECTION

PATENT NO.    : 6,169,051 B1
DATED         : January 2, 2001
INVENTOR(S)   : Seiki Mitani et al.

It is certified that error appears in the above-identified patent and that said Letters Patent is hereby corrected as shown below:

Column 54,
Line 18, change "set forth in" to -- of --;
Line 19, change "claim" to -- claims --;
Line 19, change "present" to -- substituted --;
Line 20, delete "substituted" (first occurrence);
Line 20, change "a substituted" (second occurrence) to -- an --;
Line 21, delete "substituted";
Line 21, delete "sub-";
Line 22, delete "stituted"

Column 56,
Line 51, change "set forth in" to -- of --;
Line 51, change "claim" to -- claims --;
Line 53, change "formed from" to -- comprising --;
Line 54, change "set forth in" to -- of --;
Line 55, change "finely divided support" to -- support in the form of finely divided particles --;
Line 56, change "for olefin polymerization set forth in" to -- of --;
Line 58, delete "finely";
Line 59, delete "divided";
Line 60, change "for olefin polymerization set forth in" to -- of --;
Line 61, delete "finely divided support is an inorganic";
Line 62, change "fine particles" to -- support is finely divided inorganic particles --;
Line 66, change "characterized by" to -- which comprises --;
Line 67, change "for olefin polymerization set forth" to -- as defined --;

Column 57,
Line 1, delete "for the production of an olefin polymer set";
Line 2, change "forth in" to -- of --;
Line 5, change "characterized by" to -- which comprises --;
Line 6, change "for olefin polymerization set forth" to -- as defined --;
Line 8, delete "for the production of an olefin polymer set";
Line 9, change "forth in" to -- of --;
Line 11, delete "for the production of an olefin polymer set";
Line 12, change "forth in" to -- of --;
Line 36, change "27" to -- 4 --;

UNITED STATES PATENT AND TRADEMARK OFFICE
CERTIFICATE OF CORRECTION

PATENT NO.   : 6,169,051 B1
DATED        : January 2, 2001
INVENTOR(S)  : Seiki Mitani et al.

It is certified that error appears in the above-identified patent and that said Letters Patent is hereby corrected as shown below:

Column 58,
Line 14, change "27" to -- 4 --;
Line 16, change "27" to -- 4 --;
Line 19, change "(2a)" to -- (2A) --; and
Line 31, change "27" to -- 4 --.

Signed and Sealed this

Third Day of June, 2003

JAMES E. ROGAN
*Director of the United States Patent and Trademark Office*